US011407804B2

(12) United States Patent
Payne et al.

(10) Patent No.: US 11,407,804 B2
(45) Date of Patent: Aug. 9, 2022

(54) COMPOSITIONS AND METHODS OF CHIMERIC AUTOANTIBODY RECEPTOR T CELLS

(71) Applicant: THE TRUSTEES OF THE UNIVERSITY OF PENNSYLVANIA, Philadelphia, PA (US)

(72) Inventors: Aimee S. Payne, Merion Station, PA (US); Christoph T. Ellebrecht, Philadelphia, PA (US); Vijay Bhoj, Philadelphia, PA (US); Michael C. Milone, Cherry Hill, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 728 days.

(21) Appl. No.: 16/390,685

(22) Filed: Apr. 22, 2019

(65) Prior Publication Data
US 2019/0315830 A1    Oct. 17, 2019

Related U.S. Application Data

(62) Division of application No. 15/307,644, filed as application No. PCT/US2015/028872 on May 1, 2015, now Pat. No. 10,301,370.

(60) Provisional application No. 61/987,989, filed on May 2, 2014.

(51) Int. Cl.
C07K 14/705 (2006.01)
C07K 16/28 (2006.01)
A61K 39/00 (2006.01)
A61K 48/00 (2006.01)

(52) U.S. Cl.
CPC ........ C07K 14/705 (2013.01); A61K 39/0008 (2013.01); A61K 48/00 (2013.01); C07K 16/28 (2013.01); A61K 2039/5158 (2013.01); A61K 2039/57 (2013.01); C07K 2319/02 (2013.01); C07K 2319/03 (2013.01)

(58) Field of Classification Search
None
See application file for complete search history.

(56) References Cited

U.S. PATENT DOCUMENTS

| | | |
|---|---|---|
| 5,738,847 A | 4/1998 | Braun |
| 6,004,811 A | 12/1999 | Seed et al. |
| 7,550,562 B2 | 6/2009 | Tsunoda et al. |
| 2001/0024831 A1 | 9/2001 | Der Maur et al. |
| 2005/0118676 A1 | 6/2005 | Qi et al. |
| 2006/0257420 A1 | 11/2006 | Zimmerman et al. |
| 2013/0287748 A1 | 10/2013 | June et al. |
| 2014/0050708 A1 | 2/2014 | Powell et al. |
| 2015/0051266 A1 | 2/2015 | Kochenderfer |

FOREIGN PATENT DOCUMENTS

| | | |
|---|---|---|
| WO | 0216414 A2 | 2/2002 |
| WO | 0233101 A1 | 4/2002 |
| WO | 2012079000 A1 | 6/2012 |
| WO | 2012099973 A2 | 7/2012 |
| WO | 2013154760 A1 | 10/2013 |

OTHER PUBLICATIONS

Zhang, "Research progress of autoreactive T cells in the pathogenesis of pemphigus vulgaris", Compilation of Materials for the First International Conference on Allergies of Integrated Traditional and Western Medicine and the Third National Conference on Allergies of Integrated Traditional Chinese and Western Medicine, Jul. 2007, 263 (abstract only).
Zhao, et al., "The effect of single chain variable fragment antibody to EC3-4 fragment of desmoglein 3 in a mouse model of pemphigus vulgaris", Chinese Journal of Dermatology 39(6), 2006, 338-340 (abstract only).
Accession No. NM_001942 originally published 1991.
Accession No. NM_001944 originally published 1991.
Accession No. NM_010079 originally published 1993.
Accession No. NM_030596 originally published 1994.
Accession No. NP_001932 originally published 1991.
Accession No. NP_001935 originally published 1991.
Accession No. NP_034209 originally published 1993.
Accession No. NP_085099 originally published 1994.
Extended European Search Report for European Patent Application No. 15786710.2 dated Apr. 25, 2018.
PCT/US2015/028872 International Search Report and Written Opinion dated Oct. 23, 2015.
Supplementary Partial European Search Report for European Patent Application No. 15786710.2 dated Jan. 9, 2018.
Berkowitz, et al., Desmosome signaling. Inhibition of p38MAPK prevents pemphigus vulgaris IgG-induced cytoskeleton reorganization, J Biol Chem. Jun. 24, 2005;280(25): ,2005 ,23778-23784.
Ding, et al., The Anti-Desmoglein 1 Autoantibodies in Pemphigus Vulgaris Sera are Pathogenic, J. Invest Dermatol., May 1999, vol. 112, No. 5, pp. 739-743.
Ellebrecht, et al., Reengineering chimeric antigen receptor T cells for targeted therapy of autoimmune disease, Science 353(6295) ,2016 ,179-184.
Grupp, et al., Chimeric Antigen Receptor-Modified T Cells for Acute Lymphoid Leukemia, 2013, N Engl J Med 368 (16):1509-1518.

(Continued)

Primary Examiner — James D Schultz
(74) Attorney, Agent, or Firm — Saul Ewing Arnstein & Lehr LLP; Kathryn Doyle

(57) ABSTRACT

The invention includes compositions comprising at least one chimeric autoantibody receptor (CAAR) specific for an autoantibody, vectors comprising the same, compositions comprising CAAR vectors packaged in viral particles, and recombinant T cells comprising the CAAR. The invention also includes methods of making a genetically modified T cell expressing a CAAR (CAART) wherein the expressed CAAR comprises a desmoglein extracellular domain.

19 Claims, 43 Drawing Sheets
Specification includes a Sequence Listing.

(56) References Cited

OTHER PUBLICATIONS

Jyothi, et al., Targeting autoantigen-specific T cells and suppression of autoimmune encephalomyelitis with receptor-modified T lymphocytes, Nat Biotechnol. Dec. 2002;20(12) ,2002 ,1215-1220.

Porter, et al., Chimeric Antigen Receptor-Modified T Cells in Chronic Lymphoid Leukemia, 2011, N Engl J Med 365 (8):725-733.

Proby, et al., Development of chimeric molecules for recognition and targeting of antigen-specific B cells in pemphigus vulgaris, Br J Dermatol. 142(2) ,2000 ,321-330.

Song, et al., In vivo persistence, tumor localization, and antitumor activity of CAR-engineered T cells is enhanced by costimulatory signaling through CD137 (4-1BB), Cancer Res. 71(13) ,2011 ,4617-4627.

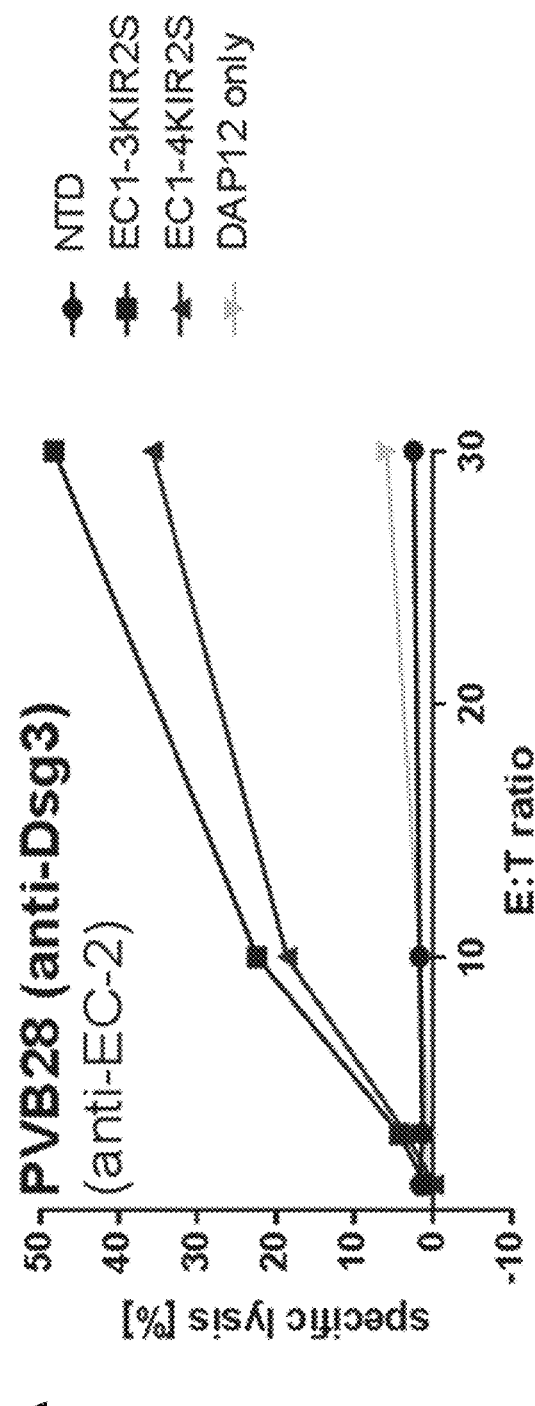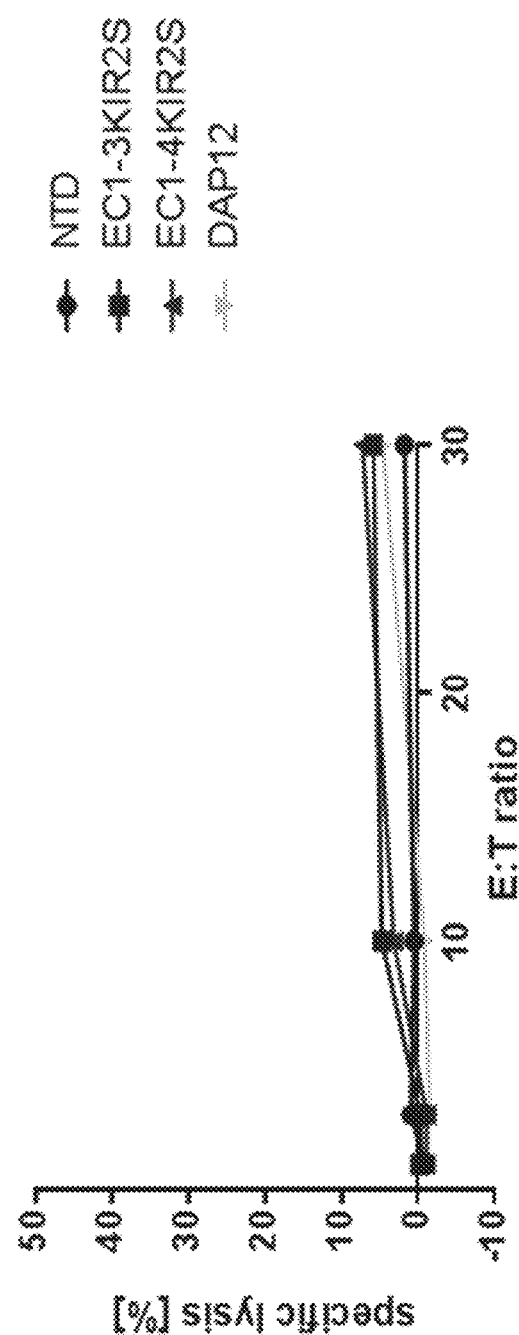
Figure 39A
Figure 39B

COMPOSITIONS AND METHODS OF CHIMERIC AUTOANTIBODY RECEPTOR T CELLS

CROSS REFERENCE TO RELATED APPLICATIONS

This application is a divisional of, and claims priority to, U.S. patent application Ser. No. 15/307,644, filed Oct. 28, 2016, issued as U.S. Pat. No. 10,301,370, which is a 35 U.S.C. § 371 national phase application from, and claims priority to, International Application No. PCT/US2015/028872, filed May 1, 2015, and published under PCT Article 21(2) in English, which claims priority to and the benefit of U.S. Provisional Application No. 61/987,989, filed May 2, 2014, all of which applications are incorporated herein by reference in their entireties.

STATEMENT REGARDING FEDERALLY SPONSORED RESEARCH OR DEVELOPMENT

This invention was made with government support under AR057001, awarded by the National Institutes of Health. The government has certain rights in the invention.

BACKGROUND OF THE INVENTION

Autoimmunity is the third most common category of disease in the United States, affecting 8% of the population. There are two basic categories of autoimmune diseases: those predominantly caused by T cells, and those predominantly caused by B cells and the autoantibodies they produce. Pemphigus vulgaris (PV) is a model autoantibody-mediated disease, in which autoantibodies against the skin cell adhesion protein desmoglein 3 (Dsg3) cause potentially fatal blistering of the skin and mucous membranes.

Current therapies focus on general immune suppression to reduce all antibodies, but these strategies also target good antibodies that protect us from infection. Because pemphigus is a chronic remitting-relapsing disease, such treatments are associated with multiple side effects, including risk of fatal infection and secondary cancers. As an example, rituximab, an anti-CD20 monoclonal antibody reagent, has been reported to have excellent efficacy in the treatment of pemphigus vulgaris, with 95% of patients achieving complete healing of blisters within 3 months, and 35% of patients achieving complete remission off all systemic therapies during long term follow up. However, greater than 80% of patients will relapse (presumably since the efficacy of CD20+ B cell depletion by rituximab is usually incomplete), and serious infections are not uncommon, reported to occur in 7% of autoimmune disease patients treated with rituximab, with fatal infection in 1-2%. Therefore, patients with severe autoimmune diseases, such as pemphigus vulgaris, paraneoplastic pemphigus or pemphigus foliaceus, are no longer dying from their disease, but instead are suffering from complications of treatment.

However, therapeutic strategies for the treatment of PV to target only the autoreactive B cells do not currently exist. Systemic corticosteroids, azathioprine, mycophenolate mofetil and cyclophosphamide are effective in the treatment of PV, but non-specifically inhibit lymphocyte proliferation. Rituximab targets CD20 expressed on most B cells, but lacks specificity to only the autoreactive B cells.

As a result, therapeutic strategies can pose serious side effects related to general immune suppression, including fatal infection and secondary cancers. Therefore, a need exists for a therapy that targets only the autoreactive B cells.

SUMMARY OF THE INVENTION

As described below, the present invention includes compositions of and methods for their use, of a chimeric autoantibody receptor (CAAR) specific for an autoantibody.

One aspect of the invention includes an isolated nucleic acid sequence encoding a chimeric autoantibody receptor (CAAR), wherein the isolated nucleic acid sequence comprises a nucleic acid sequence of an autoantigen or fragment thereof, a nucleic acid sequence of a transmembrane domain, a nucleic acid sequence of an intracellular domain of a costimulatory molecule, and a nucleic acid sequence of a signaling domain.

In another aspect, the invention includes a vector comprising the isolated nucleic acid sequence described herein.

In still another aspect, the invention includes an isolated chimeric autoantibody receptor (CAAR) comprising an extracellular domain comprising an autoantigen or fragment thereof, a transmembrane domain, and an intracellular signaling domain.

In yet another aspect, the invention includes a genetically modified cell comprising the CAAR described herein.

In various embodiments of the above aspects or any other aspect of the invention delineated herein, the autoantigen is selected from the group consisting of Dsg1, Dsg3, and a fragment thereof. In one embodiment, the autoantigen comprises Dsg3 comprising an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:36.

In another embodiment, the autoantigen comprises Dsg3 and the isolated nucleic acid sequence further comprises a nucleic acid sequence encoding a propeptide of Dsg3. In some embodiments that include the Dsg3 propeptide, it comprises an amino acid sequence of SEQ ID NO:2.

In another embodiment, the isolated nucleic acid sequence further comprises a nucleic acid sequence of a CD8 alpha chain signal peptide. In some embodiments that include the CD8 alpha chain signal peptide, it comprises an amino acid sequence of SEQ ID NO:1.

In yet another embodiment, the nucleic acid sequence of the transmembrane domain encodes a CD8 alpha chain hinge and transmembrane domain. In some embodiments that include the CD8 alpha chain hinge and transmembrane domain, the transmembrane domain comprises an amino acid sequence of SEQ ID NO:13.

In still another embodiment, the isolated nucleic acid sequence further comprises a nucleic acid sequence of a peptide linker. In some embodiments that include the peptide linker, it comprises an amino acid sequence of SEQ ID NO:14.

In another embodiment, the nucleic acid sequence of the intracellular signaling domain comprises a nucleic acid sequence encoding a CD137 intracellular domain. In some embodiments that include the CD137 intracellular domain, the intracellular signaling domain comprises an amino acid sequence of SEQ ID NO:15.

In yet another embodiment, the nucleic acid sequence of the intracellular signaling domain comprises a nucleic acid sequence encoding a CD3 zeta signaling domain. In some embodiments that include the CD3 zeta signaling domain, the intracellular signaling domain comprises an amino acid sequence of SEQ ID NO:16.

In one embodiment, the cell comprising the CAAR, expresses it and has high affinity to autoantibodies expressed on B cells. In another embodiment, the cell expresses the CAAR and induces killing of B cells expressing autoantibodies. In still another embodiment, the cell expresses the CAAR and has low affinity to antibodies bound to a Fc receptor. In yet another embodiment, the cell expresses the CAAR and has limited toxicity toward healthy cells. In another embodiment, the cell is selected from the group consisting of a helper T cell, a cytotoxic T cell, a memory T cell, regulatory T cell, gamma delta T cell, natural killer (NK) cell, cytokine induced killer cell, a cell line thereof, and other effector cell.

In another aspect, the invention includes a method for treating an autoimmune disease in a subject, the method comprising: administering to the subject an effective amount of a genetically modified T cell comprising an isolated nucleic acid sequence encoding a chimeric autoantibody receptor (CAAR), wherein the isolated nucleic acid sequence comprises an extracellular domain comprising an autoantigen or fragment thereof, a nucleic acid sequence of a transmembrane domain, and a nucleic acid sequence of an intracellular signaling domain, thereby treating the autoimmune disease in the subject. The autoimmune disease includes pemphigus vulgaris, paraneoplastic pemphigus, and pemphigus foliaceus.

In various embodiments of the above aspects or any other aspect of the invention delineated herein, the subject is a human. In another embodiment, the modified T cell targets a B cell.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 39A is a graph showing killing of anti-Dsg3 (PVB28 anti-EC2) cells by Dsg3 EC1-3 and Dsg3 EC1-4 KIR-CAART cells in a 16 hour chromium release assay.

FIG. 39B is a graph showing that no killing of wild type K562 cells by the Dsg3 KIR CAARs occurs.

DETAILED DESCRIPTION

Figure 1:
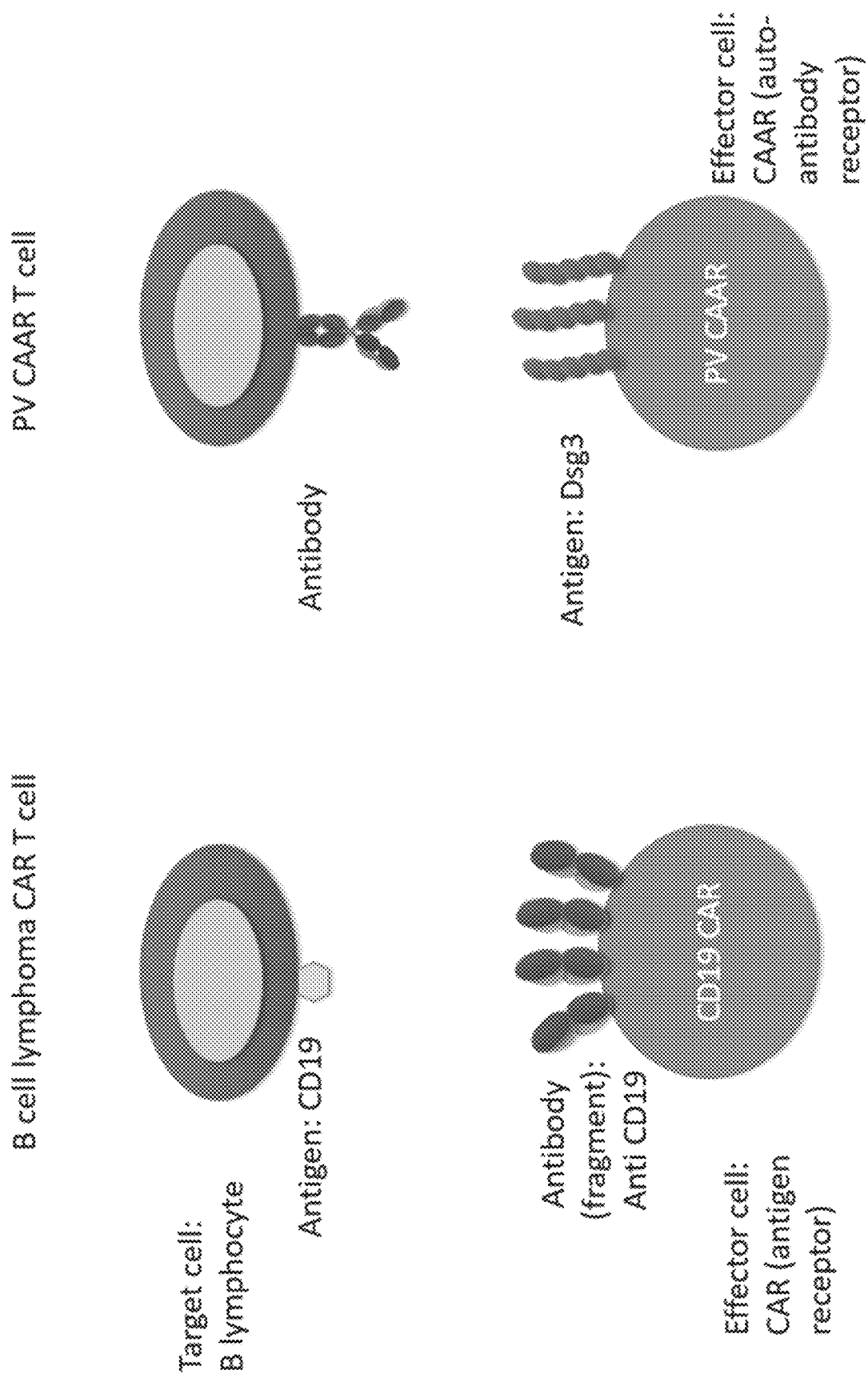
FIG. 1 is a schematic drawing that depicts how the proposed chimeric autoantibody receptor (CAAR) is distinct from all previously developed technologies.

The invention includes compositions comprising at least one chimeric autoantibody receptor (CAAR) specific for an autoantibody, vectors comprising the same, compositions comprising CAAR vectors packaged in viral particles, and recombinant T cells comprising the CAAR. The invention also includes methods of making a genetically modified T cell expressing a CAAR (CAART) wherein the expressed CAAR comprises a desmoglein extracellular domain.

The present invention also relates generally to the use of T cells engineered to express a Chimeric AutoAntibody Receptor (CAAR) to treat an autoimmune disease associated with expression of self-antigens. In one embodiment, the T cells expressing the CAAR of the invention specifically bind to and kill desmoglein 1 or 3 autoantibody expressing cells, but not normal antibody expressing cells.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in some instances ±5%, in some instances ±1%, and in some instance ±0.1% from the specified value, as such variations are appropriate to perform the disclosed methods.

The term "antibody," as used herein, refers to an immunoglobulin molecule binds with an antigen. Antibodies can be intact immunoglobulins derived from natural sources or from recombinant sources and can be immunoreactive portions of intact immunoglobulins. Antibodies are typically tetramers of immunoglobulin molecules. The antibody in the present invention may exist in a variety of forms where the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "high affinity" as used herein refers to high specificity in binding or interacting or attraction of one molecule to a target molecule.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

By "autoantigen" is meant an endogenous antigen that stimulates production of an autoimmune response, such as production of autoantibodies. Autoantigen also includes a self-antigen or antigen from a normal tissue that is the target of a cell-mediated or an antibody-mediated immune response that may result in the development of an autoimmune disease. Examples of autoantigens include, but are not limited to, desmoglein 1, desmoglein 3, and fragments thereof.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

"Autoantibody" refers to an antibody that is produced by a B cell specific for an autoantigen.

The term "autoimmune disease" as used herein is defined as a disorder or condition that results from an antibody mediated autoimmune response against autoantigens. An autoimmune disease results in the production of autoantibodies that are inappropriately produced and/or excessively produced to a self-antigen or autoantigen.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

"Chimeric autoantibody receptor" or "CAAR" refers to an engineered receptor that is expressed on a T cell or any other effector cell type capable of cell-mediated cytotoxicity. The CAAR includes an antigen or fragment thereof that is specific for a pathogenic autoantibody. The CAAR also includes a transmembrane domain, an intracellular domain and a signaling domain.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, for example, one or more amino acid residues within the extracellular regions of the CAAR of the invention can be replaced with other amino acid residues having a similar side chain or charge and the altered CAAR can be tested for the ability to bind autoantibodies using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

"Desmoglein 1" or "Dsg1" refers to a calcium binding transmembrane glycoprotein that is a component of desmosomes found in cell-cell junctions between epithelial cells. An exemplary Dsg1 sequence includes human Dsg1 found at GenBank Accession No. NM_001942 and NP_001932, or a fragment thereof, and the mouse Dsg1 sequence found at NM_010079 or NP_034209, or a fragment thereof.

"Desmoglein 3" or "Dsg3" refers to a calcium binding transmembrane glycoprotein that is a component of desmosomes found in cell-cell junctions between epithelial cells. An exemplary Dsg3 sequence includes human Dsg3 found at GenBank Accession No. NM_001944 and NP_001935 (P32926), or a fragment thereof, and the mouse Dsg3 sequence found at NM_030596 or NP_085099, or a fragment thereof.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by a promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Intracellular domain" refers to a portion or region of a molecule that resides inside a cell.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "proinflammatory cytokine" refers to a cytokine or factor that promotes inflammation or inflammatory responses. Examples of proinflammatory cytokines include, but are not limited to, chemokines (CCL, CXCL, CX3CL, XCL), interleukins (such as, IL-1, IL-2, IL-3, IL-5, IL-6, IL-7, IL-9, IL10 and IL-15), interferons (IFNγ), and tumor necrosis factors (TNFα and TNFβ).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

"Signaling domain" refers to the portion or region of a molecule that recruits and interacts with specific proteins in response to an activating signal.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

"Transmembrane domain" refers to a portion or a region of a molecule that spans a lipid bilayer membrane.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an WIC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Chimeric AutoAntibody Receptor (CAAR)

The present invention is partly based on the discovery that chimeric autoantibody receptors can be used to target autoantibodies that cause autoimmune disease. The invention includes compositions comprising at least one chimeric autoantibody receptor (CAAR) specific for an autoantibody, vectors comprising the same, compositions comprising CAAR vectors packaged in viral particles, and recombinant T cells or other effector cells comprising the CAAR. The invention also includes methods of making a genetically modified T cell expressing a CAAR (CAART) wherein the expressed CAAR comprises a desmoglein extracellular domain.

The antigens for many of autoantibody-mediated diseases have been described. The present invention includes a technology for treating autoantibody-mediated diseases. In particular, technologies that target B cells that ultimately produce the autoantibodies and display the autoantibodies on their cell surfaces, mark these B cells as disease-specific targets for therapeutic intervention. The invention therefore includes a method for efficiently targeting and killing the pathogenic B cells in autoimmune diseases by targeting the disease-causing B cells using an antigen-specific (e.g., desmoglein 3) chimeric autoantibody receptor (or CAAR). In one embodiment of the present invention, only specific anti-Dsg3 autoantibody-expressing B cells are killed, thus leaving intact the beneficial B cells and antibodies that protect from infection.

The present invention encompasses a recombinant DNA construct comprising nucleic acid sequences that encode an extracellular domain comprising an autoantigen or a fragment thereof, in one aspect, a human Dsg1, Dsg3 or a fragment thereof, wherein the sequence of the autoantigen or fragment thereof is operably linked to a nucleic acid sequence of an intracellular signaling domain. The intracellular signaling domain or otherwise the cytoplasmic domain comprises, a costimulatory signaling region. The costimulatory signaling region refers to a portion of the CAAR comprising the intracellular domain of a costimulatory molecule. Costimulatory molecules are cell surface molecules that are required for an efficient T cell activation.

In one aspect, the invention includes an isolated nucleic acid sequence encoding a chimeric autoantibody receptor (CAAR), wherein the isolated nucleic acid sequence comprises an extracellular domain comprising an autoantigen or fragment thereof, a nucleic acid sequence of a transmembrane domain, and a nucleic acid sequence of an intracellular signaling domain.

Autoantigen Moiety

In one exemplary embodiment, a genetically engineered chimeric autoantibody receptor includes the major pemphigus vulgaris autoantigen, desmoglein 3 (Dsg3) or fragments thereof, on the cell surface of T cells. In this embodiment, the CAAR comprises a propeptide, such as a human desmoglein 3 propeptide (amino acids 24-49 of human desmoglein 3): ELRIETKGQYDEEEMTMQQAKRRQKR (SEQ ID NO:2). The human Dsg3 propeptide prevents adhesion of the Dsg3 protein to itself within the synthetic pathway of the cell and is cleaved off by furin or furin-like peptidases in the late Golgi. In one embodiment, the isolated nucleic acid sequence encoding the CAAR comprises a nucleic acid sequence of a propeptide of Dsg3. In another embodiment, the propeptide of Dsg3 encodes an amino acid sequence comprising SEQ ID NO:2. In yet another embodiment, the CAAR comprises a propeptide of Dsg3. In still another embodiment, the CAAR comprises a propeptide of Dsg3 comprising SEQ ID NO:2, such as:

a) human desmoglein 3 extracellular domains 1-5 (amino acids 50-615 of human desmoglein 3, uniprot P32926. The extracellular domains of Dsg3 provide the target for autoimmune Dsg3 specific B cells.

```
                                            (SEQ ID NO: 3)
EWVKFAKPCREGEDNSKRNPIAKITSDYQATQKITYRISGVGIDQPPFGI

FVVDKNTGDINITAIVDREETPSFLITCRALNAQGLDVEKPLILTVKILD

INDNPPVFSQQIFMGEIEENSASNSLVMILNATDADEPNHLNSKIAFKIV

SQEPAGTPMFLLSRNTGEVRTLTNSLDREQASSYRLVVSGADKDGEGLST

QCECNIKVKDVNDNFPMFRDSQYSARIEENILSSELLRFQVTDLDEEYTD

NWLAVYFFTSGNEGNWFEIQTDPRTNEGILKVVKALDYEQLQSVKLSIAV

KNKAEFHQSVISRYRVQSTPVTIQVINVREGIAFRPASKTFTVQKGISSK

KLVDYILGTYQAIDEDTNKAASNVKYVMGRNDGGYLMIDSKTAEIKFVKN

MNRDSTFIVNKTITAEVLAIDEYTGKTSTGTVYVRVPDFNDNCPTAVLEK

DAVCSSSPSVVVSARTLMNRYTGPYTFALEDQPVKLPAVWSITTLNATSA

LLRAQEQIPPGVYHISLVLTDSQNNRCEMPRSLTLEVCQCDNRGICGTSY

PTTSPGTRYGRPHSGR.
``` b) same as a), but with only the EC1-2 domains (amino acids 50-268 of human desmoglein 3, P32926). (SEQ ID NO:4).

c) same as a), but with only the EC1-3 domains (amino acids 50-383 of human desmoglein 3, P32926). (SEQ ID NO:5).

d) same as a), but with only the EC1-4 domains (amino acids 50-499 of human desmoglein 3, P32926). (SEQ ID NO:6).

e) same as a), but with only the EC2-3 domains (amino acids 159-383 of human desmoglein 3, P32926). (SEQ ID NO:7).

f) same as a), but with only the EC3-4 domains (amino acids 269-499 of human desmoglein 3, P32926). (SEQ ID NO:8).

g) same as a), but with only the EC4-5 domains (amino acids 386-615 of human desmoglein 3, P32926). (SEQ ID NO:9).

h) same as a), but with only the EC2-4 domains (amino acids 159-499 of human desmoglein 3, P32926). (SEQ ID NO:10).

i) same as a), but with only the EC3-5 domains (amino acids 269-615 of human desmoglein 3, P32926). (SEQ ID NO:11).

k) same as a), but with only the EC2-5 domains (amino acids 159-615 of human desmoglein 3, P32926). (SEQ ID NO:12).

In one embodiment, the nucleic acid sequence of the Dsg3 extracellular domain encodes an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12. In another embodiment, the CAAR comprises the Dsg3 extracellular domain comprising an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

In one embodiment, a nucleic acid sequence has at least 80%, 85%, 90%, 91%, 92%, 93%, 94%, 95%, 96%, 97%, 98%, or 99% identity or homology to any nucleic acid sequence described herein. In another embodiment, an amino acid sequence has at least 80%, 85%, 90%, 91%, 92%, 93%, 94%, 95%, 96%, 97%, 98%, or 99% identity or homology to any amino acid sequence described herein.

In another aspect, the constructs described herein comprise an extracellular domain comprising an autoantigen or fragment thereof. In one embodiment, the autoantigen is selected from the group consisting of Dsg1, Dsg3, and a fragment thereof.

In one embodiment, the CAAR of the invention comprises an autoantibody binding domain otherwise referred to as an autoantigen or a fragment thereof. The choice of autoantigen for use in the present invention depends upon the type of autoantibody being targeted. For example, the autoantigen may be chosen because it recognizes an autoantibody on a target cell, such as a B cell, associated with a particular disease state, e.g. an autoimmune disease.

In some instances, it is beneficial that the autoantibody binding domain is derived from the same species in which the CAAR will ultimately be used. For example, for use in humans, it may be beneficial that the autoantibody binding domain of the CAAR comprises an autoantigen that binds an autoantibody or a fragment thereof. Thus, in one embodiment, the autoantibody binding domain portion comprises an epitope of the autoantigen that binds the autoantibody. The epitope is the part of the autoantigen that is specifically recognized by the autoantibody.

Transmembrane Domain

In one embodiment, the CAAR comprises a transmembrane domain, such as, but not limited to, a human T cell surface glycoprotein CD8 alpha chain hinge and/or transmembrane domain (amino acids 136-203 of the human human T cell surface glycoprotein CD8 alpha chain). KPTTTPAPRPPTPAPTIASQPLSLRPEACR-PAAGGAVHTRGLDFACDIYIWAPL AGTCGVLLLSLVIT (SEQ ID NO:13). The human CD8 chain hinge and/or transmembrane domain provides cell surface presentation of the chimeric autoantibody receptor.

With respect to the transmembrane domain, in various embodiments, the CAAR comprises a transmembrane domain that is fused to the extracellular domain of the CAAR. In one embodiment, the CAAR comprises a transmembrane domain that naturally is associated with one of the domains in the CAAR. In some instances, the transmembrane domain is be selected or modified by amino acid substitution to avoid binding to the transmembrane domains of the same or different surface membrane proteins in order to minimize interactions with other members of the receptor complex.

The transmembrane domain may be derived either from a natural or from a synthetic source. When the source is natural, the domain may be derived from any membrane-bound or transmembrane protein. In one embodiment, the transmembrane domain may be synthetic, in which case it will comprise predominantly hydrophobic residues such as leucine and valine. In one aspect a triplet of phenylalanine, tryptophan and valine will be found at each end of a synthetic transmembrane domain. Optionally, a short oligo- or polypeptide linker, between 2 and 10 amino acids in length may form the linkage between the transmembrane domain and the cytoplasmic signaling domain of the CAAR. A glycine-serine doublet provides a particularly suitable linker.

In some instances, a variety of human hinges can be employed as well including the human Ig (immunoglobulin) hinge.

Examples of the hinge and/or transmembrane domain include, but are not limited to, a hinge and/or transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIR, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In one embodiment, the nucleic acid sequence of the transmembrane domain encodes a CD8 alpha chain hinge and/or transmembrane domain. In another embodiment, the nucleic acid sequence of the CD8 alpha chain hinge and/or transmembrane domain encodes an amino acid sequence comprising SEQ ID NO:13.

In yet another embodiment, the transmembrane domain comprises a CD8 alpha chain hinge and/or transmembrane domain.

Cytoplasmic Domain

The cytoplasmic domain or otherwise the intracellular signaling domain of the CAAR of the invention, is responsible for activation of at least one of the normal effector functions of the immune cell in which the CAAR has been placed in.

The term "effector function" refers to a specialized function of a cell.

Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While the entire intracellular signaling domain can be employed, in many cases it is not necessary to use the entire domain. To the extent that a truncated portion of the intracellular signaling domain is used, such truncated portion may be used in place of the intact domain as long as it transduces the effector function signal.

The term "intracellular signaling domain" is thus meant to include any truncated portion of the intracellular domain sufficient to transduce the effector function signal.

Examples of intracellular signaling domains for use in the CAAR of the invention include, but are not limited to, the cytoplasmic portion of the T cell receptor (TCR) and co-receptors that act in concert to initiate signal transduction following antigen receptor engagement, as well as any derivative or variant of these elements and any synthetic sequence that has the same functional capability.

It is well recognized that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory manner or in an inhibitory manner. Primary cytoplasmic signaling sequences that act in a stimulatory manner may contain signaling motifs which are known as immunoreceptor tyrosine-based activation motifs or ITAMs.

Examples of the intracellular signaling domain includes a fragment or domain from one or more molecules or receptors including, but are not limited to, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

In a preferred embodiment, the intracellular signaling domain of the CAAR comprises the CD3-zeta signaling domain by itself or in combination with any other desired cytoplasmic domain(s) useful in the context of the CAAR of the invention. For example, the intracellular signaling domain of the CAAR can comprise a CD3 zeta chain portion and a costimulatory signaling region. The costimulatory signaling region refers to a portion of the CAAR comprising the intracellular domain of a costimulatory molecule. A costimulatory molecule is a cell surface molecule other than an antigen receptor or its ligands that is required for an efficient response of lymphocytes to an antigen.

In yet another embodiment, the intracellular signaling domain encodes a CD137 intracellular domain. In still another embodiment, the CD137 intracellular domain comprises SEQ ID NO:15, such as a human T-cell surface glycoprotein CD3 zeta chain isoform 3 intracellular domain (human CD247, amino acids 52-163) RVKFSRSADAPA-YQQGQNQLYNELNLGRREEYDVLDKRR-GRDPEMGGKPR RKNPQEGLYNELQKDKMAEAYSEI-GMKGERRRGKGHDGLYQGLS TATKDT YDALHMQALPPR (SEQ ID NO:16). The human intracellular CD3 zeta domain provides stimulatory intracellular signaling upon binding to the extracellular autoantigen, such as Dsg1, Dsg3, or a fragment thereof, without HLA restriction.

In another embodiment, the nucleic acid sequence of the intracellular signaling domain comprises a nucleic acid sequence encoding a CD3 zeta signaling domain. In another embodiment, the nucleic acid sequence of the CD3 zeta signaling domain encodes an amino acid sequence comprising SEQ ID NO:16.

In yet another embodiment, the intracellular signaling domain comprises a CD3 zeta signaling domain. In still another embodiment, the CD3 zeta signaling domain comprises SEQ ID NO:16.

Other Domains

In another embodiment, the CAAR and the nucleic acid encoding the CAAR comprise a human T cell surface glycoprotein CD8 alpha chain signal peptide (amino acids 1-21 of the T-cell surface glycoprotein CD8 alpha chain): MALPVTALLLPLALLLHAARP (SEQ ID NO:1). The human CD8 alpha signal peptide is responsible for the translocation of the receptor to the T cell surface. In one embodiment, the isolated nucleic acid sequence encoding the CAAR comprises a nucleic acid sequence of a CD8 alpha chain signal peptide. In another embodiment, the CD8 alpha chain signal peptide encodes an amino acid sequence comprising SEQ ID NO:1. In yet another embodiment, the CAAR comprises a CD8 alpha chain signal peptide.

In still another embodiment, the transmembrane domain comprises a CD8 alpha chain hinge and transmembrane domain comprising SEQ ID NO:13, such as the hinge region mentioned in a) replaced with a peptide linker consisting of the amino acids: SGGGGSGGGGSSG (SEQ ID NO:14) between the EC domains of desmoglein 3 and the CD8 transmembrane domain.

In one embodiment, the isolated nucleic acid sequence encoding the CAAR comprises a nucleic acid sequence of a peptide linker. In another embodiment, the nucleic acid sequence of peptide linker encodes an amino acid sequence comprising SEQ ID NO:14. In another embodiment, the cytoplasmic signaling sequences within the intracellular signaling domain of the CAAR can be linked to each other in a random or specified order. Optionally, a short oligo- or polypeptide linker, for example, between 2 and 10 amino acids in length may form the linkage. A glycine-serine doublet is a particularly suitable linker.

In yet another embodiment, the CAAR comprises a peptide linker. In still another embodiment, the peptide linker comprises SEQ ID NO:14, such as a human tumor necrosis factor receptor superfamily member 9 (also known as CD137 or 4-1BB ligand receptor) intracellular domain (amino acids 214-255 of the human tumor necrosis factor receptor superfamily member 9):

(SEQ ID NO: 15)
KRGRKKLLYIFKQPFMRPVQTTQEEDGCSCRFPEEEEGGCEL.

The human intracellular CD137 domain provides co-stimulatory intracellular signaling upon binding to the extracellular autoantigen, such as Dsg1, Dsg3, or a fragment thereof, without the need of its original ligand.

Any domains and/or fragments of the CAAR, vector, and the promoter may be amplified by PCR or any other means known in the art.

Vector Comprising the CAAR

All vectors described herein comprising different parts of an extracellular portion of human Desmoglein 3 should be construed to be equally compatible with use of human Desmoglein 1 extracellular portion. As such, use of the vectors described herein is exemplified by use of Desmoglein 3, but should be construed to be equally disclosed with respect to use of human Desmoglein 1.

For proof of concept as to specificity and functionality, a 3$^{rd}$ generation self-inactivating lentiviral vector plasmid is useful, in which the expression is regulated under the human elongation factor 1 alpha promoter (e.g., pRRLSIN.cPPT.EF1a.Dsg3CAAR.WPRE). This results in stable (permanent) expression in the host T cell. As an alternative approach, the encoding mRNA can be electroporated into the host cell, which would achieve the same therapeutic effect as the virally transduced T cells, but would not be permanent, since the mRNA would dilute out with cell division.

In one aspect, the invention includes a vector comprising an isolated nucleic acid sequence encoding a chimeric autoantibody receptor (CAAR), wherein the isolated nucleic acid sequence comprises a human nucleic acid sequence of an extracellular domain comprising an autoantigen or fragment thereof, a nucleic acid sequence of a transmembrane domain, and a nucleic acid sequence of an intracellular signaling domain. In one embodiment, the vector comprises any of the isolated nucleic acid sequences encoding the CAAR as described herein. In another embodiment, the vector comprises a plasmid vector, viral vector, retrotransposon (e.g. piggyback, sleeping beauty), site directed insertion vector (e.g. CRISPR, zn finger nucleases, TALEN), or suicide expression vector, or other known vector in the art.

All constructs mentioned above comprising different autoantigens and fragments thereof are capable of use with 3rd generation lentiviral vector plasmids, other viral vectors, or RNA approved for use in human cells. In one embodiment, the vector is a viral vector, such as a lentiviral vector. In another embodiment, the vector is a RNA vector.

The production of the CAAR can be verified by sequencing. Expression of the full length CAAR protein may be verified using immunoblot, immunohistochemistry, flow cytometry or other technology well known and available in the art.

The present invention also provides a vector in which DNA encoding the CAAR of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

In brief summary, the expression of natural or synthetic nucleic acids encoding CAARs is typically achieved by operably linking a nucleic acid encoding the CAAR polypeptide or portions thereof to a promoter, and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid can be cloned into any number of different types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1α promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Biological methods for introducing a polynucleotide of interest into a host cell include the use of DNA and RNA vectors. RNA vectors include vectors having a RNA promoter and/other relevant domains for production of a RNA transcript. Viral vectors, and especially retroviral vectors, have become the most widely used method for inserting genes into mammalian, e.g., human cells. Other viral vectors may be derived from lentivirus, poxviruses, herpes simplex virus, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Cells Comprising the CAAR

In another aspect, the invention includes a genetically modified cell, such as a helper T cell, a cytotoxic T cell, a memory T cell, regulatory T cell, gamma delta T cell, a natural killer cell, cytokine induced killer cell, a cell line thereof, and other effector cell, comprises a chimeric autoantibody receptor (CAAR), wherein the CAAR comprises an extracellular domain comprising an autoantigen or fragment thereof, a transmembrane domain, and an intracellular signaling domain. In one embodiment, the genetically modified cell comprises the CAAR described herein.

In another embodiment, the cell expresses the CAAR. In this embodiment, the cell has high affinity for autoantibodies expressed on B cells. As a result, the cell can induce killing of B cells expressing the autoantibodies. In yet another embodiment, the cell has low affinity for antibodies bound to a Fc receptor.

In another embodiment, the genetically modified cell is a T cell. In this embodiment, the T cell expresses a Dsg3 CAAR. In this embodiment, the autoantigen comprises Dsg3 or a fragment thereof and the T cell has high affinity for Dsg3 autoantibodies expressed on B cells. As a result, the T cell can induce killing of B cells expressing Dsg3 autoantibodies. In yet another embodiment, the autoantigen comprises Dsg3 and the T cell has low affinity for Dsg3 antibodies bound to a Fc receptor.

It is also useful for the T cell to have limited toxicity toward healthy cells and specificity to cells expressing autoantibodies. Such specificity prevents or reduces off-target toxicity that is prevalent in current therapies that are not specific for autoantibodies. In one embodiment the T cell has limited toxicity toward healthy cells.

The invention includes T cells, such as primary cells, expanded T cells derived from primary T cells, T cells derived from stem cells differentiated in vitro, T cell lines such as Jurkat cells, other sources of T cells, combinations thereof, and other effector cells. For example, a transduced Jurkat cell line with a NFAT response element followed by GFP can be used to detect and isolate Dsg3 specific B cells and to clone the Dsg3 specific antibody repertoire in a comprehensive and unbiased fashion. The interacting B and Jurkat cells can be detected as GFP positive doublets and sorted by flow cytometry. Expression cloning of the B cell receptor encoding genes will provide further information on how autoimmunity and autoantibodies in pemphigus, such as pemphigus vulgaris, paraneoplastic pemphigus or pemphigus foliaceus, and other autoimmune diseases develop.

The functional ability of CAARs to bind to autoantibodies and sera, for example, but not limited to, pemphigus vulgaris sera, has been assessed in a Jurkat reporter cell line, which depends on activation of the CAAR by binding to autoantibody (in response to which the activated cells fluoresce green due to an NFAT-GFP reporter construct contained therein). Such methods are useful and reliable qualitative measures for functional binding ability. The proper processing of the autoantigen on the cell surface is also important and can be measured using monoclonal antibodies. For example, as described herein, a serial dilution of anti-Dsg3 hybridoma cells (AK23) showed a dose dependent response of the transduced Jurkat cells to the Dsg3 autoantibody displaying hybridoma and no activation by non-Dsg3 specific or healthy primary human B cells. Furthermore, primary T cells transduced with the CAAR demonstrate specific killing of AK23. Furthermore, truncations of Dsg3 based on major disease epitopes are also useful and included herein. Truncated versions using a smaller hinge region are also useful. With regard to safety, preventing or reducing possible hemophilic and heterophilic interactions and activation (e.g. Dsg3-Dsg3) between the transduced cells or toward keratinocytes is preferred.

Further assessment of efficacy and safety of the CAAR can be performed, for example, as follows:

Constructs can be transiently transfected into human cells, such as 293T/17. The surface expression can be detected with monoclonal antibodies (either IgG or ScFv) specific for the abovementioned extracellular domains 1, 2, 3, 4, 5, the linker between the domains, or other structure included in the CAAR. Binding can be verified with specific secondary antibodies and quantified by flow cytometry.

Production of membrane expressed constructs of human anti-desmoglein 3 antibodies of the IgM and IgG1 isotype is described herein, which are expressed in MHCI negative K562 cells (ATCC CCL-243). These cells can serve as target cells for testing the different Dsg3-CAARs.

The above mentioned the CAAR constructs are compatible with VSV-G pseudotyped HIV-1 derived lentiviral particles and can be permanently expressed in primary human T cells from healthy donors using lentiviral transduction. Killing efficacy can be determined in a chromium based cell lysis assay or any similar assay known in the art.

Additional target cell lines can be produced as needed by expression of human monoclonal antibodies on the surface of K562 cells.

A similar approach as above could be applied to desmoglein 1, against which antibodies are found in mucocutaneous forms of pemphigus vulgaris or pemphigus foliaceus. A similar approach can also be applied to the NC16A domain of BP180 (Type XVII collagen), which is the primary antigenic target of autoantibodies in bullous pemphigoid; the NC1 and NC2 domains of type VII collagen, which is targeted by autoantibodies in epidermolysis bullosa acquisita; or tissue tranglutaminase/gliadin peptide/epidermal transglutaminase, which are targeted by autoantibody complexes in celiac disease and dermatitis herpetiformis.

Autoimmune Diseases

The present invention also provides methods for preventing, treating and/or managing a disorder associated with autoantibody-expressing cells (e.g., an autoimmune disease). The methods comprise administering to a subject in need thereof a CAART cell of the invention that binds to the autoantibody-expressing cell. In one aspect, the subject is a human. Non-limiting examples of disorders associated with autoantibody-expressing cells include autoimmune disorders (such as pemphigus vulgaris, paraneoplastic pemphigus or pemphigus foliaceus).

The present invention also provides methods for preventing, treating and/or managing an autoimmune disease associated with autoantibody-expressing cells. The methods comprise administering to a subject in need a CAART cell of the invention that binds to the autoantibody-expressing cell. In one embodiment, the subject undergoes plasmapheresis or another clinical treatment to remove or decrease antibodies in the subject's serum. The method to remove or decrease serum antibodies, such as autoantibodies, may include chemical or other methods known in the art. The treatment method may be specific to the autoantibody or generalized for any antibody. In one embodiment, the subject is a human. Non-limiting examples of diseases associated with autoantibody-expressing cells include desmoglein 3 autoantibodies, and the like.

In the methods of treatment, T cells isolated from a subject can be modified to express the appropriate CAAR, expanded ex vivo and then reinfused into the subject. The modified T cells recognize target cells, such as Dsg3 specific B cells, and become activated, resulting in killing of the autoimmune target cells.

Relapse may also occur in patients with an autoimmune disease, for example in pemphigus patients. In patients treated with rituximab, the relapse may be mediated by persistence of the same autoantibody B cell clones, whereas remission is associated with disappearance of these clones. By infusing CAART cells, the autoimmune cells are depleted to induce long-term remission, possibly due to the longevity of the CAART cells and/or autoantigen-reactive clones do not re-appear (i.e. in pemphigus vulgaris, paraneoplastic pemphigus or pemphigus foliaceus, the break in tolerance is a one-time mistake).

To monitor CAAR-expressing cells in vitro, in situ, or in vivo, CAAR cells can further express a detectable marker. When the CAAR binds the target, the detectable marker is activated and expressed, which can be detected by assays known in the art, such as flow cytometry. In one embodiment, the Dsg3-CAAR includes a NFAT response element and a detectable marker, such as a green fluorescent protein (GFP), to detect and quantify Dsg3 CAAR expressing cells.

Sources of T Cells

Prior to expansion and genetic modification, T cells are obtained from a subject. Examples of subjects include humans, dogs, cats, mice, rats, and transgenic species thereof. T cells can be obtained from a number of sources, including skin, peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-$CD3$/anti-$CD28$ (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8$^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4$^+$ T cells express higher levels of CD28 and are more efficiently captured than CD8$^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to the beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-$\gamma$, IL-4, IL-7, GM-CSF, IL-10, IL-12, IL-15, TGF$\beta$, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one aspect, the invention includes a method for treating an autoimmune disease in a subject. The method comprises: administering to the subject an effective amount of a genetically modified T cell comprising an isolated nucleic acid sequence encoding a chimeric autoantibody receptor (CAAR), wherein the isolated nucleic acid sequence comprises a nucleic acid sequence of an extracellular domain comprising an autoantigen or fragment thereof, a nucleic acid sequence of a transmembrane domain, and a nucleic acid sequence of an intracellular signaling domain, thereby treating the autoimmune disease in the subject.

In one embodiment, the autoimmune disease is selected from pemphigus vulgaris paraneoplastic pemphigus, or pemphigus foliaceus. In another embodiment, the subject is a human.

Without wishing to be bound by any particular theory, the anti-autoantibody immune response elicited by the CAAR-modified T cells may be an active or a passive immune response. In yet another embodiment, the modified T cell targets a B cell. For example, autoantibody expressing B cells may be susceptible to indirect destruction by CAAR-redirected T cells that have previously reacted against adjacent autoantibody-expressing cells.

In one embodiment, the fully-human CAAR-genetically modified T cells of the invention may be a type of vaccine for ex vivo immunization and/or in vivo therapy in a mammal. In one embodiment, the mammal is a human.

With respect to ex vivo immunization, at least one of the following occurs in vitro prior to administering the cell into a mammal: i) expansion of the cells, ii) introducing a nucleic acid encoding a CAAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAAR disclosed herein. The CAAR-modified cell can be administered to a mammalian recipient to provide a therapeutic benefit. The mammalian recipient may be a human and the CAAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also includes compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAAR-modified T cells of the invention are used in the treatment of diseases, disorders and conditions associated with expression of autoantibodies. In certain embodiments, the cells of the invention are used in the treatment of patients at risk for developing autoimmune diseases, disorders and conditions associated with expression of autoantibodies. Thus, the present invention provides methods for the treatment or prevention of autoimmune diseases, disorders and conditions associated with expression of autoantibodies comprising administering to a subject in need thereof, a therapeutically effective amount of the CAAR-modified T cells of the invention.

The CAAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-autoantibody effective amount," "an autoimmune disease-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, activated T cells are administered to a subject. Subsequent to administration, blood is redrawn or apheresis is performed, and T cells are activated and expanded therefrom using the methods described here, and are then reinfused back into the patient. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

Administration of the cells of the invention may be carried out using any convenient means, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

CAAR Constructs

The desmoglein 3 (Dsg3) CAAR was cloned by PCR amplification from human cDNA with specific primers
  a) for the signal peptide of human CD8 alpha (fragment A) (forward: 5'CTAGCAGGATCCGCCAC-CATGGCCTTACCAGTGACCG (SEQ ID NO:17) (adding a Kozak sequence and a BamHI restriction site), reverse: 5' TCTATTCGCAAT-TCCGGCCTGGCGGCG (SEQ ID NO:18), overlapping into the propeptide of human Dsg3),
  b) the signal peptide of the human CD8 hinge and transmembrane region (fragment C) (forward: 5'CTCAGGGAGGAAGCCCAC-CACGACGCCAGCGCCGC (SEQ ID NO:19) (5' overlap from EC5 of human Dsg3), reverse: 5'CCCCGTTTGGTGATAACCAGTGACAG-GAGAAGG (SEQ ID NO:20) (5' overlap into the human CD137 signal transduction domain)),
  c) the human CD137 signal transduction domain (fragment D) (forward: 5'CTGGTTATCAC-CAAACGGGGCAGAAAGAAACTCC (SEQ ID NO:21), reverse: 5' TTCACTCTCAGTTCA-CATCCTCCTTCTTCTTCTTCTGG (SEQ ID NO:22) (overlapping into the human CD247 (aka CD3 zeta) signal transduction domain)),
  d) and the human CD3 zeta signal transduction domain (fragment E) (forward: 5'GATGTGAACTGAGAGT-GAAGTTCAGCAGGAGCGC (SEQ ID NO:23), reverse: 5' GGTTGATTGTCGACGCGGATCT-TAGCGAGGGGGC (SEQ ID NO:24) (adding a SalI site after the TAA stop codon)),
  e) for expression in a non-lentiviral vector plasmid the BamHI site was replaced with a XhoI site and the SalI site was replaced with a BamHI site.

The exon-encoding sequence of human Dsg3 (fragment B) was amplified from the plasmid DN653 (a gift from Prof. Amagai, Keio University, Tokyo, Japan) with the primers forward 5'CCAGGCCGGAATTGCGAATAGA-GACTAAAGG (SEQ ID NO:25) and reverse 5'CGTGGTGGGCTTCCTCCCTGAGTGCGGCC (SEQ ID NO:26), so that an overlap with the 5' located sequence of the signal peptide of CD8 and the 3' located CD8 hinge became possible.

After verification of the correct size of the PCR products, the fragments were purified (Promega wizard SV) and subjected to extension overlap PCRs, joining fragment A with B as well as C with D. The joined fragment CD was extended with another overlap-extension PCR with fragment E and finally the fragments AB and CDE were PCR-conjugated. All PCR reactions were performed with Q5 hot start polymerase (New England Biolabs) according to the manufacturer's recommendation. The final 2.5 kB long PCR product was subjected to a gel purification and digested either with BamHI-SalI (cloning into lentiviral vector plasmid) or XhoI-BamHI (cloning into non-lentiviral expression plasmid, namely pCEP4, life technologies).

To facilitate constitutive expression under a strong human promoter that is not prone to silencing in lymphoid cells, the Dsg3 CAAR was cloned into a 3rd generation HIV1-basedlentiviral vector plasmid, namely pRRLSIN-.cPPT.PGK-GFP.WPRE (addgene 12252). Since previous studies had shown a favorable expression under the EF1alpha compared to the PGK promoter, we PCR amplified the EF1alpha promoter from human genomic DNA using the primers forward 5'GGATCCTGCTAGACT-CACGACACCTGAAATGGAAG (SEQ ID NO:27) and reverse 5' GAGGAGGTCGACATTCGT-GAGGCTCCGGTGCCCGTC (SEQ ID NO:28). The PGK promoter was replaced with the EF1alpha promoter by digesting the PCR product with SalI and BamHI and the plasmid with XhoI and BamHI. The compatible ends of SalI and XhoI result in a deletion of the XhoI and SalI sites, so that the plasmid retains the unique BamHI and SalI sites flanking the GFP that was replaced with the Dsg3 CAAR by digestion and ligation.

Shortened versions of the Dsg3 CAAR were cloned into the same plasmid backbone using BamHI and SalI To facilitate high surface expression the shortened versions were codon optimized using a codon adaptation index-based algorithm (geneart, life technologies) and synthesized as double-stranded DNA fragments (geneart, life technologies). In these constructs the CD8 hinge region was replaced with an 13 amino acid long flexible GS-linker, providing a unique NheI site that could be used to insert different Dsg3 encoding fragments between the Kozak sequence (with BamHI) and the GS-linker (with NheI). The complete extracellular Dsg3 was cloned into this cloning site and from the derived plasmid various versions of Dsg3 were produced with the following primers:

```
BamHI-CD8 signal peptide-Dsg3EC1-5-NheI:
BamHI.CD8.for:
                                    (SEQ ID NO: 29)
GAGGAGGAGGGATCCGCCACC EC5.NheI.rev:
                                    (SEQ ID NO: 30)
CCTCCGCCGCCGCTAGCTCTGCC BamHI-CD8 signal peptide-Dsg3EC1-4-NheI
BamHI.CD8.for:
                                    (SEQ ID NO: 29)
GAGGAGGAGGGATCCGCCACC EC4.NheI.rev:
                                    (SEQ ID NO: 31)
CCTCCGCCGCCGCTAGCCTTTTCCAGCACGGCGG
```

-continued

BamHI-CD8 signal peptide-Dsg3EC1-3-NheI:
BamHI.CD8.for:
(SEQ ID NO: 29)
GAGGAGGAGGGATCCGCCACC EC3.NheI.rev:
(SEQ ID NO: 32)
TCTCCTCGCTAGCGAAGGCAATGCCC BamHI-CD8 signal peptide-Dsg3EC1-2-NheI:
BamHI.CD8.for:
(SEQ ID NO: 29)
GAGGAGGAGGGATCCGCCACC EC2.NheI.rev:
(SEQ ID NO: 33)
TCCGCCGCCGCTAGCCCGGAACATAGGGAAGTTGTCG In order to clone a CAAR that presents the EC2-3 of Dsg3, the EC3.NheI.rev primer was used in combination with a primer for the 5' sequence of the EC2 (5'AAGCGGCGGCAGAAACGCATCCTGGACAT-CAACGACAACC) (SEQ ID NO:34); the resulting EC2-3 sequence was PCR-conjugated with the CD8 signal peptide (previously amplified with the overlapping reverse primer 5' GATGCGTTTCTGCCGCCGCTTGGCCTGCTGCAT-TGTC (SEQ ID NO:35) and the BamHI.CD8 forward primer (see above)). The sequence of the complete EC1-5 CAAR construct is as follows:

(SEQ ID NO: 36)
ATGGCTCTGCCTGTGACAGCTCTGCTGCTGCCTCTGGCCCTGCTGCTGCA

TGTGCCAGACCTGGCTCCGAGCTGCGGATCGAGACAAAGGGCCAGTACGA

CGAGGAAGAGATGACAATGCAGCAGGCCAAGCGGCGGCAGAAACGCGAG

TGGGTCAAGTTCGCCAAGCCCTGCAGAGAGGGCGAGGACAACAGCAAGC

GGAACCCTATCGCCAAGATCACCAGCGACTACCAGGCCACCCAGAAGATC

ACCTACCGGATCAGCGGCGTGGGCATCGACCAGCCCCCTTTCGGCATCTT

CGTGGTGGACAAGAACACCGGCGACATCAACATCACCGCCATCGTGGACA

GAGAGGAAACCCCCAGCTTCCTGATCACCTGTCGGGCCCTGAATGCCCAG

GGCCTGGACGTGGAAAAGCCCCTGATCCTGACCGTGAAGATCCTGGACAT

CAACGACAACCCCCCCGTGTTCAGCCAGCAGATCTTCATGGGCGAGATCG

AGGAAAACAGCGCCAGCAACAGCCTCGTGATGATCCTGAACGCCACCGA

CGCCGACGAGCCCAACCACCTGAATAGCAAGATCGCCTTCAAGATCGTGT

CCCAGGAACCCGCCGGAACCCCCATGTTCCTGCTGAGCAGAAATACCGGC

GAAGTGCGGACCCTGACCAACAGCCTGGATAGAGAGCAGGCCAGCAGCT

ACCGGCTGGTGGTGTCTGGCGCTGACAAGGATGGCGAGGGCCTGAGCACA

CAGTGCGAGTGCAACATCAAAGTGAAGGACGTGAACGACAACTTCCCTAT

GTTCCGGGACAGCCAGTACAGCGCCCGGATCGAAGAGAACATCCTGAGC

AGCGAGCTGCTGCGGTTCCAAGTGACCGACCTGGACGAAGAGTACACCGA

CAACTGGCTAGCCGTGTACTTCTTCACCAGCGGCAACGAGGGCAATTGGT

TCGAGATCCAGACCGACCCCCGGACCAATGAGGGCATCCTGAAGGTCGTG

AAGGCCCTGGACTACGAGCAGCTGCAGAGCGTGAAGCTGTCTATCGCCGT

GAAGAACAAGGCCGAGTTCCACCAGTCCGTGATCAGCCGGTACAGAGTGC

AGAGCACCCCCGTGACCATCCAAGTGATCAACGTGCGCGAGGGCATTGCC

-continued

TTCAGACCCGCCAGCAAGACCTTCACCGTGCAGAAGGGCATCAGCAGCAA

GAAACTGGTGGACTACATCCTGGGCACCTATCAGGCCATCGACGAGGACA

CCAACAAAGCCGCCTCCAACGTGAAATACGTGATGGGCCGGAACGACGG

CGGCTACCTGATGATCGATTCCAAGACCGCCGAGATCAAGTTCGTGAAGA

ATATGAACCGGGACTCCACCTTCATCGTGAACAAGACCATCACAGCCGAG

GTGCTGGCCATCGATGAGTATACCGGCAAGACCAGCACCGGCACCGTGTA

CGTGCGGGTGCCCGACTTCAACGATAACTGCCCTACCGCCGTGCTGGAAA

AGGACGCCGTGTGTAGCAGCAGCCCCAGCGTGGTGGTGTCCGCCAGAACC

CTGAACAACCGGTACACCGGCCCCTACACCTTCGCCCTGGAAGATCAGCC

TGTGAAGCTGCC

CGCCGTGTGGTCCATCACCACACTGAATGCCACCAGCGCCCTGCTGAGAG

CCCAGGAACAGATTCCCCCTGGCGTGTACCACATCAGCCTGGTGCTGACC

GACAGCCAGAACAACAGATGCGAGATGCCCCGGTCCCTGACCCTGGAAGT

GTGCCAGTGCGACAACAGAGGCATCTGCGGCACCAGCTACCCTACCACCT

CTCCCGGCACCAGATACGGCAGACCTCACAGCGGCAGAGCTAGCGGCGG

CGGAGGAAGCGGAGGCGGAGGATCTAGCGGCATCTACATCTGGGCCCCTC

TGGCCGGAACATGCGGAGTGCTGCTGCTGAGCCTCGTGATCACCCTGTAC

TGCAAGAGAGGCCGGAAGAAGCTGCTGTACATCTTCAAGCAGCCCTTCAT

GCGGCCCGTGCAGACCACCCAGGAAGAGGACGGCTGCAGCTGTCGGTTCC

CCGAGGAAGAAGAAGGCGGCTGCGAACTGAGAGTGAAGTTCAGCAGAAG

CGCCGACGCCCCTGCCTACCAGCAGGGACAGAACCAGCTGTACAACGAGC

TGAACCTGGGCAGACGGGAAGAGTACGACGTGCTGGACAAGCGGAGAGG

CAGGGACCCTGAGATGGGCGGCAAGCCCAGAAGAAAGAACCCCCAGGAA

GGCCTGTATAACGAACTGCAGAAAGACAAGATGGCCGAGGCCTACAGCG

AGATCGGAATGAAGGGCGAGCGGAGAAGAGGCAAGGGCCACGACGGACT

GTACCAGGGACTGAGCACCGCCACCAAGGACACCTACGACGCCCTGCACA

TGCAGGCCCTGCCCCCTAGATAA.

The desmoglein 1 (Dsg1) CAAR was cloned by PCR amplification from human cDNA using specific primers The Sequence of the Complete CAAR Construct is as Follows:
Dsg1 CAAR EC1-3 nucleotide sequence (extracellular portion up to GS-linker, transmembrane and cytoplasmic domains same as for Dsg3 CAAR)

(SEQ ID NO: 37)
ATGGCACTTCCAGTGACCGCTCTGCTCCTGCCACTGGCCCTGCTGCTCCAC

GCTGCCCGCCCGGGCAGCGAGTTCAGGATCCAAGTCAGGGATTATAATAC

TAAAAACGGTACCATCAAGTGGCATTCCATACGCAGGCAGAAAAGGGAG

TGGATTAAGTTTGCTGCCGCGTGCCGGGAGGGTGAAGACAATAGCAAACG

GAATCCCATTGCAAAGATACATAGCGATTGCGCTGCCAATCAGCAGGTTA

CATATCGAATCTCCGGCGTGGGGATTGACCAGCCTCCTTATGGCATTTTCG

TCATTAACCAAAGACTGGCGAGATAAATATCACATCAATTGTGGACCGG

GAAGTGACGCCGTTTTTTATCATCTACTGTAGAGCTCTGAACTCCATGGGC

-continued

```
CAGGATCTGGAAAGGCCACTGGAGCTGAGGGTCAGGGTCCTTGACATCAA

TGACAATCCCCCCGTCTTTTCCATGGCCACGTTCGCCGGACAGATTGAGGA

AAATAGCAATGCCAATACACTGGTGATGATCCTGAACGCTACCGACGCTG

ACGAGCCGAATAATCTGAACAGTAAAATTGCTTTTAAGATCATTCGGCAG

GAGCCATCAGACAGCCCAATGTTTATCATTAACAGAAACACCGGAGAGAT

CCGCACAATGAACAATTTCCTGGATAGGGAACAGTATGGACAGTATGCAC

TCGCTGTTCGGGGCTCCGACCGGGACGGTGGAGCTGATGGCATGAGTGCC

GAGTGCGAGTGCAATATCAAGATACTCGACGTAAATGATAATATTCCATA

CATGGAACAGAGCTCTTACACTATCGAGATCCAGGAGAATACTCTCAACT

CTAATCTTCTTGAAATTAGAGTGATTGATCTCGACGAGGAATTTTCTGCCA

ATTGGATGGCTGTCATCTTCTTTATTAGTGGTAACGAGGGTAACTGGTTCG

AGATAGAAATGAATGAAAGGACAAATGTGGGAATCTTGAAGGTGGTTAA

ACCACTGGACTACGAAGCAATGCAATCACTCCAGCTGTCAATAGGCGTCA

GAAATAAGGCGGAGTTCCATCACTCCATTATGTCCCAGTATAAATTGAAA

GCCAGTGCCATAAGCGTAACCGTGTTGAACGTGATAGAAGGGCCTGTTTT

TGCATCCGGA
```

Dsg1 CAAR EC1-3 amino acid sequence (extracellular portion up to GS-linker, transmembrane and cytoplasmic domains same as for Dsg3 CAAR)

(SEQ ID NO: 38)
```
MALPVTALLLPLALLLHAARPGSEFRIQVRDYNTKNGTIKWHSIRRQKRE

WIKFAAACREGEDNSKRNPIAKIHSDCAANQQVTYRISGVGIDQPPYGIF

VINQKTGEINITSIVDREVTPFFITYCRALNSMGQDLERPLELRVRVLDI

NDNPPVFSMATFAGQIEENSNANTLVMILNATDADEPNNLNSKIAFKIIR

QEPSDSPMFIINRNTGEIRTMNNFLDREQYGQYALAVRGSDRDGGADGMS

AECECNIKILDVNDNIPYMEQSSYTIEIQENTLNSNLLEIRVIDLDEEFS

ANWMAVIFFISGNEGNAVFEIEMNERTNVGILKVVKPLDYEAMQSLQLSI

GVRNKAEFHHSIMSQYKLKASAISVTVLNVIEGPVFASG
```

Dsg1 CAAR EC1-4 nucleotide sequence (extracellular portion up to GS-linker, transmembrane and cytoplasmic domains same as for Dsg3 CAAR)

(SEQ ID NO: 39)
```
ATGGCACTTCCAGTGACCGCTCTGCTCCTGCCACTGGCCCTGCTGCTCCAC

GCTGCCCGCCCGGGCAGCGAGTTCAGGATCCAAGTCAGGGATTATAATAC

TAAAAACGGTACCATCAAGTGGCATTCCATACGCAGGCAGAAAAGGGAG

TGGATTAAGTTTGCTGCCGCGTGCCGGAGGGTGAAGACAATAGCAAACG

GAATCCCATTGCAAAGATACATAGCGATTGCGCTGCCAATCAGCAGGTTA

CATATCGAATCTCCGGCGTGGGGATTGACCAGCCTCCTTATGGCATTTTCG

TCATTAACCAAAAGACTGGCGAGATAAATATCACATCAATTGTGGACCGG

GAAGTGACGCCGTTTTTTATCATCTACTGTAGAGCTCTGAACTCCATGGC

CAGGATCTGGAAAGGCCACTGGAGCTGAGGGTCAGGGTCCTTGACATCAA

TGACAATCCCCCCGTCTTTTCCATGGCCACGTTCGCCGGACAGATTGAGGA

AAATAGCAATGCCAATACACTGGTGATGATCCTGAACGCTACCGACGCTG

ACGAGCCGAATAATCTGAACAGTAAAATTGCTTTTAAGATCATTCGGCAG

GAGCCATCAGACAGCCCAATGTTTATCATTAACAGAAACACCGGAGAGAT

CCGCACAATGAACAATTTCCTGGATAGGGAACAGTATGGACAGTATGCAC

TCGCTGTTCGGGGCTCCGACCGGGACGGTGGAGCTGATGGCATGAGTGCC

GAGTGCGAGTGCAATATCAAGATACTCGACGTAAATGATAATATTCCATA

CATGGAACAGAGCTCTTACACTATCGAGATCCAGGAGAATACTCTCAACT

CTAATCTTCTTGAAATTAGAGTGATTGATCTCGACGAGGAATTTTCTGCCA

ATTGGATGGCTGTCATCTTCTTTATTAGTGGTAACGAGGGTAACTGGTTCG

AGATAGAAATGAATGAAAGGACAAATGTGGGAATCTTGAAGGTGGTTAA

ACCACTGGACTACGAAGCAATGCAATCACTCCAGCTGTCAATAGGCGTCA

GAAATAAGGCGGAGTTCCATCACTCCATTATGTCCCAGTATAAATTGAAA

GCCAGTGCCATAAGCGTAACCGTGTTGAACGTGATAGAAGGGCCTGTTTT

TCGCCCTGGGTCCAAAACCTACGTTGTGACAGGAAACATGGGATCCAACG

ACAAAGTCGGCGACTTCGTCGCAACAGACCTGGACACCGGTCGCCCTTCC

ACAACTGTGCGGTACGTGATGGGAAACAATCCAGCCGACTTGTTGGCAGT

CGATAGCAGGACAGGGAAGCTGACCCTTAAAAACAAGGTTACAAAAGAA

CAATATAACATGCTGGGCGGCAAATATCAGGGAACCATTTTGTCAATCGA

CGACAACCTGCAGCGCACGTGCACGGGGACGATCAACATCAACATCCAG

AGCTTTGGGAATGACGATAGAACCAACACAGAGCCCAACGCTAGCGGA
```

Dsg1 CAAR EC1-4 amino acid sequence (extracellular portion up to GS-linker, transmembrane and cytoplasmic domains same as for Dsg3 CAAR)

(SEQ ID NO: 40)
```
MALPVTALLLPLALLLHAARPGSEFRIQVRDYNTKNGTIKWHSIRRQKRE

WIKFAAACREGEDNSKRNPIAKIHSDCAANQQVTYRISGVGIDQPPYGIF

VINQKTGEINITSIVDREVTPFFIIYCRALNSMGQDLERPLELRVRVLDI

NDNPPVFSMATFAGQIEENSNANTLVMILNATDADEPNNLNSKIAFKIIR

QEPSDSPMFIINRNTGEIRTMNNFLDREQYGQYALAVRGSDRDGGADGMS

AECECNIKILDVNDNIPYMEQSSYTIEIQENTLNSNLLEIRVIDLDEEFS

ANWMAVIFFISGNEGNWFEIEMNERTNVGILKVVKPLDYEAMQSLQLSIG

VRNKAEFHHSIMSQYKLKASAISVTVLNVIEGPVFRPGSKTYVVTGNMGS

NDKVGDFVATDLDTGRPSTTVRYVMGNNPADLLAVDSRTGKLTLKNKVTK

EQYNMLGGKYQGTILSIDDNLQRTCTGTININIQSFGNDDRTNTEPNASG
```

Dsg1 CAAR EC1-5 nucleotide sequence (extracellular portion up to GS-linker, transmembrane and cytoplasmic domains same as for Dsg3 CAAR)

(SEQ ID NO: 41)
```
GAAGAAGAAGGGTCAGCCACTATGGCACTTCCAGTGACCGCTCTGCTCCT

GCCACTGGCCCTGCTGCTCCACGCTGCCCGCCCGGGCAGCGAGTTCAGGA

TCCAAGTCAGGGATTATAATACTAAAAACGGTACCATCAAGTGGCATTCC
```

```
ATACGCAGGCAGAAAAGGGAGTGGATTAAGTTTGCTGCCGCGTGCCGGGA

GGGTGAAGACAATAGCAAACGGAATCCCATTGCAAAGATACATAGCGATT

GCGCTGCCAATCAGCAGGTTACATATCGAATCTCCGGCGTGGGGATTGAC

CAGCCTCCTTATGGCATTTTCGTCATTAACCAAAAGACTGGCGAGATAAAT

ATCACATCAATTGTGGACCGGGAAGTGACGCCGTTTTTTATCATCTACTGT

AGAGCTCTGAACTCCATGGGCCAGGATCTGGAAAGGCCACTGGAGCTGAG

GGTCAGGGTCCTTGACATCAATGACAATCCCCCCGTCTTTTCCATGGCCAC

GTTCGCCGGACAGATTGAGGAAAATAGCAATGCCAATACACTGGTGATGA

TCCTGAACGCTACCGACGCTGACGAGCCGAATAATCTGAACAGTAAAATT

GCTTTTAAGATCATTCGGCAGGAGCCATCAGACAGCCCAATGTTTATCATT

AACAGAAACACCGGAGAGATCCGCACAATGAACAATTTCCTGGATAGGG

AACAGTATGGACAGTATGCACTCGCTGTTCGGGGCTCCGACCGGGACGGT

GGAGCTGATGGCATGAGTGCCGAGTGCGAGTGCAATATCAAGATACTCGA

CGTAAATGATAATATTCCATACATGGAACAGAGCTCTTACACTATCGAGA

TCCAGGAGAATACTCTCAACTCTAATCTTCTTGAAATTAGAGTGATTGATC

TCGACGAGGAATTTTCTGCCAATTGGATGGCTGTCATCTTCTTTATTAGTG

GTAACGAGGGTAACTGGTTCGAGATAGAAATGAATGAAAGGACAAATGT

GGGAATCTTGAAGGTGGTTAAACCACTGGACTACGAAGCAATGCAATCAC

TCCAGCTGTCAATAGGCGTCAGAAATAAGGCGGAGTTCCATCACTCCATT

ATGTCCCAGTATAAATTGAAAGCCAGTGCCATAAGCGTAACCGTGTTGAA

CGTGATAGAAGGGCCTGTTTTTCGCCCTGGGTCCAAAACCTACGTTGTGAC

AGGAAACATGGGATCCAACGACAAAGTCGGCGACTTCGTCGCAACAGAC

CTGGACACCGGTCGCCCTTCCACAACTGTGCGGTACGTGATGGGAAACAA

TCCAGCCGACTTGTTGGCAGTCGATAGCAGGACAGGGAAGCTGACCCTTA

AAAACAAGGTTACAAAAGAACAATATAACATGCTGGGCGGCAAATATCA

GGGAACCATTTTGTCAATCGACGACAACCTGCAGCGCACGTGCACGGGGA

CGATCAACATCAACATCCAGAGCTTTGGGAATGACGATAGAACCAACACA

GAGCCCAACACAAAGATCACCACCAATACTGGCCGACAAGAATCCACCTC

CAGCACAAACTATGATACGTCCACTACCAGTACAGACTCCAGTCAGGTTT

ACAGCAGTGAACCCGGTAATGGTGCCAAGGATCTCCTGAGTGATAATGTT

CATTTTGGACCCGCTAGCGGA
```

Dsg1 CAAR EC1-5 amino acid sequence (extracellular portion up to GS-linker, transmembrane and cytoplasmic domains same as for Dsg3 CAAR)

(SEQ ID NO: 42)
```
MALPVTALLLPLALLLHAARPGSEFRIQVRDYNTKNGTIKWHSIRRQKRE

WIKFAAACREGEDNSKRNPIAKIHSDCAANQQVTYRISGVGIDQPPYGIF

VINQKTGEINITSIVDREVTPFFIIYCRALNSMGQDLERPLELRVRVLDI

NDNPPVFSMATFAGQIEENSNANTLVMILNATDADEPNNLNSKIAFKIIR

QEPSDSPMFIINRNTGEIRTMNNFLDREQYGQYALAVRGSDRDGGADGMS

AECECNIKILDVNDNIPYMEQSSYTIEIQENTLNSNLLEIRVIDLDEEFS

ANWMAVIFFISGNEGNAVFEIEMNERTNVGILKVVKPLDYEAMQSLQLSI

GVRNKAEFHHSIMSQYKLKASAISVTVLNVIEGPVFRPGSKTYVVTGNMG

SNDKVGDFVATDLDTGRPSTTVRYVMGNNPADLLAVDSRTGKLTLKNKVT

KEQYNMLGGKYQGTILSIDDNLQRTCTGTININIQSFGNDDRTNTEPNTK

ITTNTGRQESTSSTNYDTSTTSTDSSQVYSSEPGNGAKDLLSDNVHFGPA

SG
```

The presence of the construct encoding sequences in the plasmids were confirmed by digestion with SalI and BamHI. All constructs were verified by Sanger sequencing and the plasmids were purified in larger scale with removal of endotoxins (qiagen endofree maxiprep).

Transient Expression

To test the expression of the CAAR constructs, 293T/17 cells were transiently transfected using Polyethylenimine (PEI, jetPEI, polyplus) at a DNA:PEI ratio of 1:2. Expression was validated by flow cytometry with anti-Dsg3 EC1-IgG1 (clone: Px43) and anti-human Fc-PE (clone HP6017) after 36 hours on a LSRII flow cytometer (BD).

Production of HIV-1 Based Self-Inactivating Lentivirus

To facilitate stable expression of the CAAR constructs, VSV-G pseudotyped lentiviral particles were produced using a 3rd generation packaging system. Briefly, 293T/17 cells (ATCC CRL-11268) were transfected at a confluency of 90% with a mixture of the pRRLSIN.cPPT.EF1a-Dsg3CAAR. WPRE plasmid, the envelope plasmid pMD2.G (addgene 12252), the packaging plasmids pRSVRev (addgene 12253) and pMDLgm/pRRE (addgene 12251) in a complex with Lipofectamine2000 (life technologies). Lentivirus containing supernatant was harvested after 24, 48 and 72 hours, filtered through a 0.4 micrometer membrane, concentrated at 12000 g for 12 hours at 4° C. and stored at −80° C. until further usage.

Reporter Assay with NFAT-GFP Jurkat T Cells

Jurkat cells were cultured at 37° C. with 5% CO2 in a completely humidified environment using RPMI1640, HEPES 10 mM, Penicillin/Streptomycin 1% and FBS at 10%. Hybridoma medium was additionally supplemented with 1% non-essential amino acids, 1% sodium pyruvate and 0.5 mM BME. To test signal transduction by CAAR-target interaction, the CAAR constructs were expressed in a Jurkat reporter cell line that has been selected (G418) for stable expression of GFP controlled under an NFAT response element, facilitating GFP expression after CAAR engagement and PLCgamma and IP3 mediated intracellular calcium release. The Jurkat cell line was provided by Arthur Weiss (UCSF). Jurkat cells were transduced with CAAR lentivirus at a multiplicity of infection of 5-10 and expression of the CAAR construct was validated after >72 hours with anti-EC5-Dsg3 mouse IgG1 (clone: 5G11) and anti-mouse IgG1-APC (clone: A85-1, BD Pharmingen) by flow cytometry. To create target structures, tosylactivated dynabeads (life technologies) were loaded with monoclonal human or mouse IgG1 specifc for Dsg3 or with mesothelin (negative control) according to the manufacturer's recommendations. Additionally, serum from a PV patient and a non-PV individual were loaded onto beads. The AK23 hybridoma cell line (U.S. Pat. No. 7,550,562 B2) served as cellular target that secretes anti-Dsg3 antibodies and is surface-positive for these antibodies. As negative control we used another hybridoma cell line that secretes antibodies against the human VH3-15 framework region (BK-2; U.S.

Pat. No. 5,738,847 A) For characterization of CAAR-target interaction, the CAAR Jurkat cells were incubated for 4 hours with either beads at a bead:cell ratio of 3:1 or target cells at increasing concentration at 37° C. GFP expression was validated by flow cytometry. In addition to the beads and target cells, human B cells from a non-PV individual and primary human keratinocytes (provided by the SDRC, core B, University of Pennsylvania) were used to test for off-target effects.

Stimulation and Expansion of Primary Human T Cells

Primary human T cells were cultured in RPMI1640, 10% FBS and 10 mM HEPES, supplemented with 1% penicillin/streptomycin. T cells were isolated from voluntary healthy donors and provided by the human immunology core (University of Pennsylvania). Bulk T cells (CD4+ and CD8+) were stimulated with anti-CD3 and anti-CD28 beads (dynabeads, life technologies) at a bead:cell ratio of 3:1. When only CD8 cells were used, the culture medium was supplemented with 150-300 IU/ml IL2. 24 hours after stimulation, $10^6$ T cells were transduced with the CAAR constructs or a mock control at a MOI of 5-10. As mock control we used an scFv-based chimeric antigen receptor against human CD19 or human mesothelin. Expansion of the T cells was monitored for 8-14 days with analysis of cell density and cell volume every 2nd day for the first 6 days, after that daily. Cell volume and cell density was analyzed with a Coulter-Counter (Beckman Coulter). Killing assays were performed at a cell volume of ~400fl. Cell surface expression of the CAAR constructs was validated by flow cytometry using anti-Dsg3 antibodies (clones: Px43 (IgG1), Px44 (IgG1), F779 (scFv), AK23 (mouse IgG1)) and detection antibodies against human IgG-FC (clone: HP6017), mouse IgG1 (clone: A85-1) or HA peptide (clone: 3F10). ScFv-based chimeric antigen receptors were detected with polyclonal donkey anti-human IgG (heavy and light chain) or goat anti-mouse IgG.

In Vitro Killing Assay

In vitro killing was tested with a 51Cr-release assay. $5\times10^5$ target cells were loaded with 50 microCi of Na2 51CrO4 (Perkin Elmer) for 90 minutes, washed twice and resuspended in phenolred-free medium with 5% FBS. CAAR or mock transduced T cells were coincubated with loaded target cells for 4 and 24 hours at various effector:target ratios and chromium release into the supernatant was measured with a microbeta 2 plate counter (Perkin Elmer). When only CD8 cells were used, the assay was performed in presence of 75 IU/ml IL2. Spontaneous release by target cells only was analyzed in the same volume and maximum release was assessed by treating target cells with SDS at a final concentration of 2.5%. To test redirected, Fc-receptor mediated lysis, K562 cells positive for CD32 were incubated with CAAR T cells in the presence of human monoclonal anti-Dsg3 IgG1 (clone: PV2B7) at a concentration of 5 micrograms/ml or anti-human CD3 (okt3) at the same concentration.

Specific lysis was analyzed as follows:

Percent Specific Lysis: [(Experimental Release−Spontaneous Release)/(Maximum Release−Spontaneous Release)]*100

In Vivo Efficacy Testing of CAAR T Cells

CAAR or control-CAR transduced T cells were expanded as described herein. For in vivo experiments, CAAR or control-CAR T cells were adjusted to a concentration of $3\times10^7$ cells/ml and mixed with GFP-clickbeetle red or green transduced AK18, 19 or 23 hyrbidoma cells (at $10^6$ cells/ml), resulting in a T cell to target ratio of 30. Cells were kept on ice and 200 μl of the cell mixture was injected into the tail vein of NSG mice, resulting in $3\times10^6$ T cells and $10^5$ target cells per mouse. After i.v. injection, NSG mice were injected with D-Luciferin monopotassium salt solution at a dose of 300 mg/kg body weight.

Bioluminescence was quantified with a PerkinElmer IVIS spectrum preclinical in vivo imaging system. Additonal assessment of tumor burden by bioluminescence was done on day 3, 7, 13, 17/18, 26 and 35 after injection. Analysis was done with LivingImage software 4.4. For analysis, rectangle-shaped regions of interests with identical areas were set up from the head of the mouse to the middle the tail. Total flux in photons/second was calculated after background luminescence subtraction. A bioluminescence of $10^8$ photons/second was used to declare the mice dead, since this represented a ~100 fold expansion of the initial tumor burden and indicated loss of tumor control.

Mice were sacrificed in accordance to an approved IACUC protocol. Spleen and bone marrow samples were kept in RPMI medium supplemented with 10% FBS until further processing. Blood samples from sacrificed mice were obtained by cardiac puncture and anticoagulated with EDTA. Single cell suspension from spleen and flushed bone marrow samples were obtained by passing cells through a 100 um cell strainer. $10^6$ Cells were stained with anti-human CD3 (clone Okt3), anti-human CD45 (clones HI30 or 2D1) and anti-human Dsg3 (clone Px44, no loss of binding by EDTA denaturation) for 25 minutes at room temperature, fixed with BD Facs Lyse stored at 4 degrees Celsius and analyzed on a BD LSRII flow cytometer.

The results of the experiments are now described.

Pemphigus vulgaris (PV) is an antibody mediated autoimmune disease causing potentially fatal blistering of the skin and mucous membranes. It is a potentially life threatening due to malnutrition, infection, and dehydration. PV is a model tissue-specific, antibody-mediated autoimmune disease because the autoantigen Dsg3 (desmoglein 3) is well-defined and anti-desmoglein antibodies are necessary and sufficient to cause characteristic suprabasal blisters in animal and human skin models.

Autoantibodies are synthesized and secreted by autoreactive B lymphocytes and primarily target the extracellular EC1-3 domains of Dsg3 where trans- and cis-adhesive residues are located. The most effective treatment strategies in PV target B lymphocytes and include systemic corticosteroids, azathrioprine, mycophenolate mofetil, and cyclophosphamide to inhibit lymphocyte proliferation. Rituximab is used as an anti-CD20 B cell depletion mechanism via a B lymphocyte specific surface molecule. However, there is no treatment that targets only autoreactive cells as opposed to all B cells. This results in current treatment strategies having severe side effects, including fatal infection and secondary cancers.

Recently, genetically engineered T cells expressing a chimeric antigen receptor (CAR) against the B cell surface marker CD19 (DL Porter et al, NEJM 2011; SA Grupp et al, NEJM 2013) has been found to specifically target and kill CD19+ B cells and can induce long-lasting remission in patients with refractory B-cell malignancies.

As described herein, T cells can be engineered to kill target cells independent of MHC and co-stimulatory signals by expressing a recombinant chimeric T cell antigen receptor with an extracellular domain that specifically recognizes the target antigen, and an intracellular domain that is sufficient to activate signaling after antigen binding (Chimeric Antigen Receptors, or CARs). Chimeric Antigen Receptors consist of customized cell surface receptor (typically an antibody against a specific cell surface molecule on the target cell), transmembrane domain and intracellular domains of costimulatory signaling receptors in the same protein.

The advantages of using CARs include the ability to be directed against virtually all known antigens, CARs act independently of MHC expression of the target cell, and CAR binding to its target antigen results in activation of the T cell independently of costimulatory signals from the target cell. Engineering T cells for PV treatment relies on the perfect target for a genetically engineered T cell that is shared among all target cells, as well as unique to the target cell. For example, autoreactive B cells in PV express a surface Ig that binds to desmoglein 3.

The design for the genetically engineered T cells for PV optimally includes a typical chimeric antigen receptor (CAR) with a high affinity antibody binding moiety that targets specific autoantibodies. In autoimmune diseases such as PV, the pathogenic cells (B cells) already express the high affinity autoantibody on their cell surface. Thus, genetically engineered T cells for autoantibody-mediated diseases should express the antigen, not the antibody, on its cell surface=a chimeric autoantibody receptor (CAAR). In the case of PV, this is Dsg3.

Figure 2:
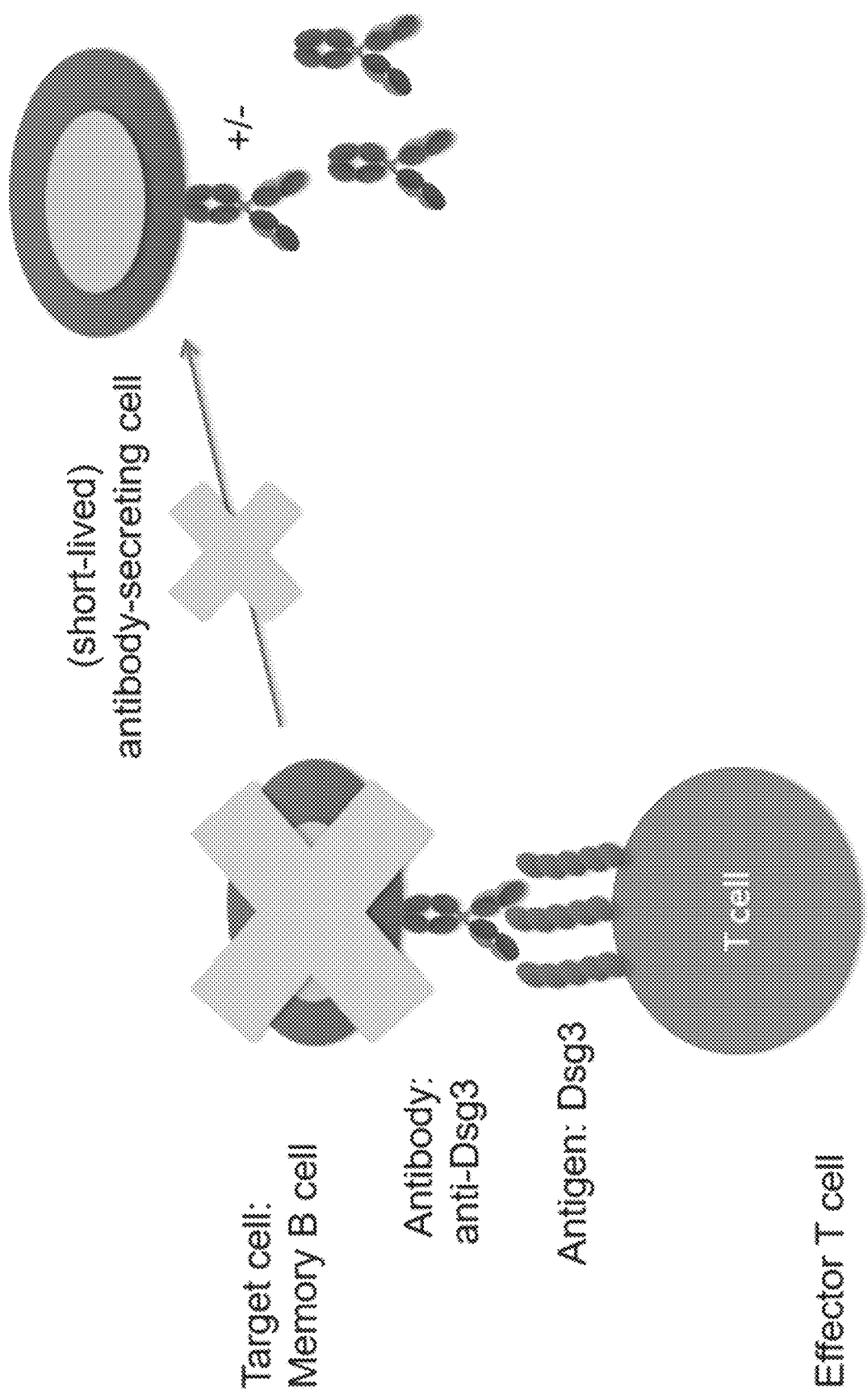
FIG. 2 is an illustration showing that engineered chimeric T cell receptors target Dsg3 specific B cells.
Figure 3:
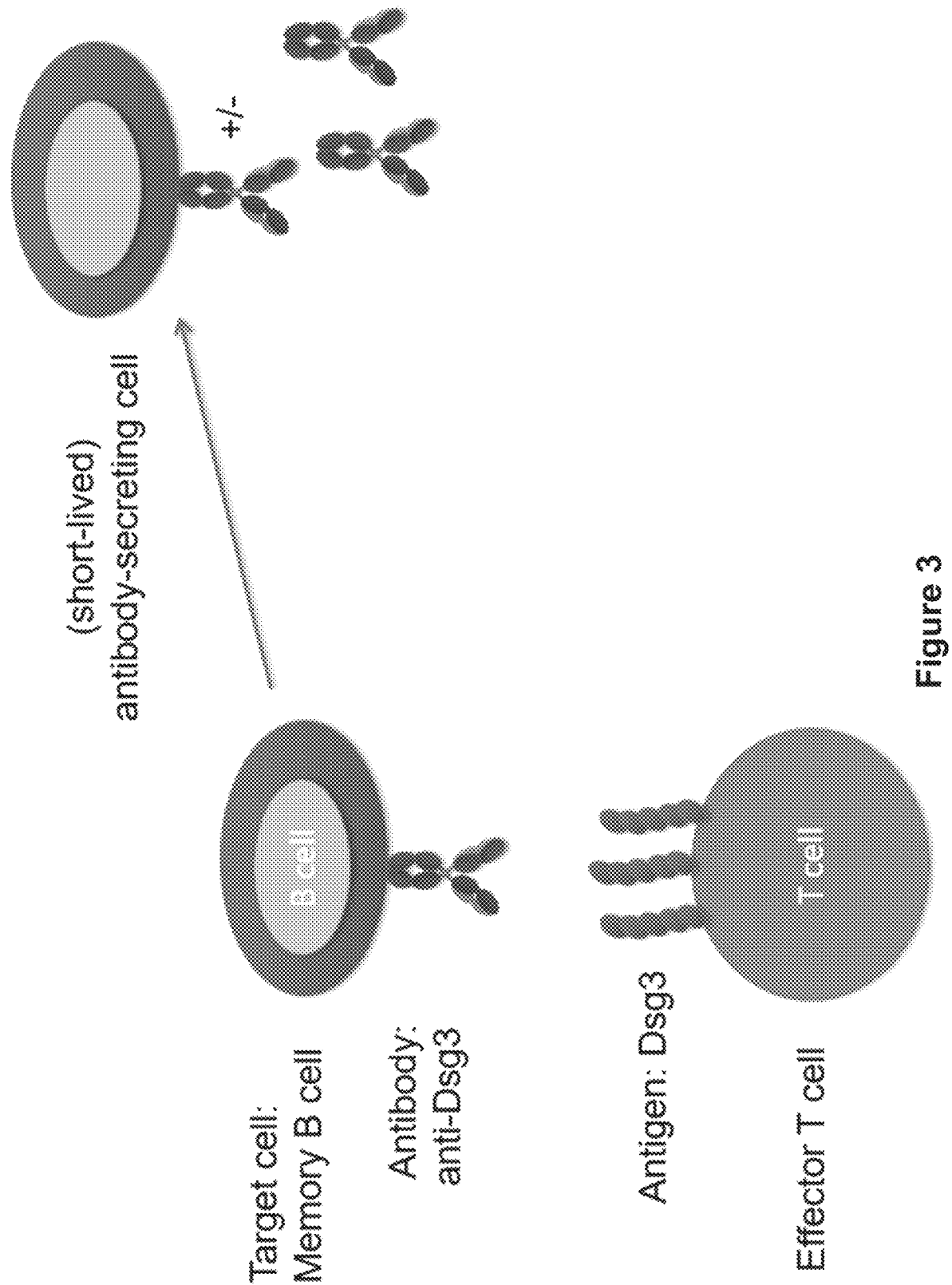
FIG. 3 is an illustration showing targeting of Dsg specific memory B cells and removing short-lived antibody-secreting B cells.

FIG. 1 is a schematic drawing that depicts how the proposed chimeric autoantibody receptor (CAAR) is distinct from all previously developed technologies. The left half of the figure shows a chimeric antigen receptor (CAR) on an effector cell to (the patient's own T cells), which targets an antigen (CD19) that is specifically expressed on the B cell lymphoma. What makes PV autoreactive B cells unique from all other B cells is that they express an autoantibody on their cell surface that is specific for the disease autoantigen, desmoglein 3 (Dsg3). Hence, the PV CAAR is the autoantigen (Dsg3), which targets the Dsg3-autoantibody expressed on the surface of autoreactive PV B cells. FIG. 2 illustrates that the interaction between engineered chimeric T cell receptors and target Dsg3 specific B cells is more specific for PV than CD19- or CD20-targeted therapies. Unlike a CD19- or CD20-targeted therapy, a generalized immune suppression should not occur with a Dsg3 targeted therapy. Engineered T cells are more sustainable than monoclonal antibody-based therapy because T cells proliferate in response to antigen and form memory T cells. Moreover, engineered chimeric T cell receptors that target Dsg specific B cells remove both memory and short-lived antibody-secreting B cells (FIG. 3).

Figure 4:
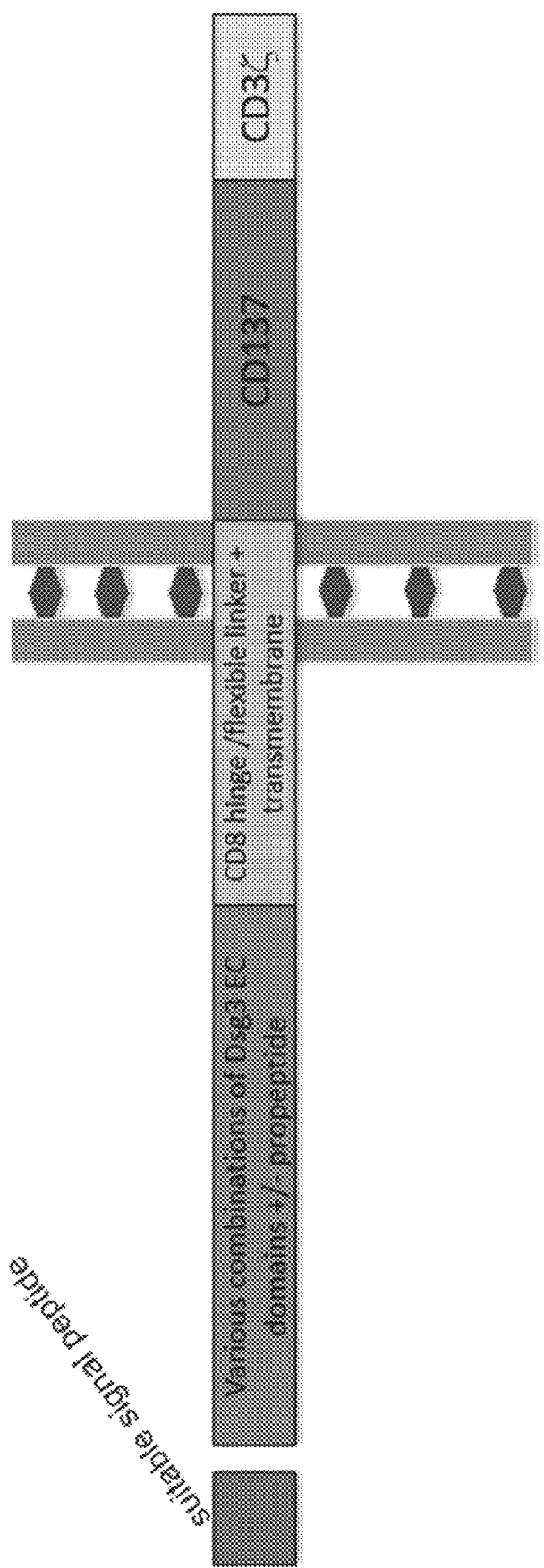
FIG. 4 is a schematic drawing of the protein domains comprising a desmoglein 3 (Dsg3) chimeric autoantibody receptor (CAAR).

Desmogleins are ideal autoantigens for a chimeric autoantibody receptor (CAAR) because they consist of modular extracellular domains that can be truncated. Also, CAAR efficiency is influence by the intermembrane distance between the T cell and its target, see FIG. 4.

Figure 5:
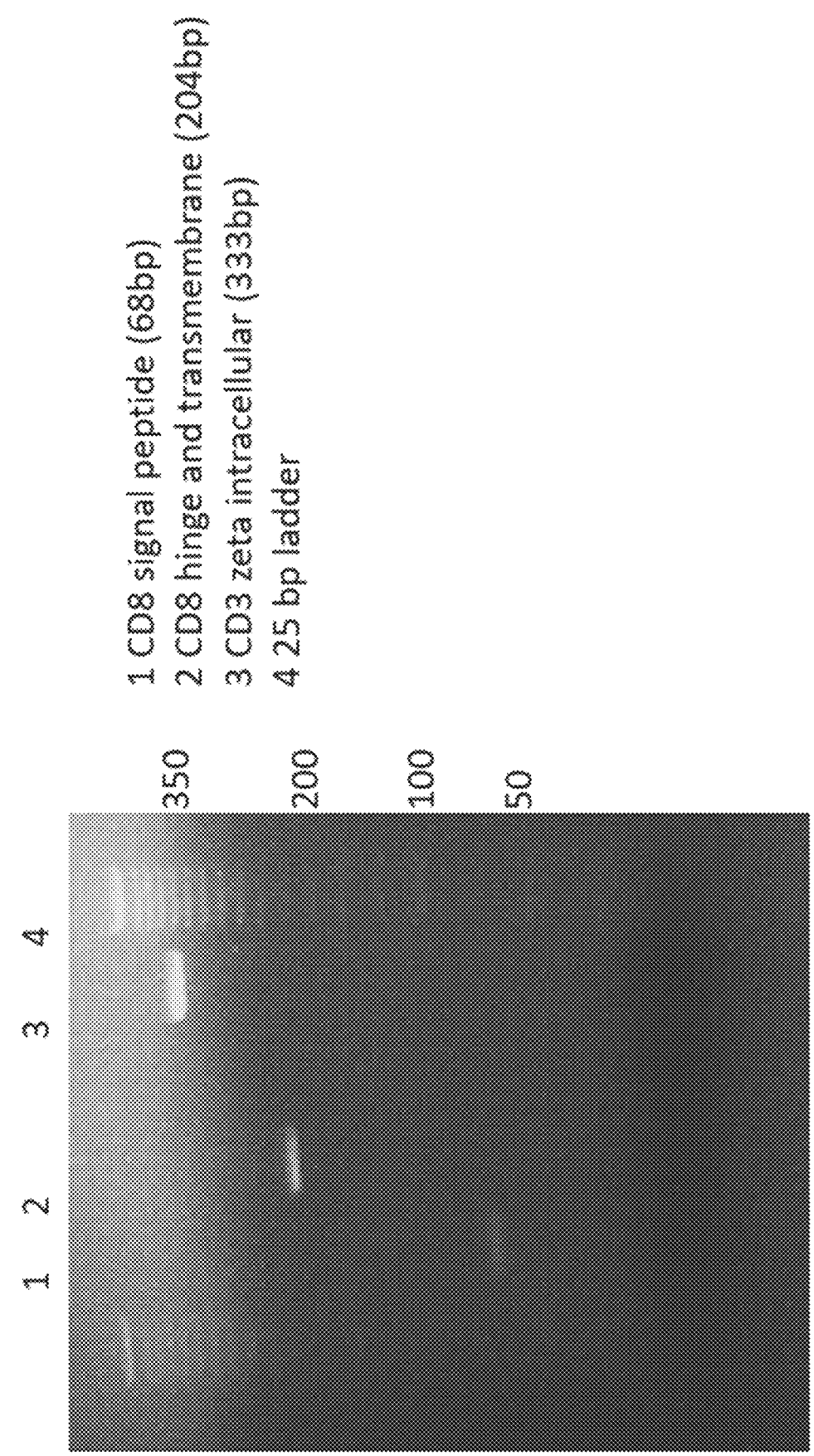
FIG. 5 is an image showing the amplification of the individual domains used in the Dsg3 CAAR from cDNA of peripheral blood mononuclear cells.
Figure 6:
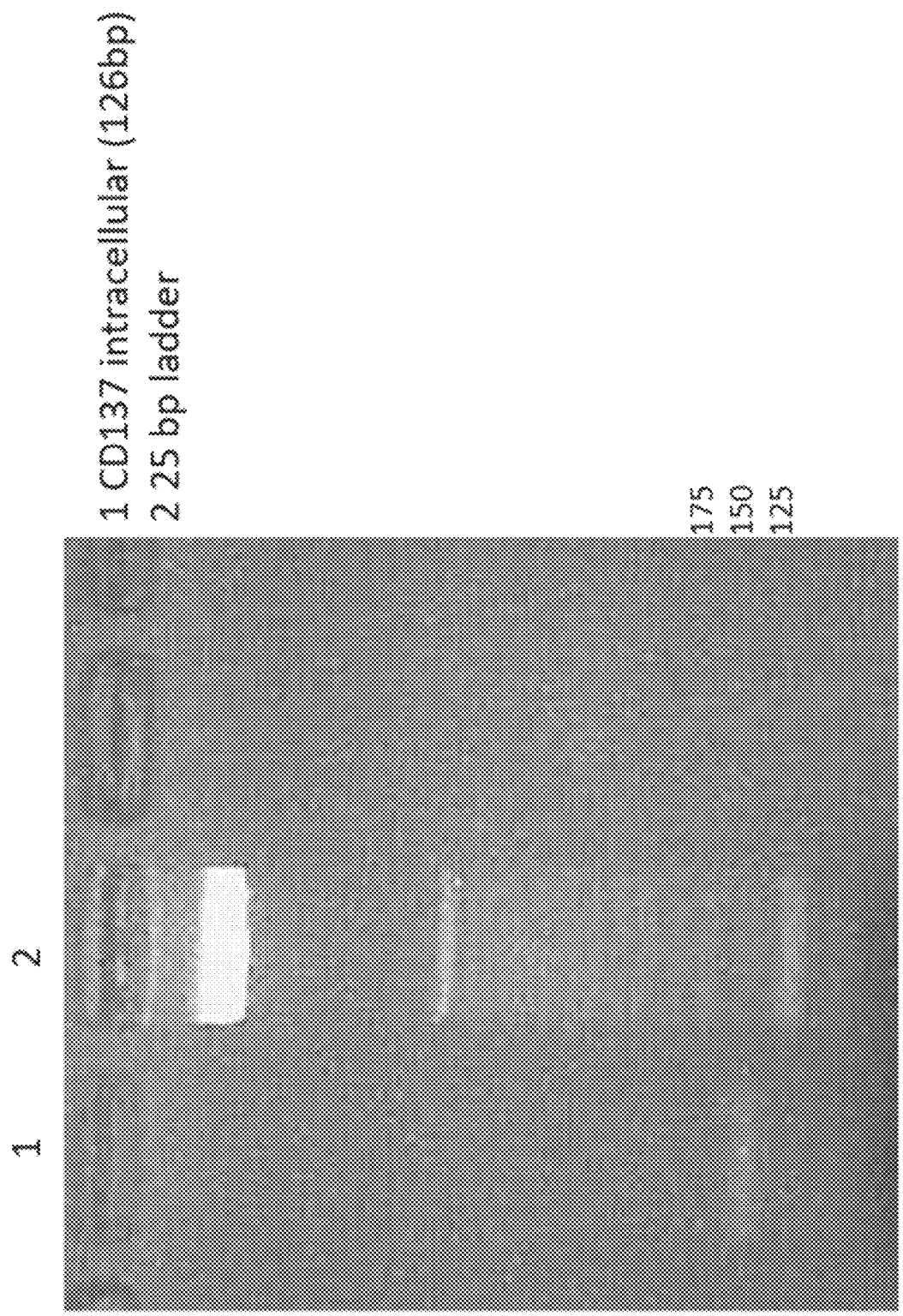
FIG. 6 is an image showing the amplification of CD137 used in the Dsg3 CAAR from cDNA of peripheral blood mononuclear cells.
Figure 7:
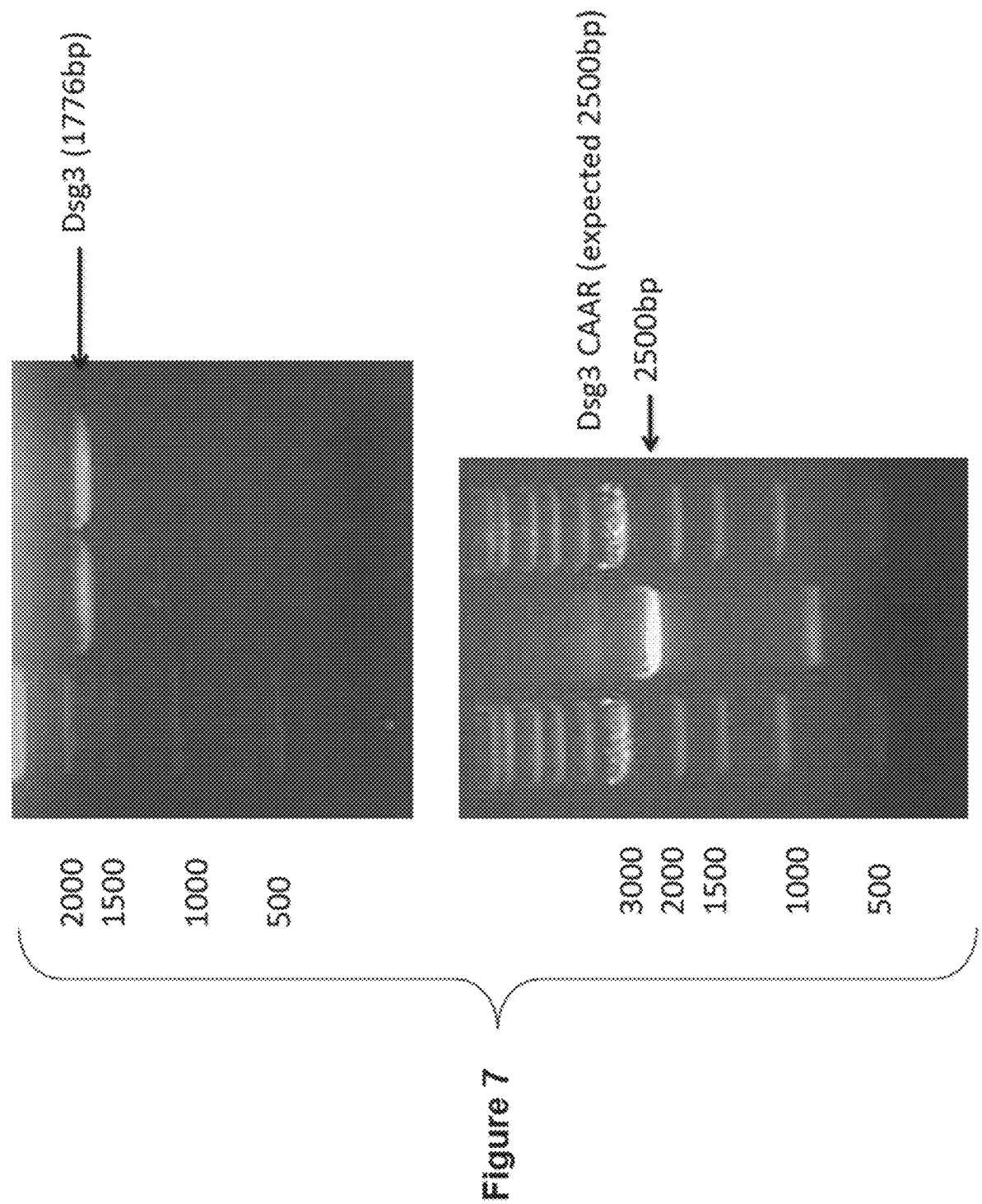
FIG. 7 is a set of images showing the amplification of Dsg3 used in the Dsg3 CAAR from plasmid DN653.

FIGS. 5-6 illustrate the ability to amplify individual domains of Dsg3 (FIG. 5) and CD137 (FIG. 6) from cDNA of peripheral blood mononuclear cells. FIG. 7 further shows amplification of Dsg3 and Dsg3 CAAR from plasmid DN653.

Figure 8:
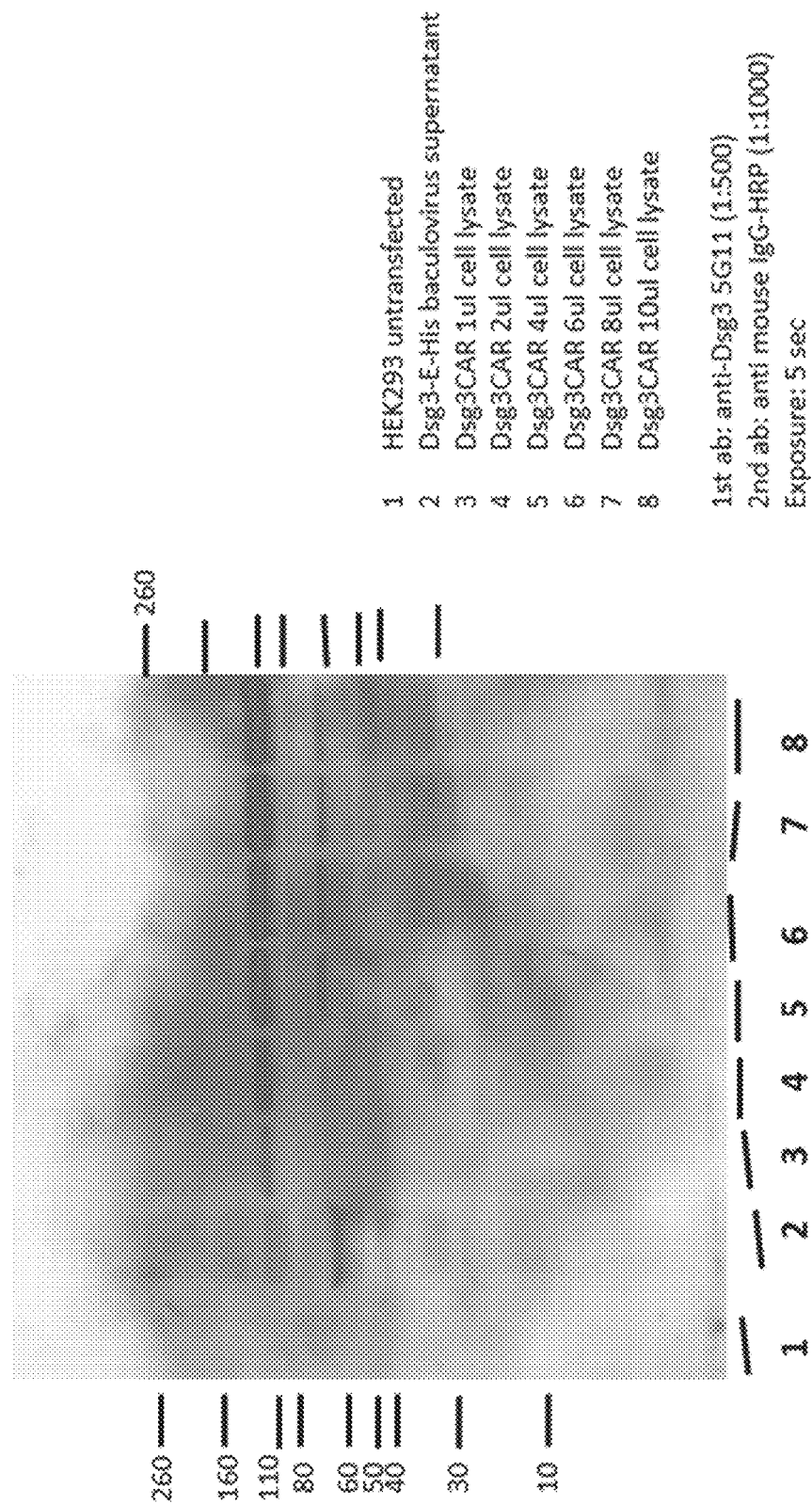
FIG. 8 is an image showing a western blot of Dsg3 CAAR to determine protein expression 48 hours after transformation and cell lysis of 293T cells under reducing conditions. Dsg3 E-His baculovirus supernatant is a positive control, untransfected HEK293T cells are a negative control. The expected size is 96 kDa for the unglycosylated protein, which typically migrates at ~112 kD with glycosylation.

Dsg3 CAAR protein was analyzed by western blot 48 hours after transformation and cell lysis of 293T cells under reducing conditions (FIG. 8). Dsg3 E-His baculovirus supernatant was a positive control, untransfected HEK293T cells were a negative control. The expected size was 96 kDa for the unglycosylated protein, which typically migrates at ~112 kD with glycosylation.

To evaluate the cytotoxicitiy of Dsg3 CAARs, the ability of Dsg3 CAAR expressed in primary human T cells to kill target cells expressing anti-Dsg3 surface autoantibodies (test for efficacy) and the potential for Dsg3 CAAR to kill off-target cells that may express a surface Fc receptor, which could bind PV autoantibodies and result in unintended redirected lysis (test for safety) was determined.

Figure 9:
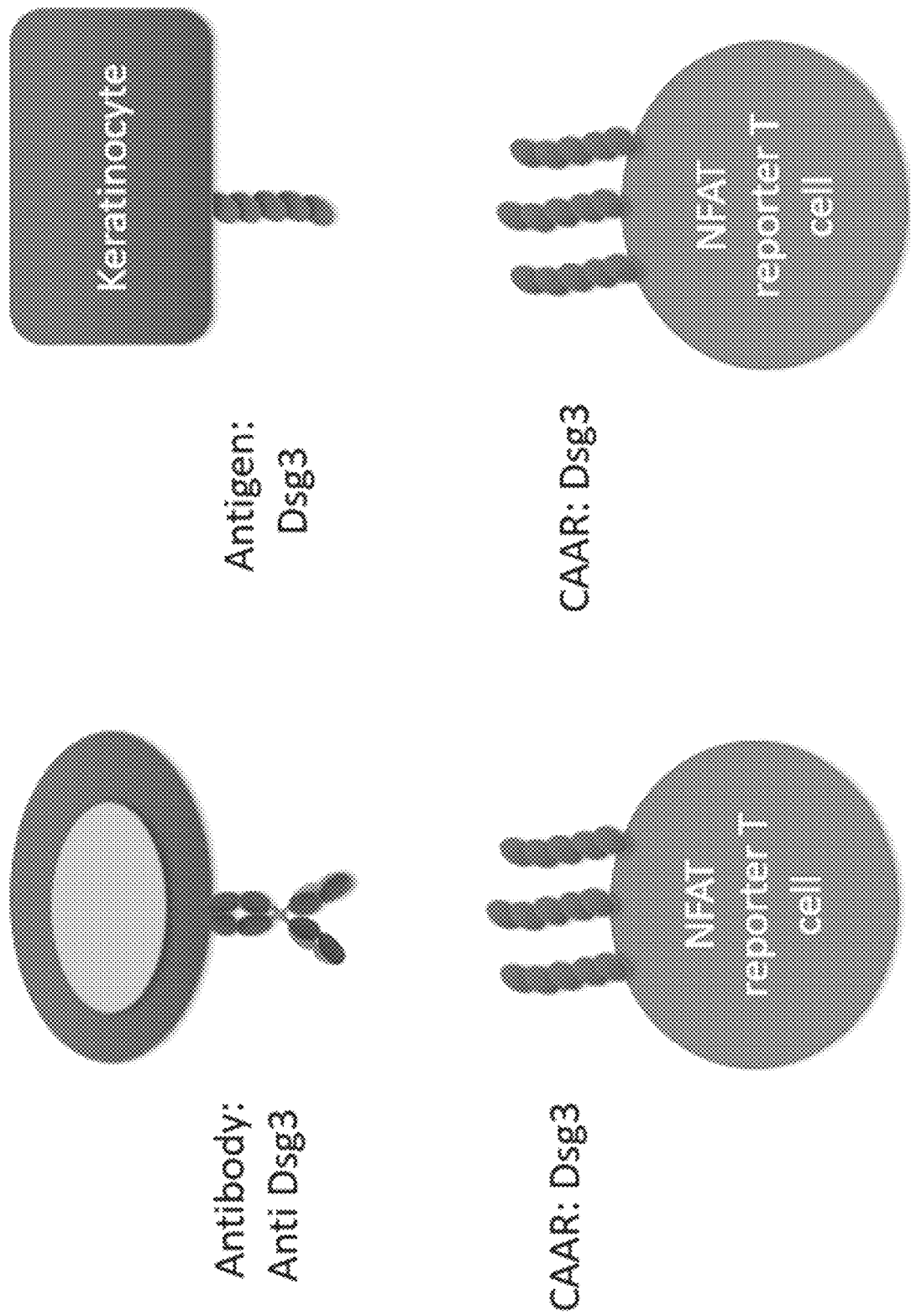
FIG. 9 is a schematic drawing describing the experiments to test specificity of the Dsg3 CAAR toward intended and unintended targets.

Dsg3 CAAR specificity toward intended and unintended targets was tested in lysis assays. It was anticipated that the Dsg3 CAART cells would kill anti-Dsg3 B cells as an intended target because of a high affinity interaction between the Dsg3 CAAR and anti-Dsg3 autoantibody (left side of FIG. 9). Whereas weak hemophilic interactions between Dsg3 CAART cells and cells expressing anti-Dsg3 with a Fc receptor (keratinocytes) would not result in killing by the Dsg3 CAART cells (right side of FIG. 9).

Figure 10:
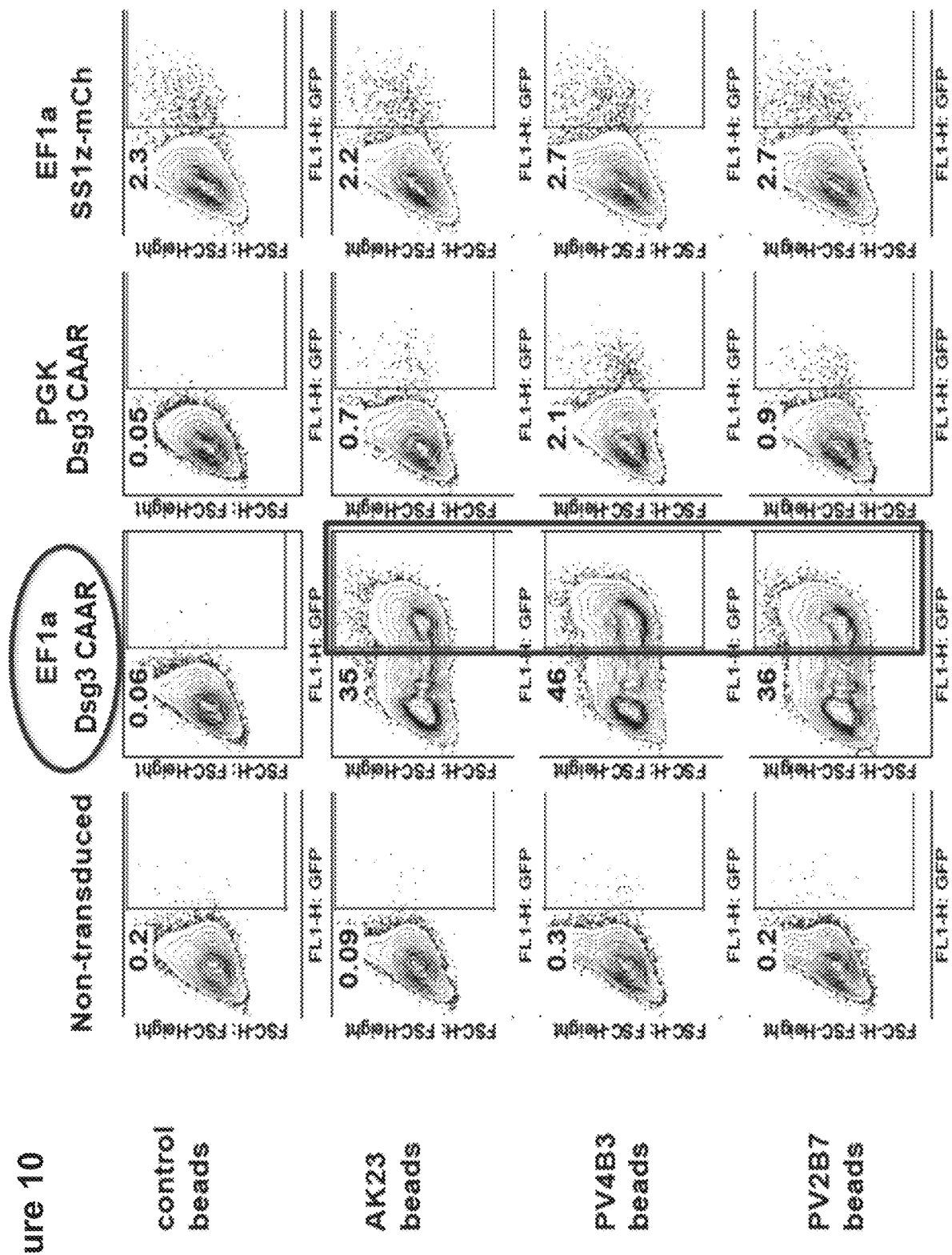
FIG. 10 is a panel of flow cytometry plots showing the Dsg3 CAAR signals after exposure to the intended target. NFAT-GFP Jurkats cells expressing Dsg3-CAAR were stimulated with antibody coated beads at a ratio of 3:1 (beads:cells). AK23, PV4B3, and PV2B7 are Dsg3-specific mAbs, which if bound to the CAAR, should trigger signaling resulting in GFP expression. EF1a promoter functioned better than the PGK promoter and resulted in specific signaling. SS1=anti-mesothelin CAR, positive control, had baseline positive activity. Non-transduced, negative-control, no GFP signal detected.

As expected, Dsg3 CAAR Jurkat cells did not show strong redirected lysis. NFAT-GFP Jurkats cells expressing Dsg3-CAAR were stimulated with antibody coated beads at a ratio of 3:1 (beads:cells). Flow cytometry plots shown in FIG. 10 indicated that signaling in Dsg3 CAAR Jurkat cells was present after exposure to PV target antibodies. AK23, PV4B3, and PV2B7 are Dsg3-specific mAbs, which if bound to the CAAR Jurkat cells, should trigger signaling that induces GFP expression. EF1a promoter functioned better than the PGK promoter and resulted in specific signaling. SS1=anti-mesothelin CAR was used as a positive control and had baseline positive activity. Non-transduced cells were used as a negative-control and no GFP signal was detected.

Figure 11:
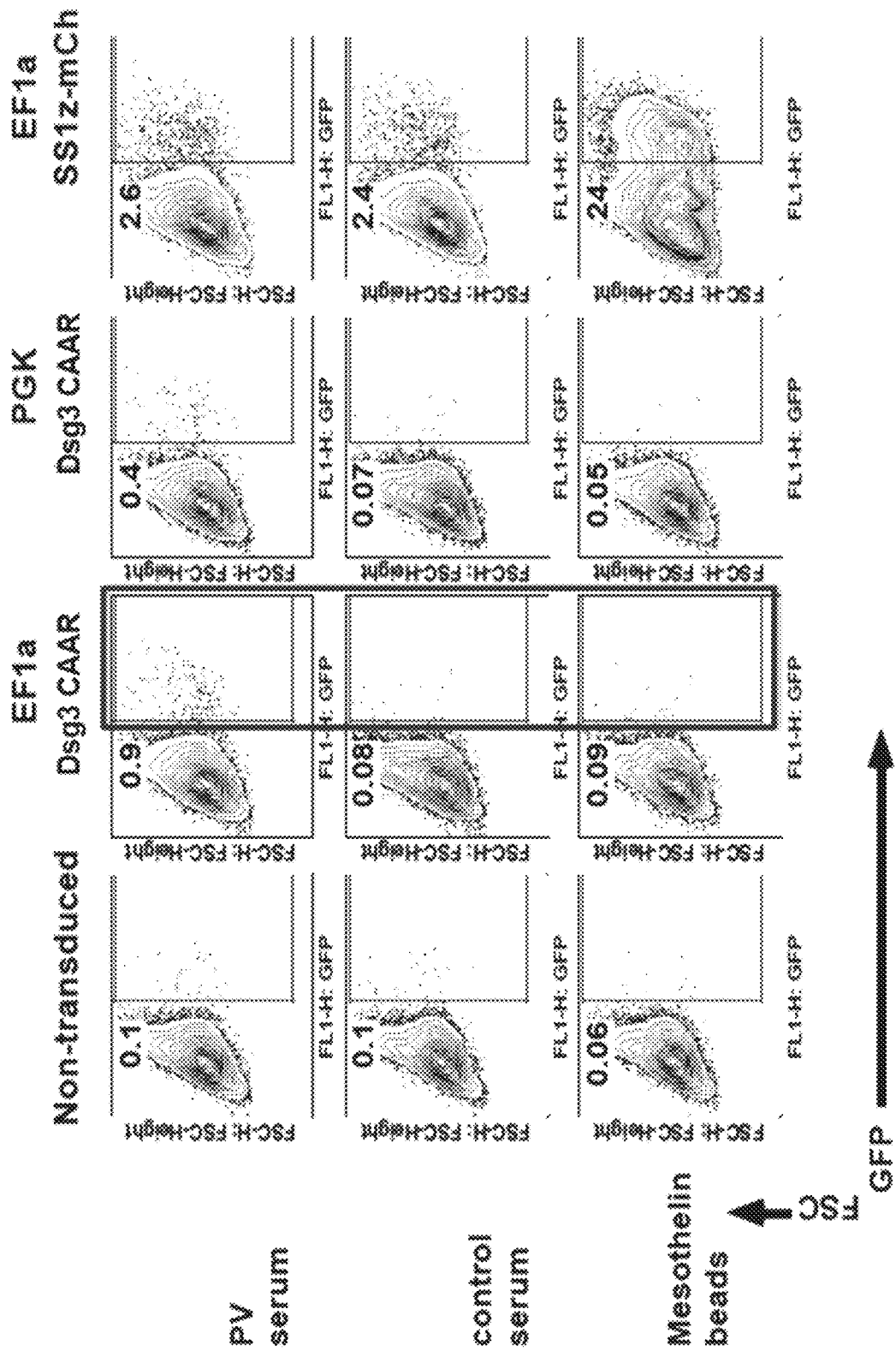
FIG. 11 is a panel of flow cytometry plots showing the Dsg3 CAAR induces low level but specific signaling after exposure to polyclonal pemphigus vulgaris (PV) patient serum IgG (reflecting the low overall percentage of total IgG that is Dsg3-specific).
Figure 12:
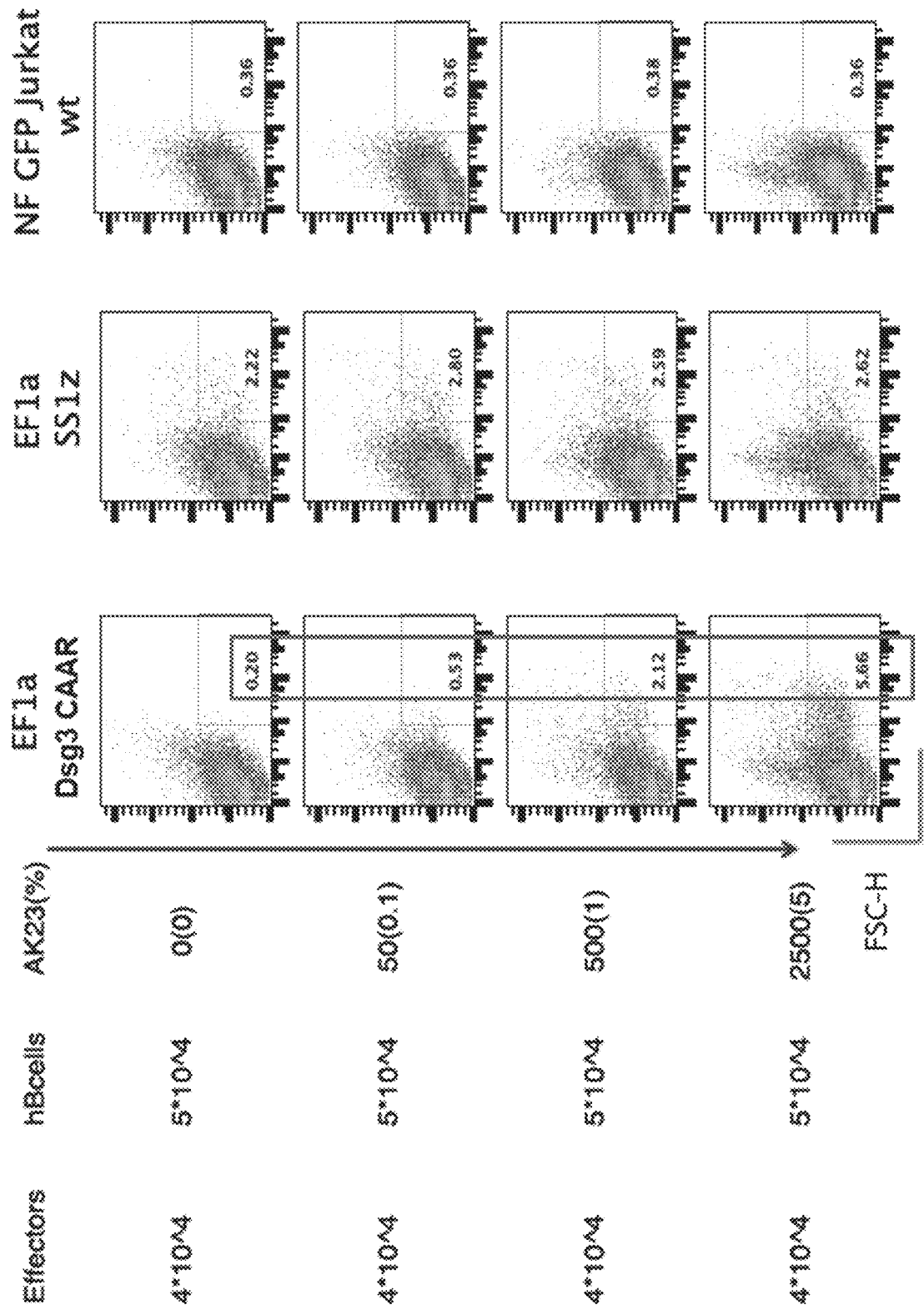
FIG. 12 is a panel of flow cytometry plots showing the Dsg3 CAAR responds to low numbers of surface IgG+ cells (AK23 hybridoma) in a dose-dependent manner.
Figure 13:
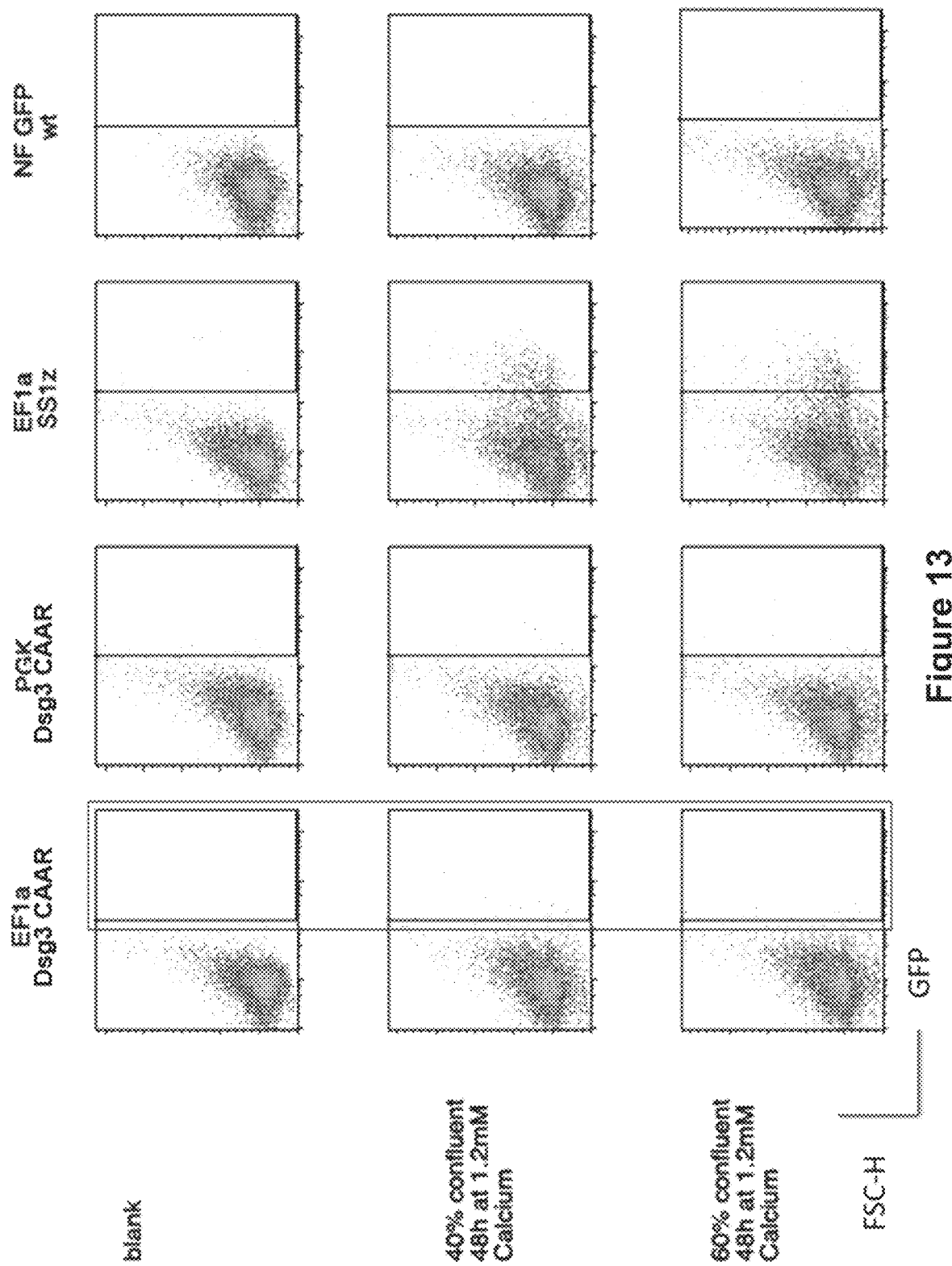
FIG. 13 is a panel of flow cytometry plots showing the safety of Dsg3 CAARs by no induction of signaling when exposed to Dsg3 expressing keratinocytes, indicating that interactions of Dsg3 with desmosomal cadherins on keratinocytes should not result in skin or mucous membrane toxicity.

Low level, but specific, signaling was induced in Dsg3 CAAR Jurkat cells after exposure to polyclonal pemphigus vulgaris (PV) patient serum IgG (reflecting the low overall percentage of total IgG that is Dsg3-specific) (FIG. 11). Dsg3 CAAR Jurkat cells also responded to low numbers of surface IgG on cells (AK23 hybridoma) in a dose-dependent manner. Signaling was not induced when Dsg3 CAAR Jurkat cells were exposed to Dsg3 expressing keratinocytes, indicating that interactions of Dsg3 with desmosomal cadherins on keratinocytes should not result in skin or mucous membrane toxicity.

Figure 14:
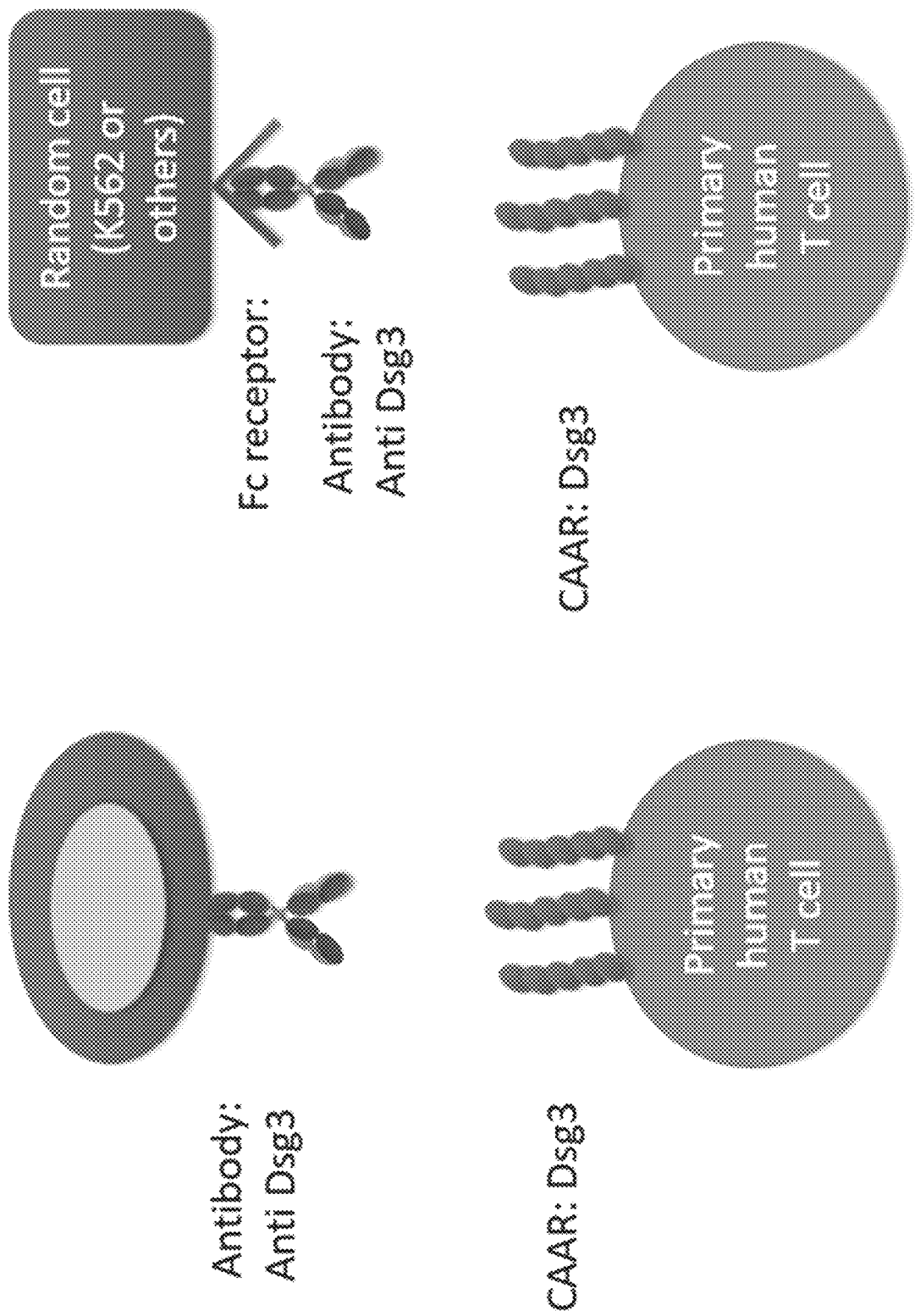
FIG. 14 is a schematic diagram showing the different scenarios for testing cytotoxicity toward target cells that express anti-Dsg3 surface autoantibodies and off-target cells that express surface Fc receptors that could bind serum PV autoantibodies resulting in unintended redirected lysis.

To test safety of Dsg3 CAAR effector cells, different scenarios were proposed for testing cytotoxicity toward target cells that express anti-Dsg3 surface autoantibodies and off-target cells that express surface Fc receptors that could bind serum PV autoantibodies resulting in unintended redirected lysis. The cells on the left in FIG. 14 show expected killing of anti-Dsg3 B cells as the intended target. The cells on the right in FIG. 14 show unintended killing of cells that express Fc receptors, potentially through redirected lysis.

Figure 15:
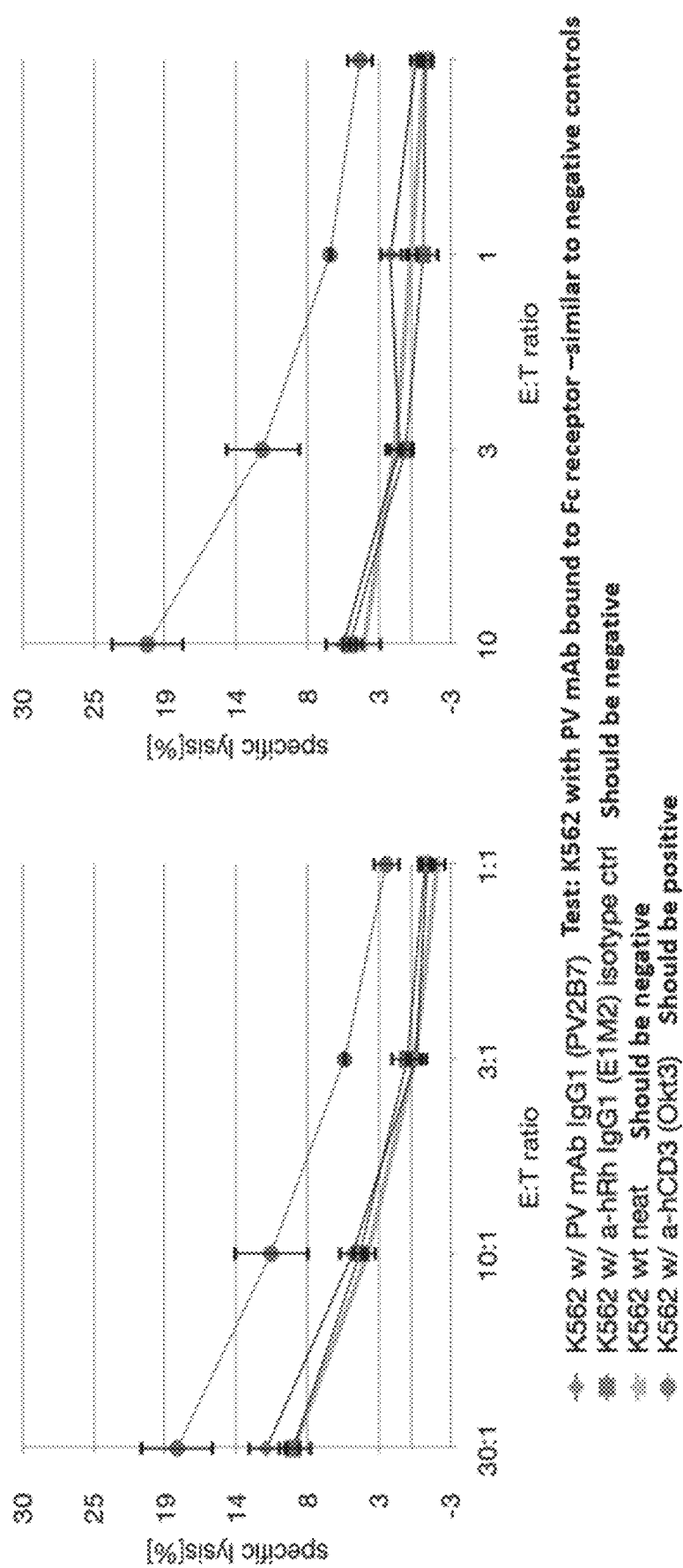
FIG. 15 is a panel of graphs showing Dsg3 CAAR does not demonstrate redirected lysis against a K562 cell line that expresses surface Fc receptors that are pre-loaded with PV anti-Dsg3 mAb (PV2B7).

Dsg3 CAAR effector cells were exposed to a K562 cell line that expressed surface Fc receptors pre-loaded with PV anti-Dsg3 mAb (PV2B7). No redirected lysis was observed with PV mAb bound to Fc receptor (left graph in FIG. 15), as it behaved similar to the negative controls and non-transduced cells (right graph in FIG. 15).

TCR activation (and hence killing) is dependent on the distance between effector and target cell (ideal distance is 14-15 nm). Shorter or longer distances will result in loss of TCR activation. The target (surface IgG) for the Dsg3 CAAR is ~8.4 nm. Desmoglein 3 is roughly 12.5-18 nm long. The desmosomal gap is ~40 nm. Desmoglein 3 consists of 5 Ig-like domains with a size of approximately 3.5 nm each. Trans- and cis-interactions are approximately 24.5 nm when interacting through EC2 cis-interaction.

Figures 16A, 16B:
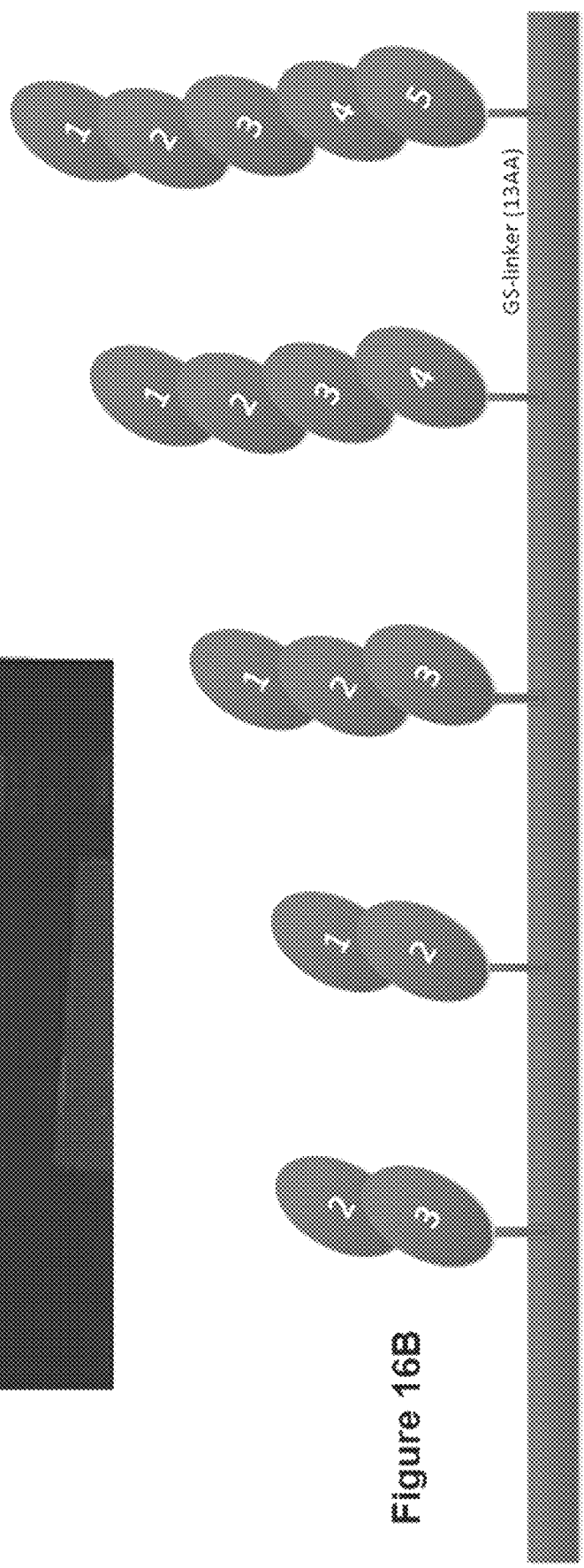
FIG. 16A is an image of an electrophoretic gel showing amplification of the different Dsg3 extracellular domains, EC2-3, EC1-2, EC1-3, EC1-4 and EC1-5, which are constructed to optimize Dsg3 CAAR cytotoxicity, since the efficacy of CAAR-mediated cytotoxicity is dependent on the distance between effector and target cell.
FIG. 16B is a schematic drawing of the Dsg3 extracellular domains amplified in FIG. 16A.

To determine if expression of just a part of Dsg3 may result in enhanced CAAR activation, due to optimal intercellular distance for the immunologic synapse, different Dsg3 EC domain constructs (intermolecular adhesion domains are contained in EC1-2) were used. Other EC-domain constructs may also be used and are detailed in the disclosure. FIG. 16A is an image of an electrophoretic gel showing amplification of the different Dsg3 extracellular domains, EC2-3, EC1-2, EC1-3, EC1-4 and EC1-5 (FIG. 16B), which were constructed to optimize Dsg3 CAAR cytotoxicity, since the efficacy of CAAR-mediated cytotoxicity is dependent on the distance between effector and target cell.

Figure 17:
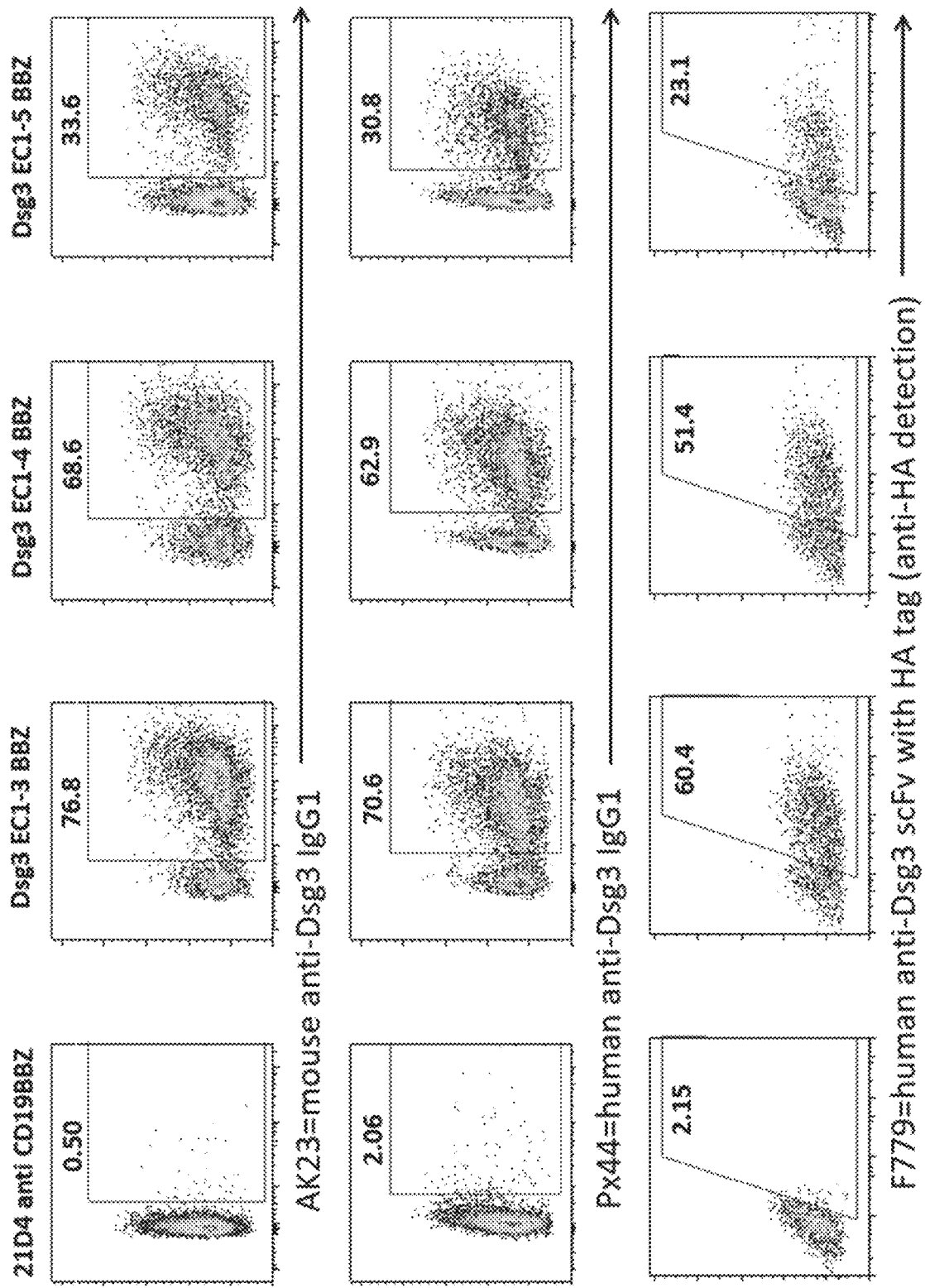
FIG. 17 is a panel of flow cytometry plots showing the Dsg EC1-3, EC1-4, EC1-5 CAARs can be expressed in primary human T cells and are recognized by 3 different PV anti-Dsg3 mAbs, AK23, Px44, and F779. EC1-2 did not effectively express. 21D4=neg control CAR.

Dsg EC1-3, EC1-4, EC1-5 CAARs were expressed in primary human T cells and recognized by 3 different PV anti-Dsg3 mAbs, AK23, Px44, and F779 (FIG. 17). EC1-2 did not effectively express.

Figure 18:
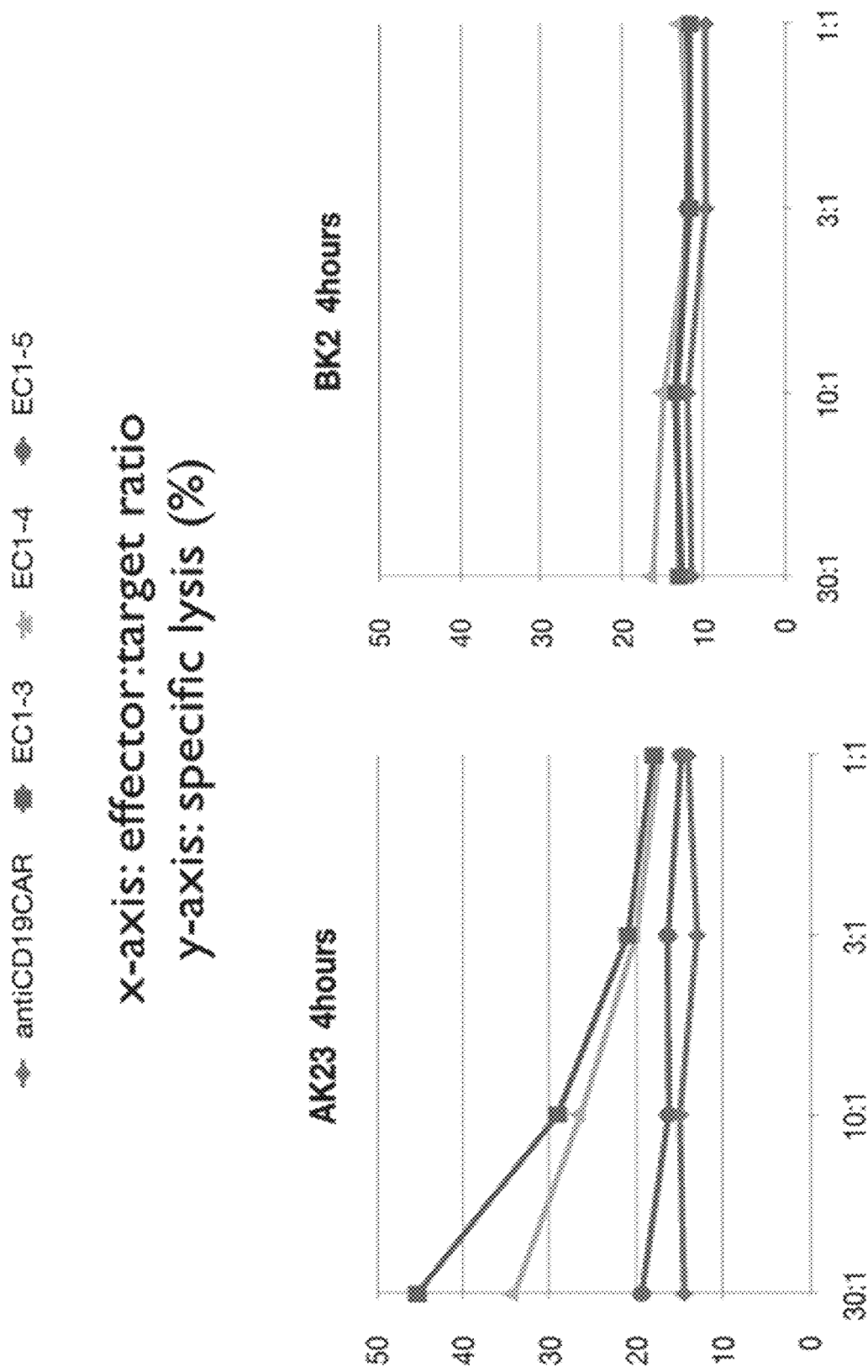
FIG. 18 is a panel of graphs showing the efficacy of the Dsg3 CAAR against an anti-Dsg3 IgG mouse hybridoma (meant to model a PV-specific human memory B cell or plasmablast that displays anti-Dsg3 IgG on the cell surface). The Dsg3 CAAR, expressed on the surface of primary human T cells, shows specific in vitro killing of AK23 (an anti-Dsg3 hybridoma) in a chromium release assay after 4 hours.

The efficacy of the Dsg3 CAAR against an anti-Dsg3 IgG mouse hybridoma (meant to model a PV-specific human memory B cell or plasmablast that displays anti-Dsg3 IgG on the cell surface) is shown in FIG. 18. The Dsg3 CAAR was expressed on the surface of primary human T cells and specific in vitro killing of AK23 (an anti-Dsg3 hybridoma) was observed in a chromium release assay after 4 hours as compared to the negative control, BK2.

Figure 19:
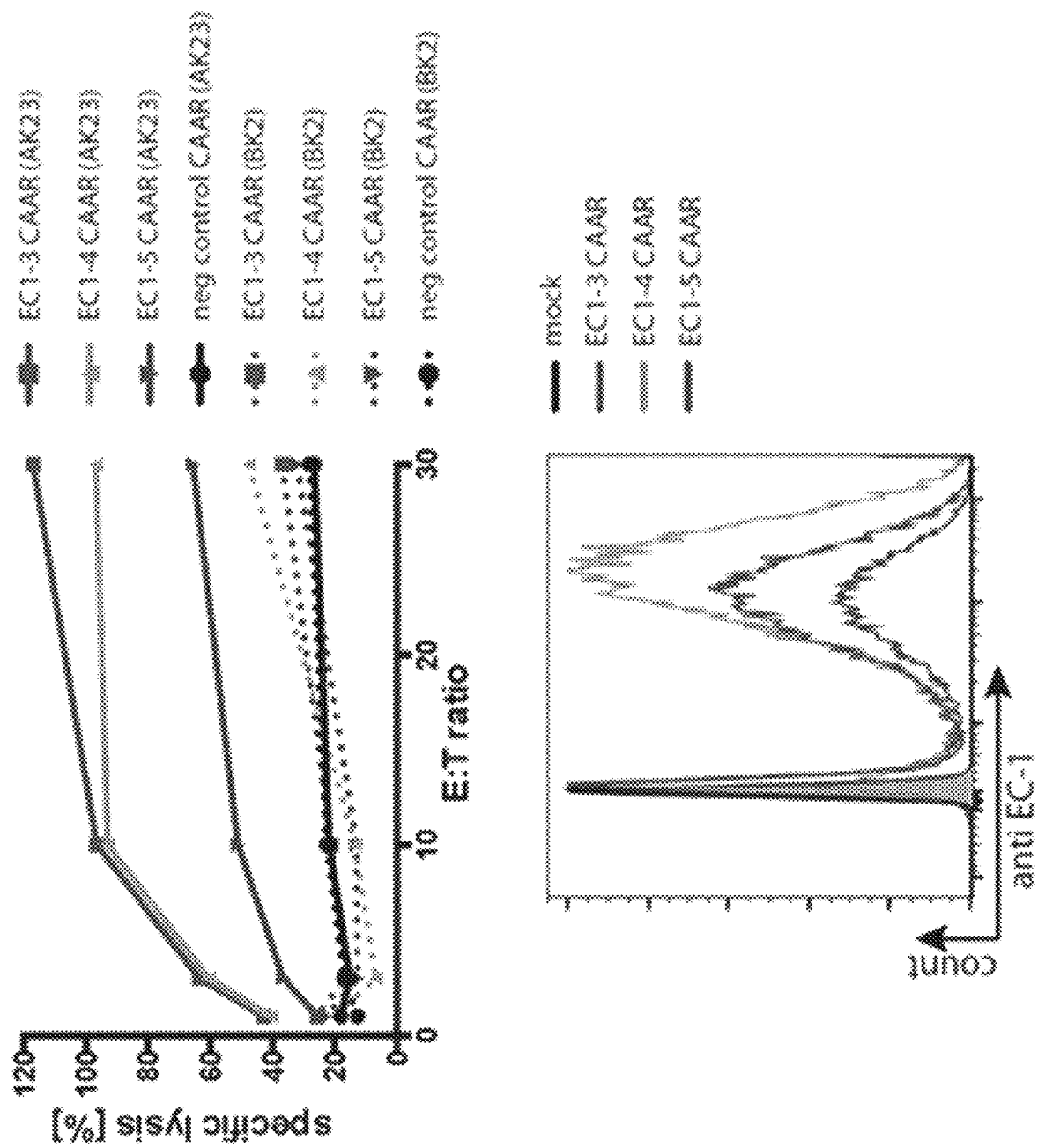
FIG. 19 is a panel of graphs showing Dsg3 CAAR killing of AK23 hybridoma increases over time in a chromium release assay after 24 hours. The killing efficacy of the CAARs correlates with CAAR size (shorter is better so EC1-3>EC1-4>EC1-5). Mock=anti-human CD19 CAR; human CD19 is not expressed on the target hybridoma cell. Control hybridoma (BK2) which does not express a Dsg3-autoantibody, shows some killing by Dsg3 CAARs over 24 hours perhaps due to human-mouse alloreactivity.

Efficacy of Dsg3 CAAR T cells was further shown to specifically kill AK23 hyridoma in a chromium-51 release assay. Dsg3 CAAR killing of AK23 hybridoma increased over time in a chromium release assay after 24 hours (FIG. 19). Essentially, about 100% killing was observed with the Dsg3 EC1-3 and EC1-4 CAAR after 16 hours. The killing efficacy of the CAARs correlated with CAAR size (shorter was better EC1-3>EC1-4>EC1-5). Human CD19 was not expressed on the target hybridoma cell as anti-human CD19 CAR was the mock control. Control hybridoma (BK2), which does not express a Dsg3-autoantibody, demonstrated some killing by Dsg3 CAAR cells over 24 hours, perhaps due to human-mouse alloreactivity.

Figure 20:
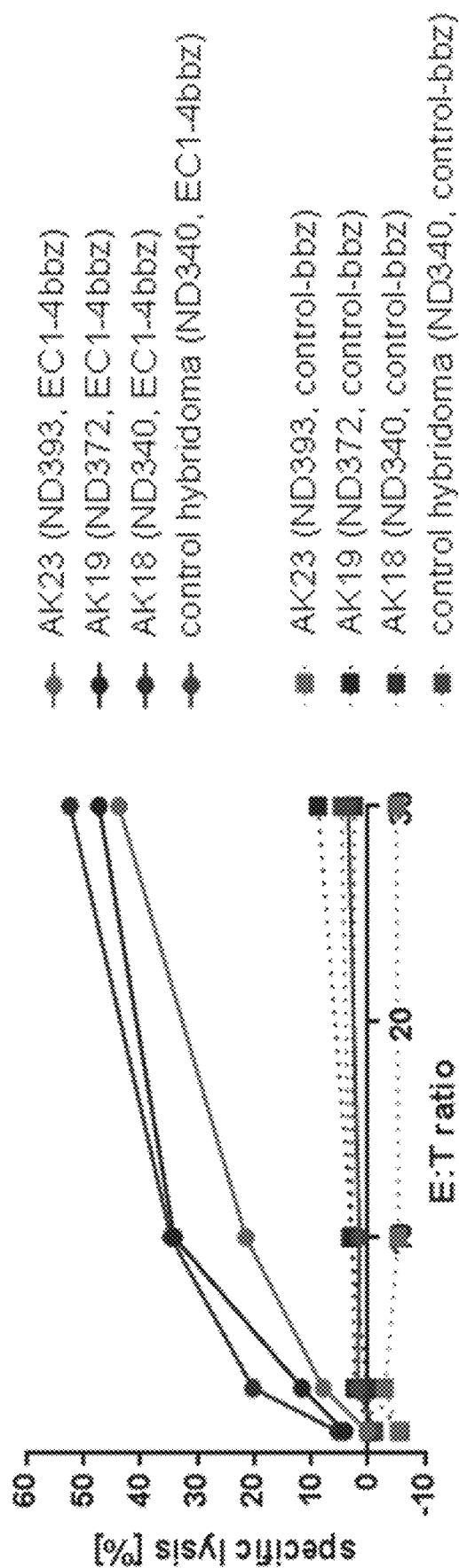
FIG. 20 is a graph showing killing of anti-Dsg3 cells targeting different Dsg3 epitopes by Dsg3 CAART cells in a 4 hour chromium release assay. Values are representative of at least 4 experiments with T cells from different normal donors (ND).
Figure 21:
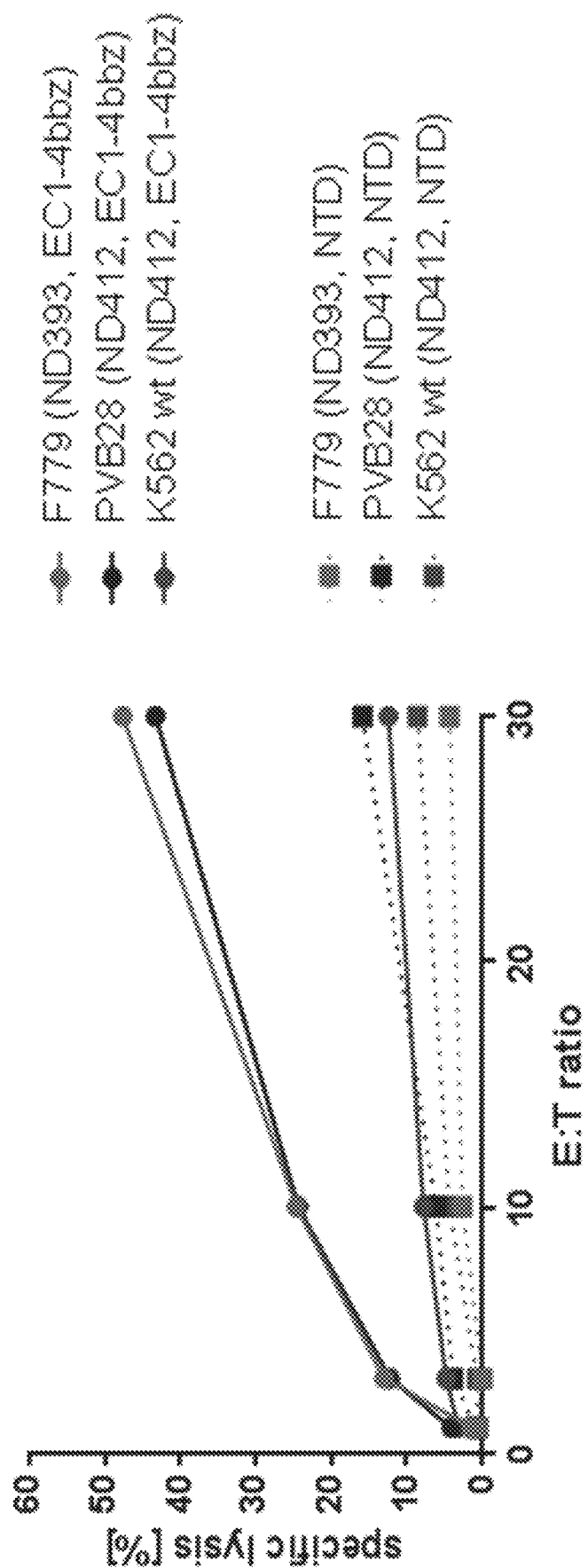
FIG. 21 is a graph showing killing of anti-Dsg3 cells targeting additional different human Dsg3 epitopes by Dsg3 CAART cells in a 4 hour chromium release assay.

Dsg3 CAART cells killed anti-Dsg3 cells targeting a broad range of epitopes, F779 (anti-EC1) and PVB28 (anti-EC2). Dsg3 EC1-4 CAAR (EC1-4bbz) killed anti-EC1, anti-EC2 and anti-EC3 B cells, see FIG. 20. Dsg3 EC1-4 CAAR also did not kill K562 wild type (wt) cells (FIG. 21), as well as non-transduced T cells did not kill F779/PVB28 K562 cells. The K562 cells expressing F779 or PVB28 surface immunoglobulins also expressed CD19 and mesothelin. Nontransduced (NTD) T cells were used as a negative control.

Figure 22:
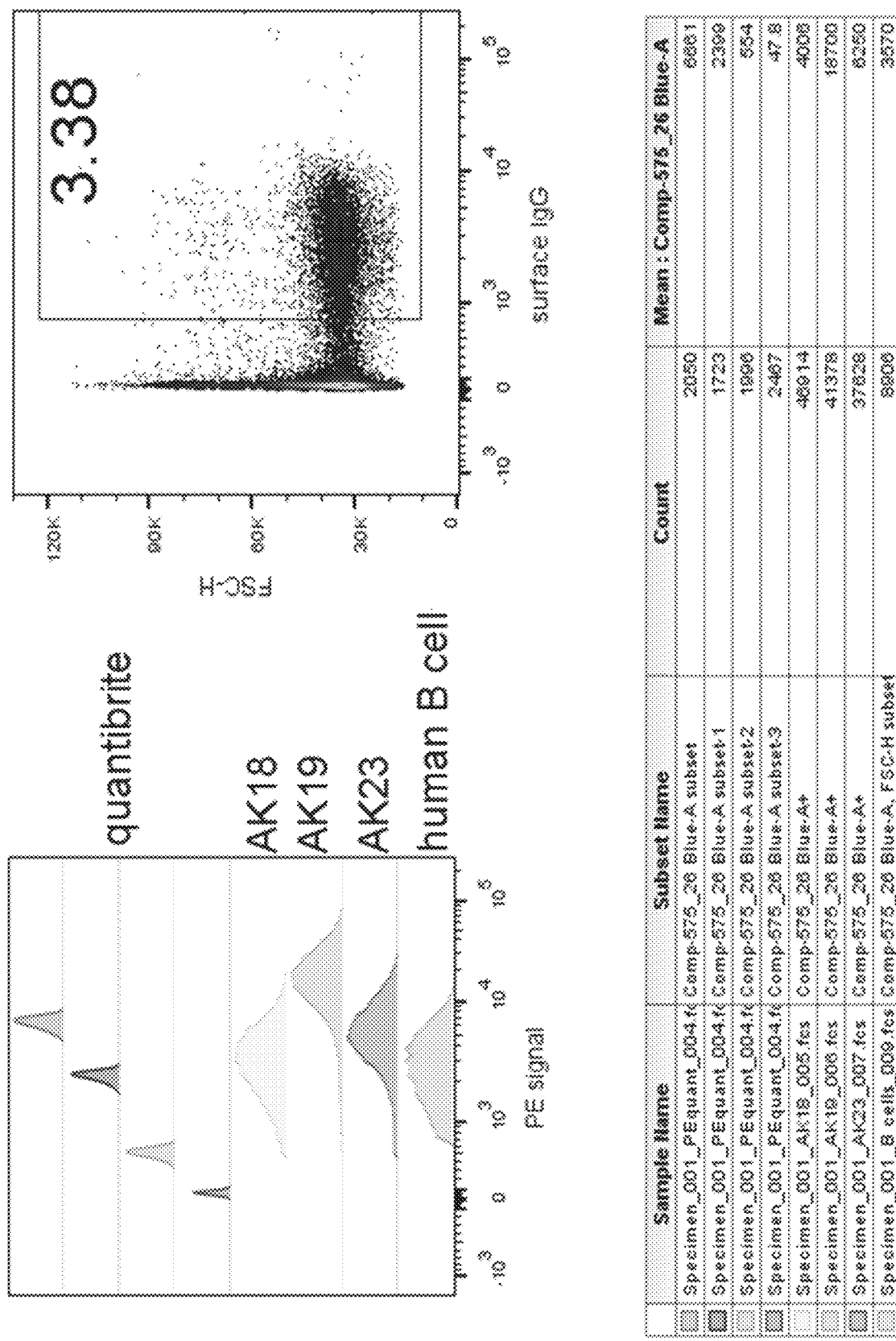
FIG. 22 is a panel of images showing that surface IgG density of anti-Dsg hybridomas is comparable to human memory B cells. Different cell types are taken into account to calculate the relative target density.

To determine if antibody density is comparable between hybridomas and memory B cells, quantification of anti-Dsg surface IgG was performed on hybridoma cells, AK18, AK19 and AK23, and human B cells. Density of IgG on hybridomas was measured by fluorescence/protein (F/P) ratio. Given the large size differences between the cells, hybridoma cell about 567.5 um$^2$ and human B cells about 160.3 um$^2$, there was about 3.54× more surface area for hybridoma than human memory B cells. Thus, the fluorescence/protein (F/P) ratio needed to take the surface area into consideration. The normalized surface IgG density was calculated at about AK18: 1130, AK19: 5300, AK23: 1765 and human B cells: 3570, see FIG. 22.

Figure 23:
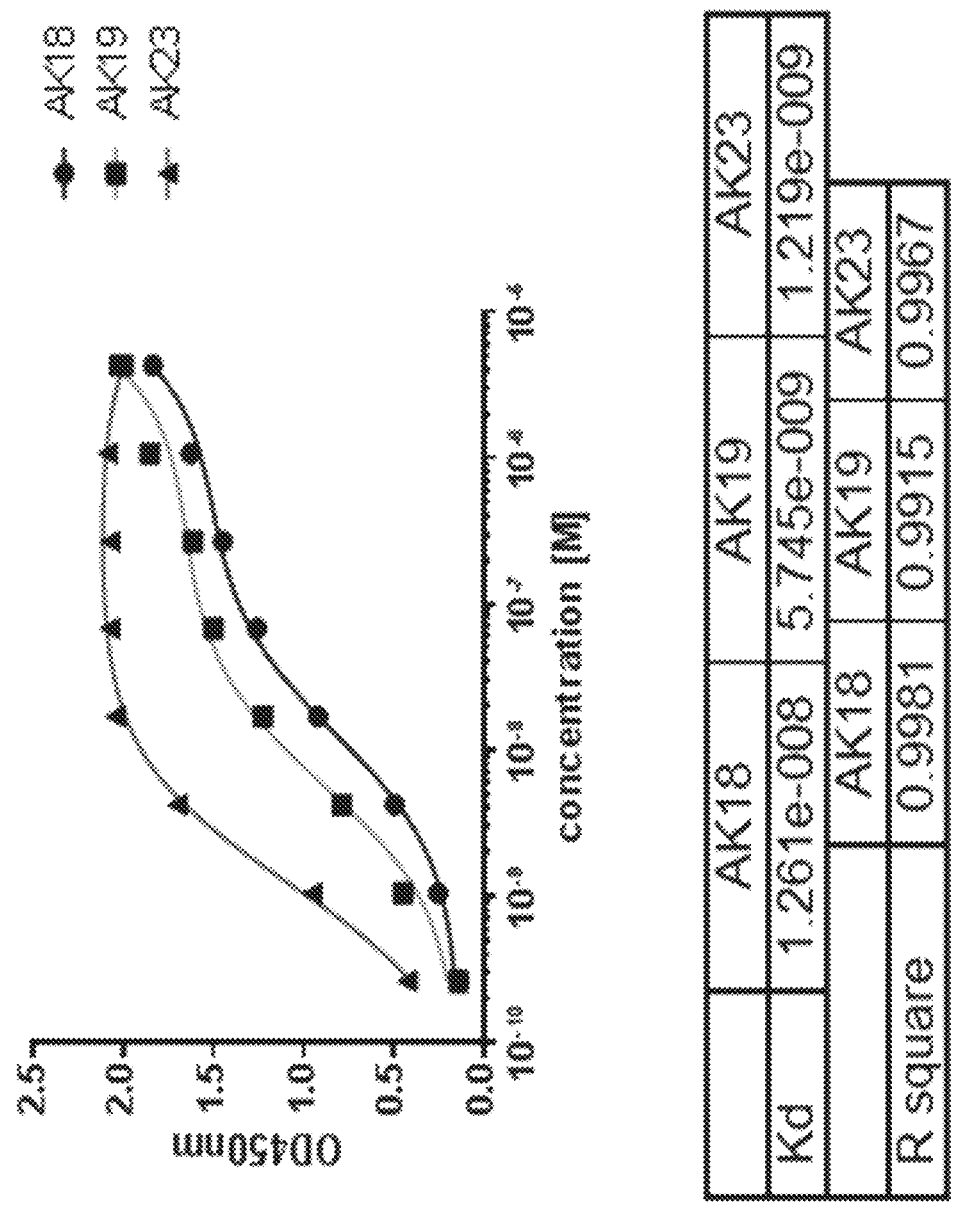
FIG. 23 is a graph showing relative affinity ELISA for different target antibodies of the Dsg3 CAAR, indicating that Dsg3 CAART cells kill target cells within a range of antibody affinities.

Dsg3 CAART cells were further tested to determine if antibody affinities affect efficacy. The relative affinities of the target immunoglobulins secreted by the hybridomas used in the killing assays described herein, AK18, AK19 and AK23, are shown in FIG. 23. The three antibodies have varying affinities and Dsg3 CAART cells are effective against all three.

Figure 24:
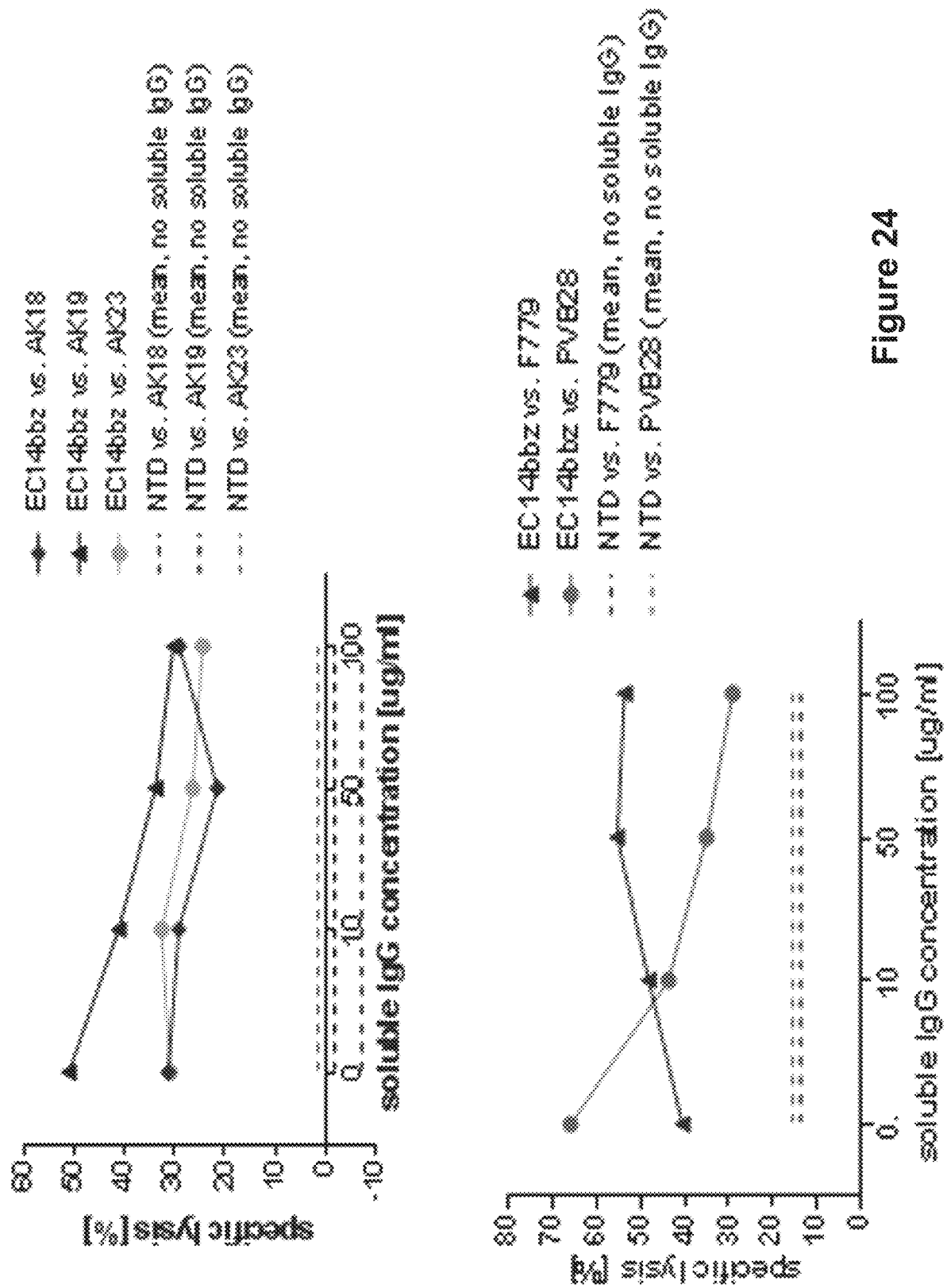
FIG. 24 is a panel of graphs showing that Dsg3 CAART cells are killed even in the presence of soluble blocking anti-Dsg3 antibody. Effector to target (E:T) ratio for all conditions: 30:1. $^{51}$Cr, 8 hours.

To further test the efficacy of Dsg3 CAART cells, soluble blocking anti-Dsg3 antibody was added to the killing assay. Dsg3 CAART cells demonstrated specific killing even in the presence of increasing concentrations of soluble antibody (FIG. 24). The killing assays were performed in the presence of the hybridoma and soluble antibody from the same clone. FIG. 24 demonstrates that Dsg3 CAART cells targeted cells even in the presence of soluble blocking anti-Dsg3 antibody for all conditions tested.

To test off-target killing of Dsg3 CAART cells, potential scenarios were examined. Cells expressing Fc receptors that bind serum anti-Dsg IgG could be killed by T cells expressing the Dsg CAAR. However, the intermembrane distance is likely too large to allow for effective killing. Serum anti-Dsg3 IgG typically also only presents a minority (~1%) of total serum IgG, suggesting that toxicity should be minimal. Keratinocytes that express desmosomal cadherins (desmogleins and desmocollins) could theoretically interact with the Dsg CAAR and be killed. However, intermembrane distance is likely suboptimal for killing, and affinity of interaction is too low (μM range).

Figure 25:
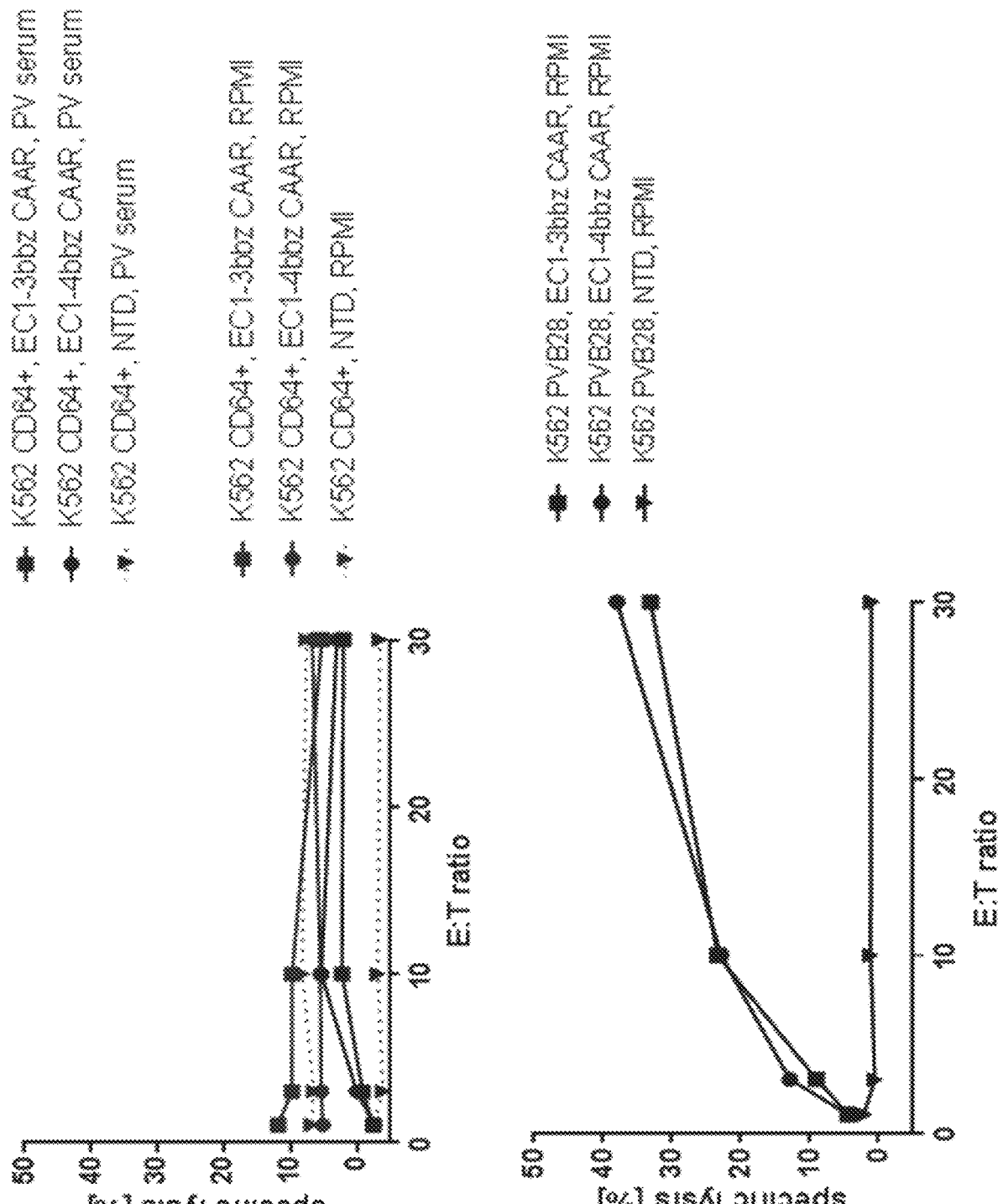
FIG. 25 is a panel of graphs showing that Dsg3 CAART cells do not kill Fc receptor expressing cells that may bind soluble anti-Dsg3 antibodies in PV patient serum by reversed antibody-dependent cellular toxicity (rADCC) in vitro.

Dsg3 bearing T cells were tested in a reversed antibody-dependent cellular toxicity (rADCC) assay to determine if Dsg3 CAART cells targeted Fc receptor expressing cells (upper graph in FIG. 25). FcgRI expressing K562 cells (CD64+ K562) were co-incubated for 8 hours with CAART cells in PV serum. Target cells were 100% positive for surface IgG, yet were not killed by Dsg3 CAART cells. K562 cells expressing PVB28 IgG4 in normal medium were used as a positive control to show that the same CAART cells were, in fact, functional (lower graph in FIG. 25), i.e. specifically killed target cells.

Figure 26:
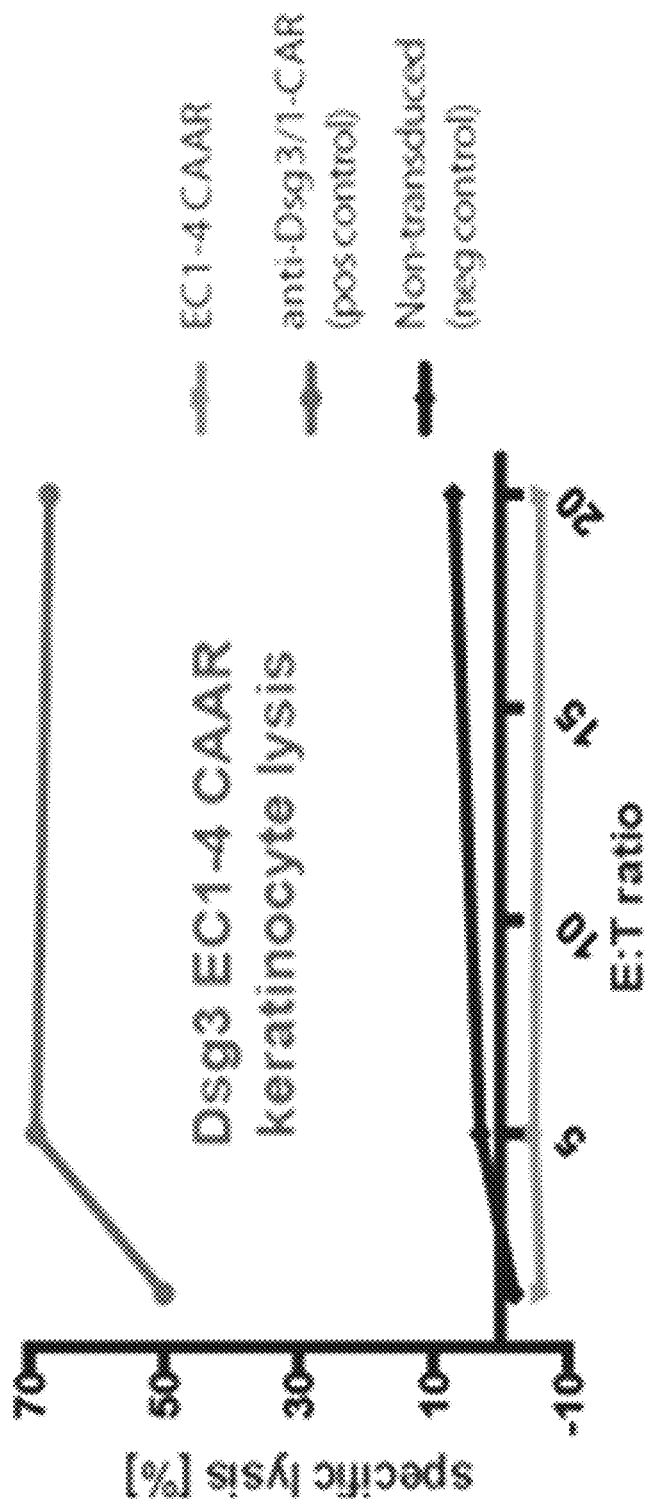
FIG. 26 is a graph showing that Dsg3 CAART cells do not kill primary keratinocytes.

Dsg3 CAAR T cells were incubated with primary human epidermal keratinocytes grown in calcium-containing media to induce desmosome assembly. No killing was observed with the Dsg3 EC1-4 CAART cells (FIG. 26). In contrast, CART cells consisting of a mAb against Dsg3 and Dsg1 effectively killed keratinocytes.

Figure 27:
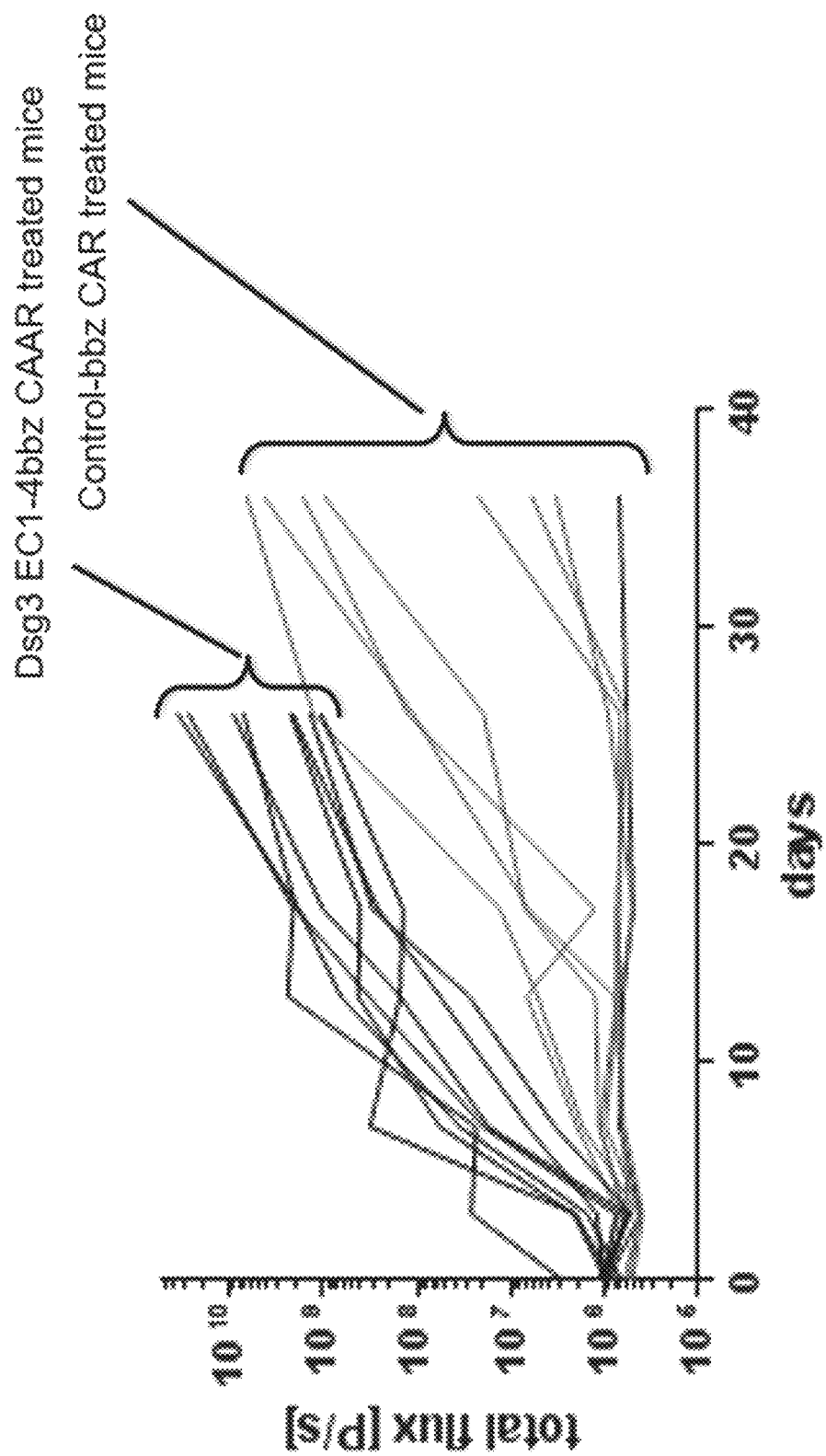
FIG. 27 is a graph showing that Dsg3 CAAR T cells effectively control bioluminescent IgG secreting anti-Dsg3 hybridoma cells in vivo.

Dsg3 CAAR T cells also effectively controlled IgG secreting hybridoma cells in vivo. FIG. 27 shows AK19 hybridoma cells and either Dsg3 EC1-4 CAAR T cells or control CAR T cells were co-engrafted into NSG mice. At the indicated time points, tumor burden was quantified by bioluminescence imaging. Bioluminescence >10e8 (total flux[P/s]) was used to declare mice 'dead.'

Figure 28:
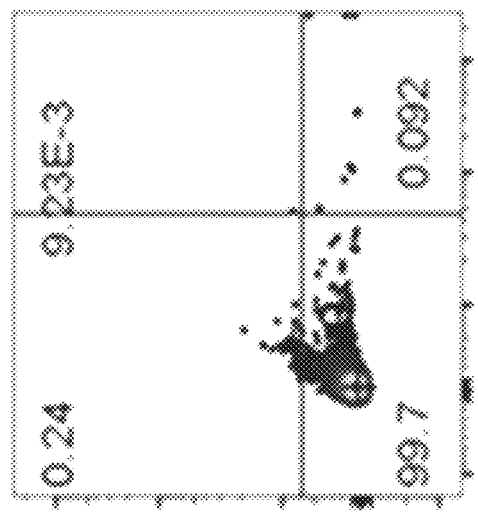
FIG. 28 is a panel of graphs showing by flow cytometric analysis that in the 4 mice from FIG. 27 that escape Dsg3 CAART treatment, bioluminescent "escape" hybridomas do not express surface IgG, explaining why they are no longer targeted by Dsg3 CAART cells. The numbers on the 3 panels on the right indicate individual mice. 9406 and 9407 show GFP+ cells that are surface IgG negative, indicating that these cells were not targeted by the Dsg3 CAAR T cells.
Figure 28:
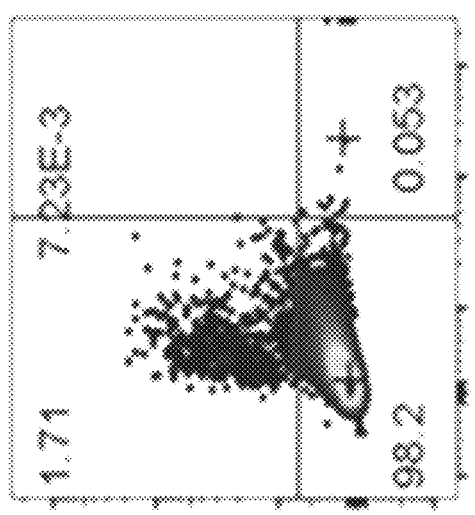
Figure 28:
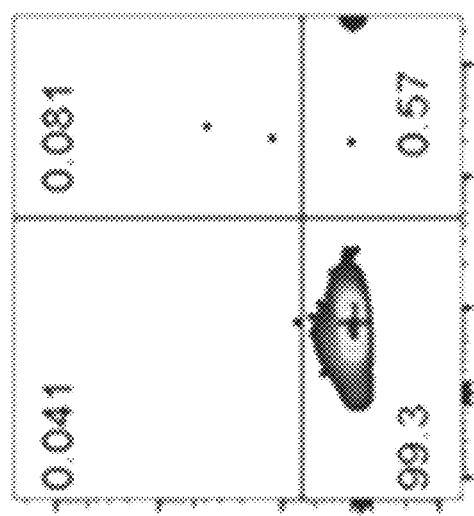
Figure 28:
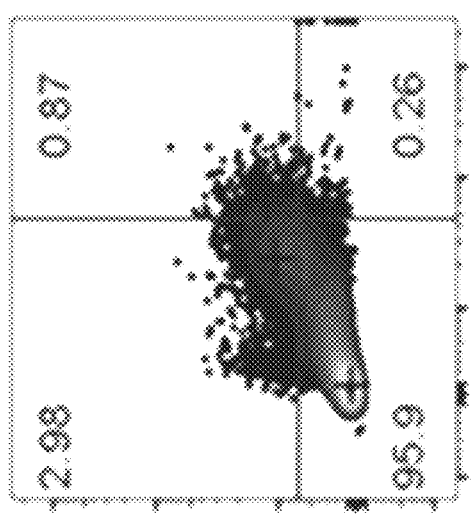
Figure 28:
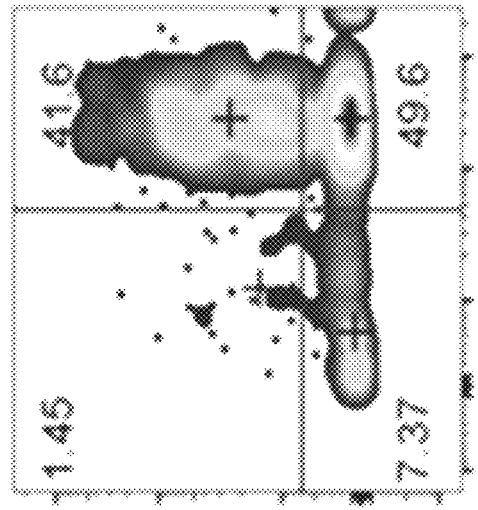

In escape mice (the 4 CAAR treated mice that had delayed outgrowth of AK19), the recovered AK19 cells were mostly surface immunoglobulin negative, indicating effective elimination of target (anti-Dsg3 IgG+) cells (FIG. 28). AK19 hybridomas were labeled with GFP and click beetle green luciferase prior to in vivo injection, which allowed the determination of whether the AK19 cells remained sIg+. 1e6 bone marrow cells were stained with saturating amounts of anti-mouse IgG1-APC. 41.6+49.6=91.2% of cultured AK19 hybridoma cells were sIg+ (left panel). 6/8 co-injected mice showed a pattern like 9382, with few detectable GFP+ cells. 9406 and 9407 (escape mice) showed GFP+ cells that had reduced or no surface IgG expression.

Figure 29:
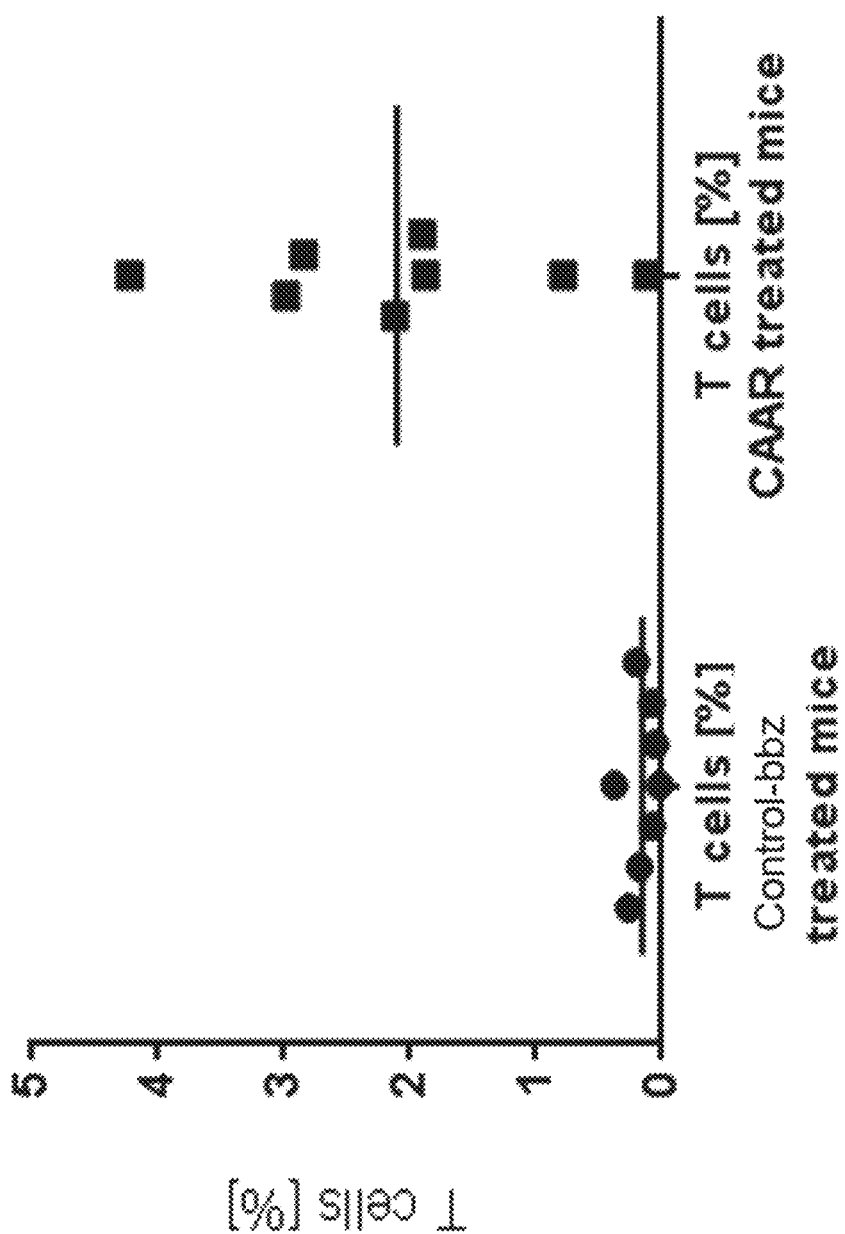
FIG. 29 is a graph showing the presence and engraftment of Dsg3 CAAR T cells transplanted into mice.
Figure 30A:
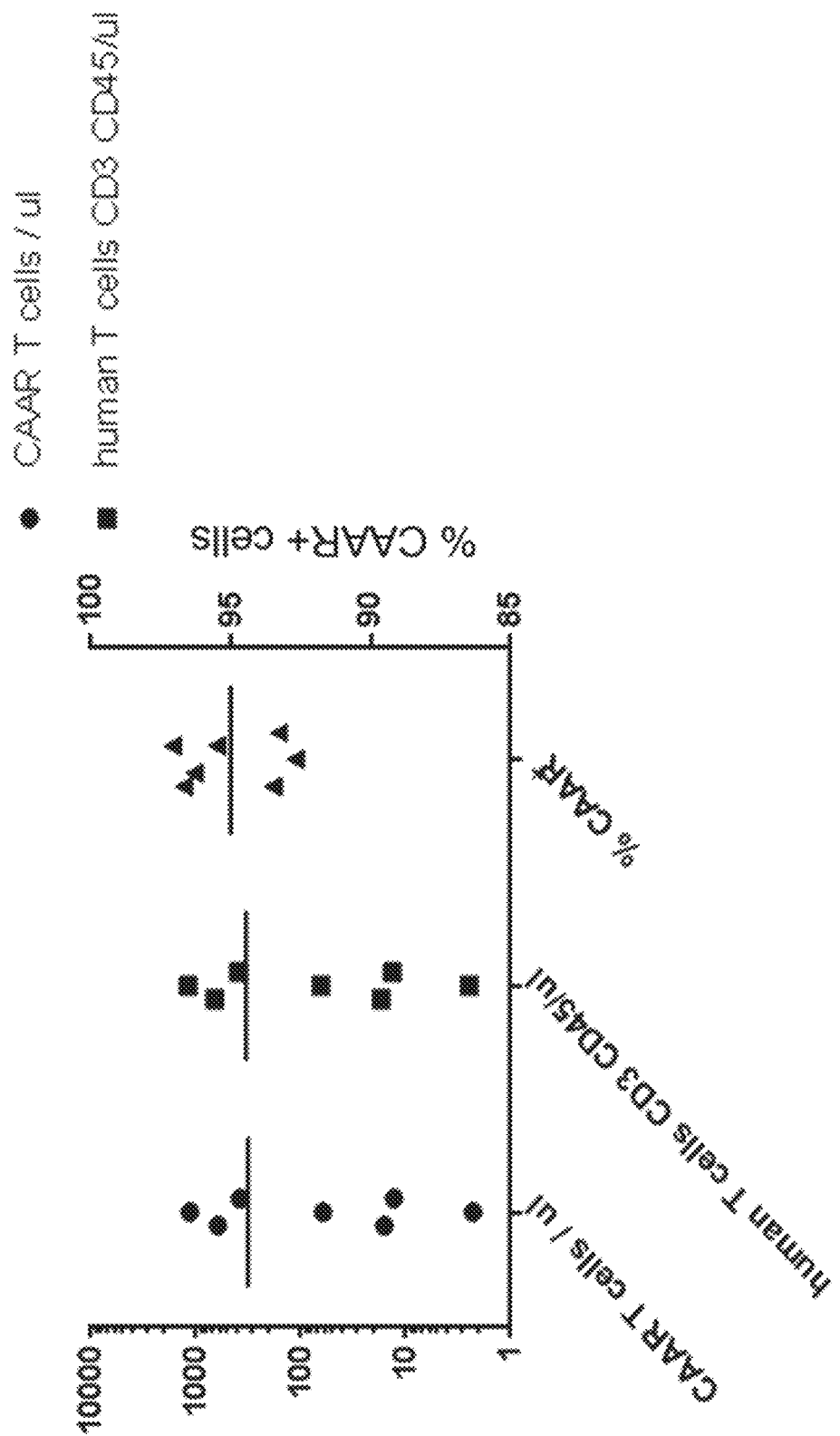
FIG. 30A is a graph showing presence of Dsg3 CAAR T cells in blood.
Figure 30B:
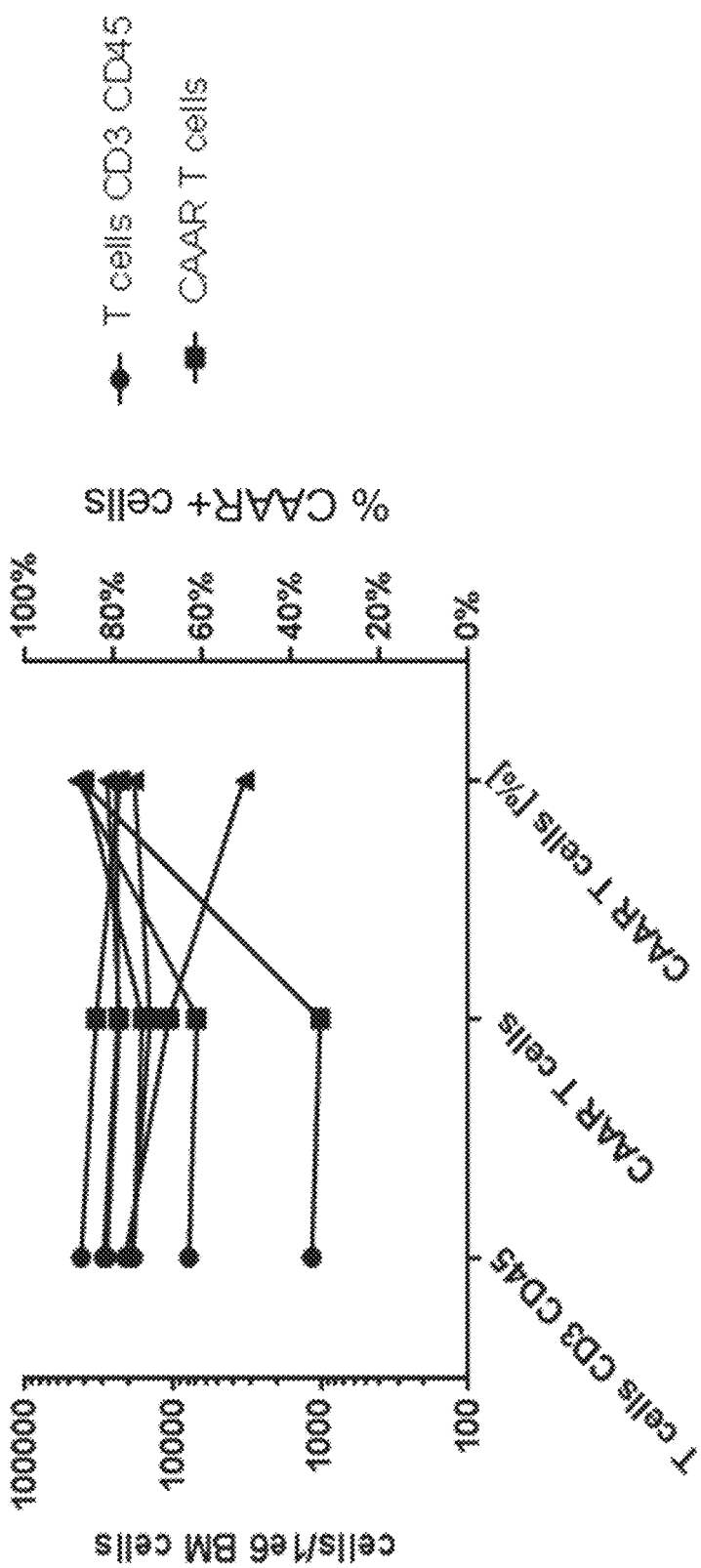
FIG. 30B is a graph showing presence of Dsg3 CAAR T cells in bone marrow.
Figure 30C:
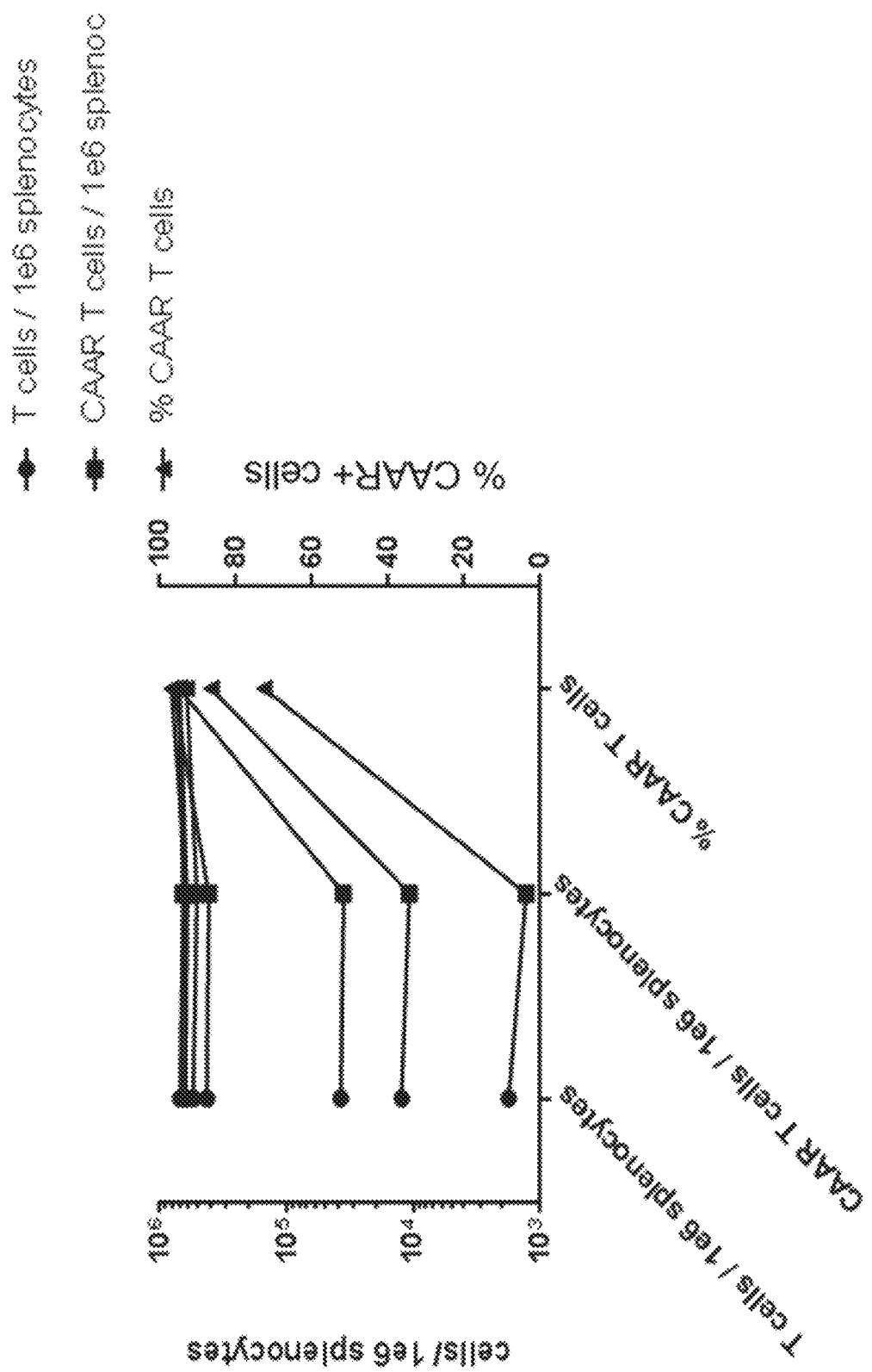
FIG. 30C is a graph showing presence of Dsg3 CAAR T cells in spleen.

Dsg3 CAAR T cells further engrafted and maintained long-term CAAR expression (FIG. 29). In fact, significant expansion of the cells was observed as compared to control CAR T cells. Percent of human T cells in mouse bone marrow (BM):control CAR versus Dsg3 CAAR FIGS. 30A-C show the presence of Dsg3 CAAR T cells that engrafted in different immunological compartments, blood (FIG. 30A), bone marrow (FIG. 30B), and spleen (FIG. 30C).

Figure 31:
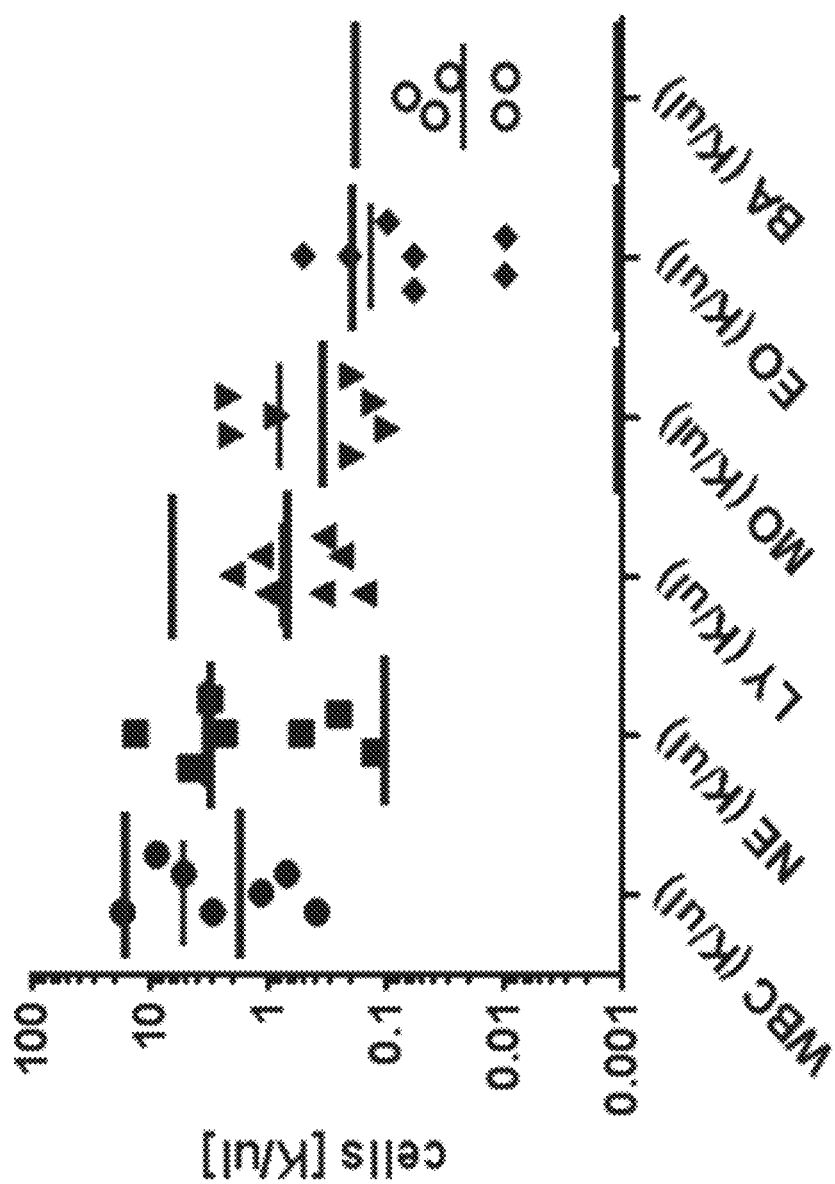
FIG. 31 is a graph showing that Dsg CAAR T cells did not cause rADCC against FcgammaR-expressing neutrophils and monocytes in vivo. Reference values are indicated by horizontal lines. NSG mice do not have B, T lymphocytes/ NK cells.

Shown in FIG. 31 is the complete blood count from 7 CAAR treated mice 35 days after CAAR injection. No depletion of Fc-receptor bearing cells was detected (NE=neutrophils, MO=monocytes). In vivo efficacy of the Dsg3 EC1-4 CAAR and Dsg3 EC1-3 CAAR was shown against AK23 (anti-EC1).

Figure 32A:
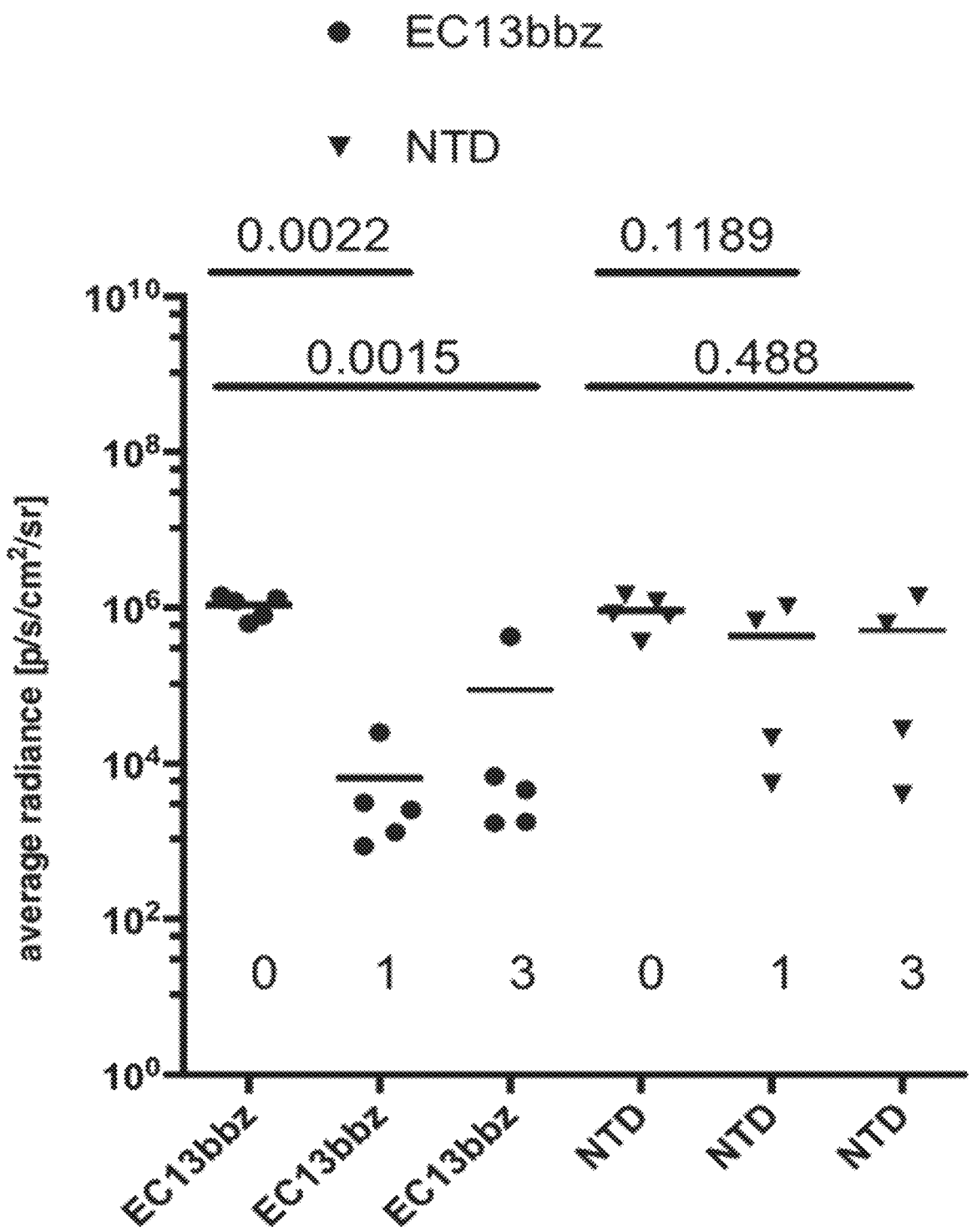
FIG. 32A is a graph showing bioluminescence of AK23 tumor burden in Dsg3 EC1-3 CAART injected mice.
Figure 32B:
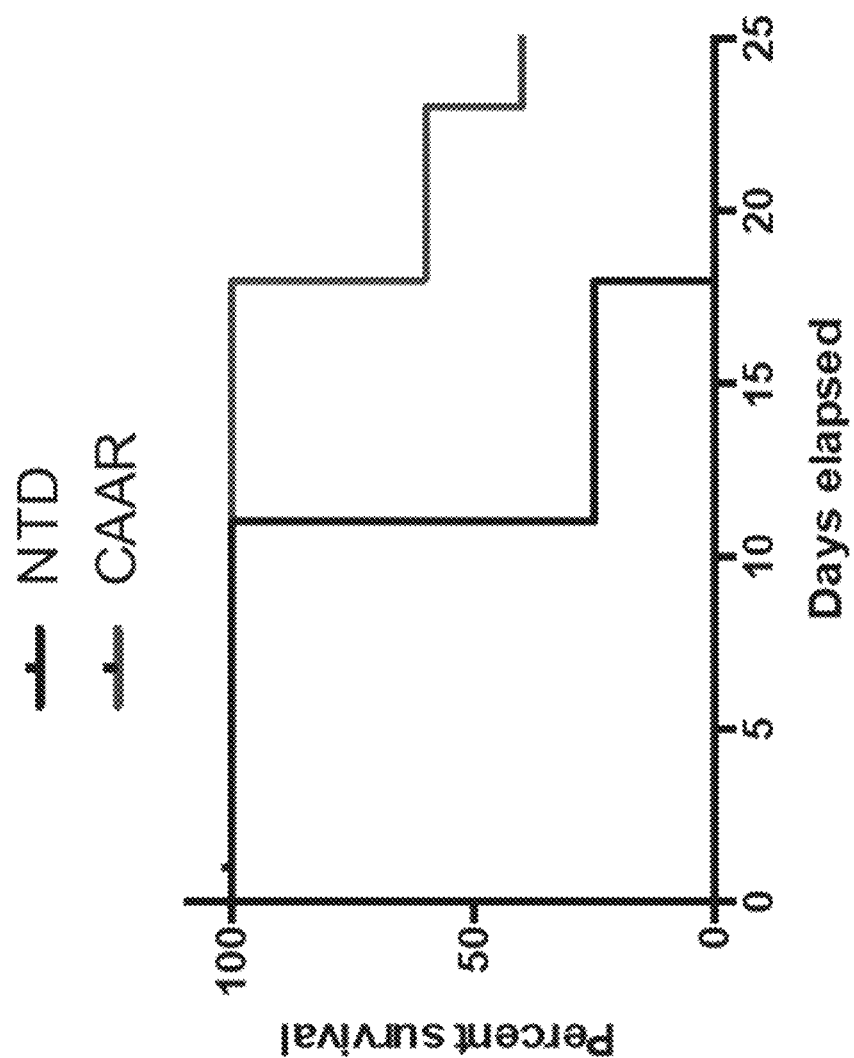
FIG. 32B is a graph showing survival of control and Dsg3 EC1-3 CAART injected AK23 tumor bearing mice.
Figure 33:
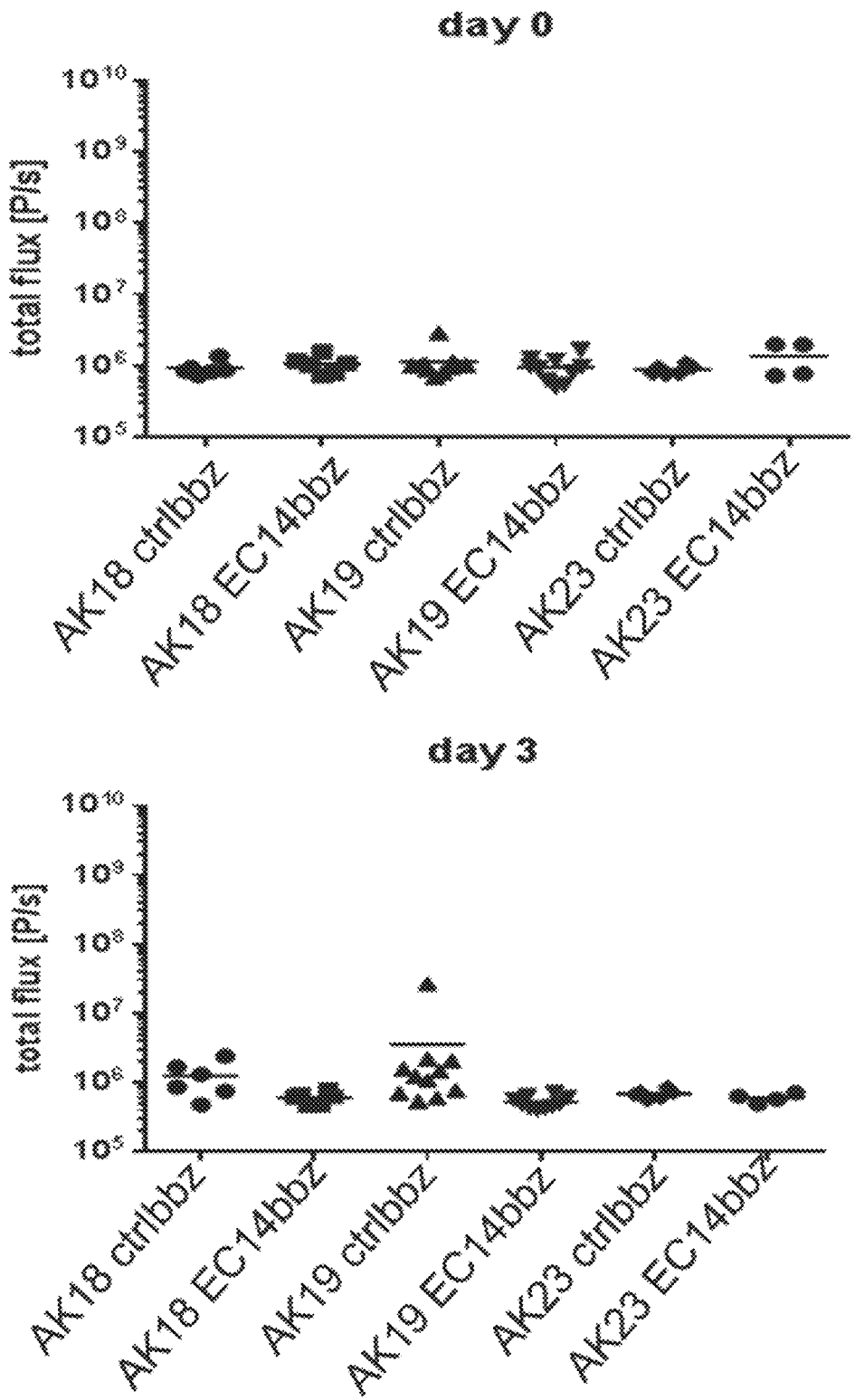
FIG. 33 is a panel of graphs showing that Dsg3 EC1-4 CAAR T cells exhibit efficacy against a broad range of targets in vivo (bioluminescence imaging days 0-3 after injection).
Figure 34:
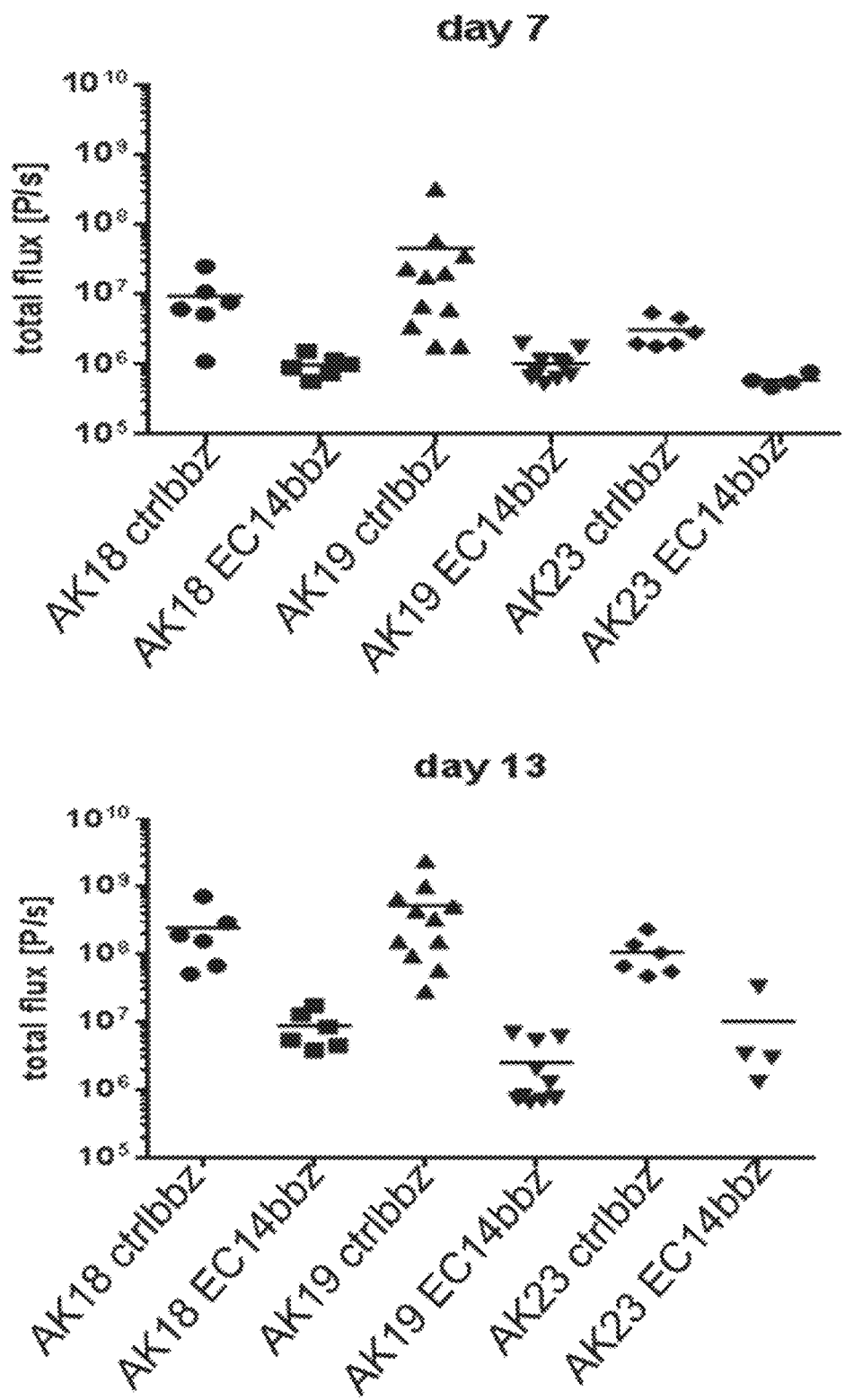
FIG. 34 is a panel of graphs showing Dsg3 EC1-4 CAAR T cells exhibit efficacy against a broad range of targets in vivo (bioluminescence imaging days 7-13 after injection).
Figure 35:
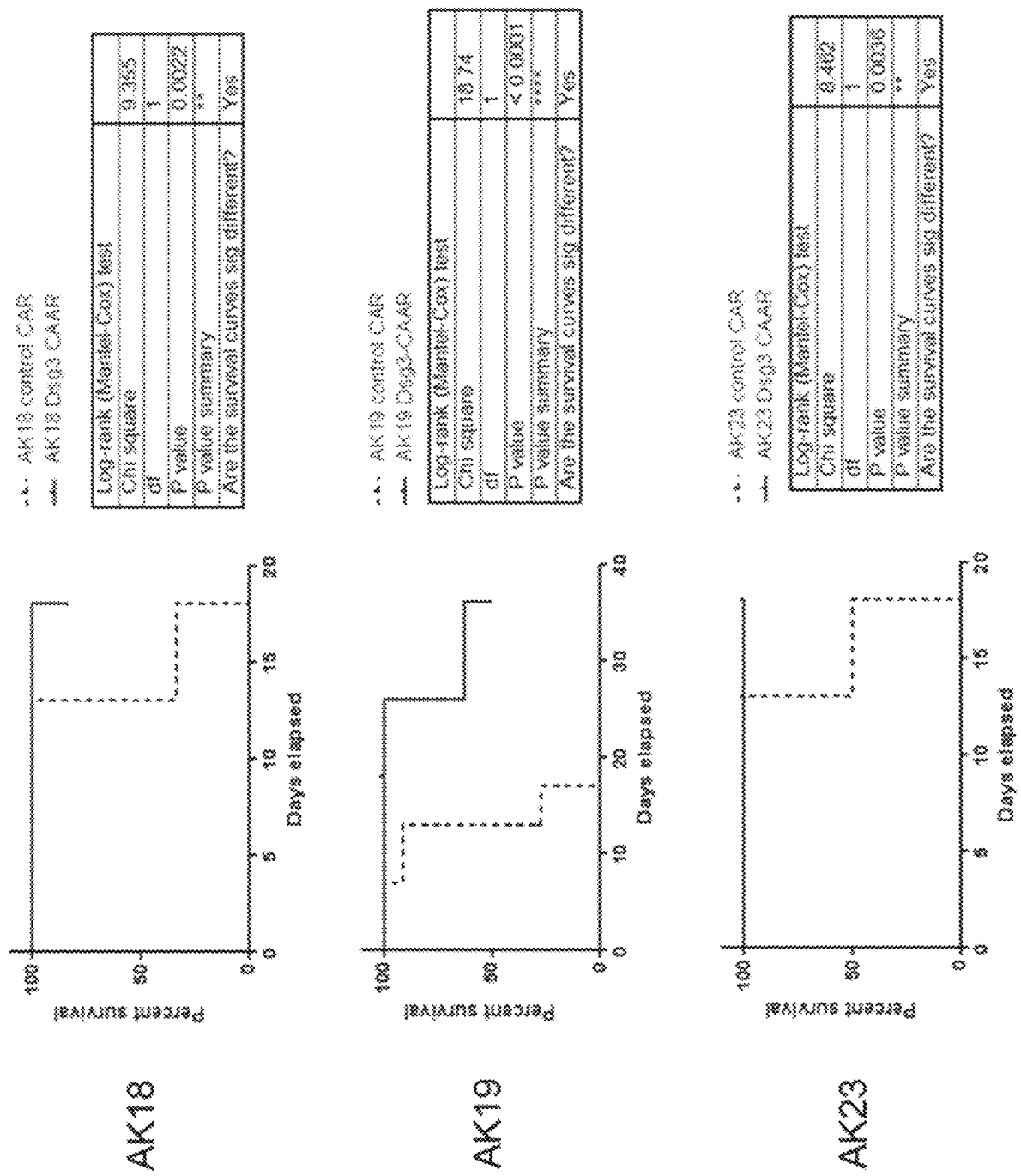
FIG. 35 is a panel of graphs showing Dsg3 EC1-4 CAAR T cells exhibit efficacy against a broad range of targets in vivo, based on survival curves with total flux of 10E8 defined as death.

Dsg3 EC1-3 CAAR further reduced AK23 tumor burden by bioluminescence (FIG. 32A) and increased survival (FIG. 32B). Potentially similar to AK19, mice that escape the Dsg3 EC1-3 CAAR may be selected for negative surface immunoglobulin AK23 cells. FIGS. 33-35 further show that Dsg3 EC1-4 CAAR T cells show efficacy against a broad range of targets in vivo, including AK18 (anti-EC3), AK19 (anti-EC2), and AK23 (anti-EC1), as evidenced by decreased bioluminescence in Dsg3 CAART-versus control CART-treated mice and increased survival of Dsg3 CAART-treated mice.

In summary, a Dsg3 CAAR has been developed that shows specific binding, activation by, and killing of cells expressing surface anti-Dsg3 IgG (efficacy). The Dsg3 CAAR does not activate in response to keratinocytes expressing Dsg3, or cells expressing Fc receptors that may bind serum anti-Dsg3 IgG (safety). Furthermore, the Dsg3 CAAR is a novel and specific strategy to target only the autoreactive B cells in PV and could be used as a proof of principle for the therapeutic use of CAARs in other autoantibody-mediated diseases.

Figure 36:
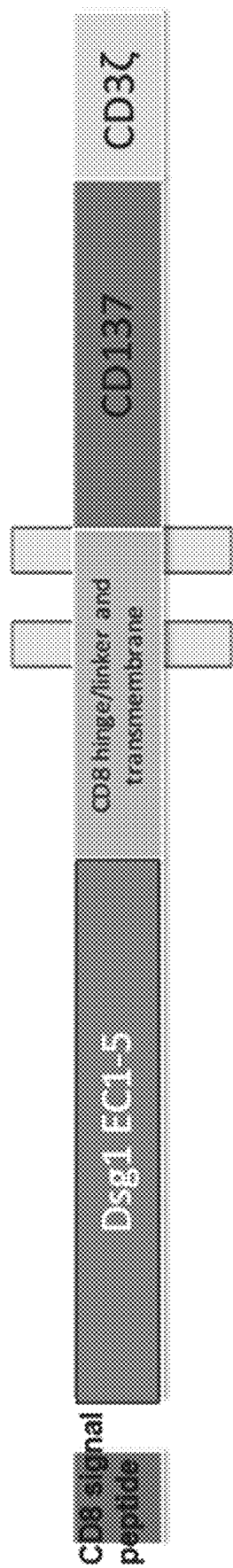
FIG. 36 is a schematic drawing of the protein domains comprising a desmoglein 1 (Dsg1) chimeric autoantibody receptor (CAAR).
Figure 37A:
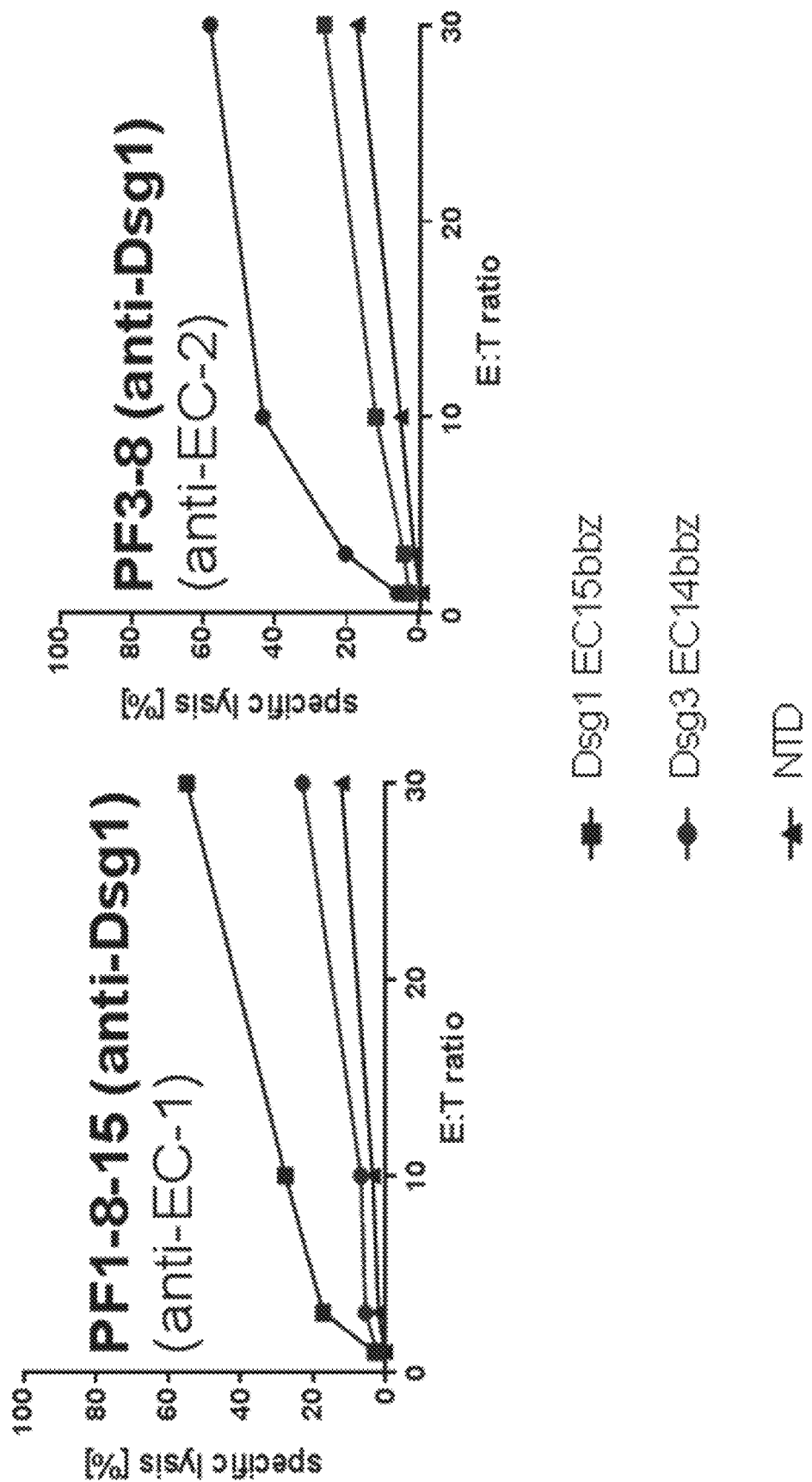
FIG. 37A is a panel of graphs showing killing of two different anti-Dsg1 cells by Dsg1 CAART cells by targeting both EC1 and EC2 domains.
Figure 37B:
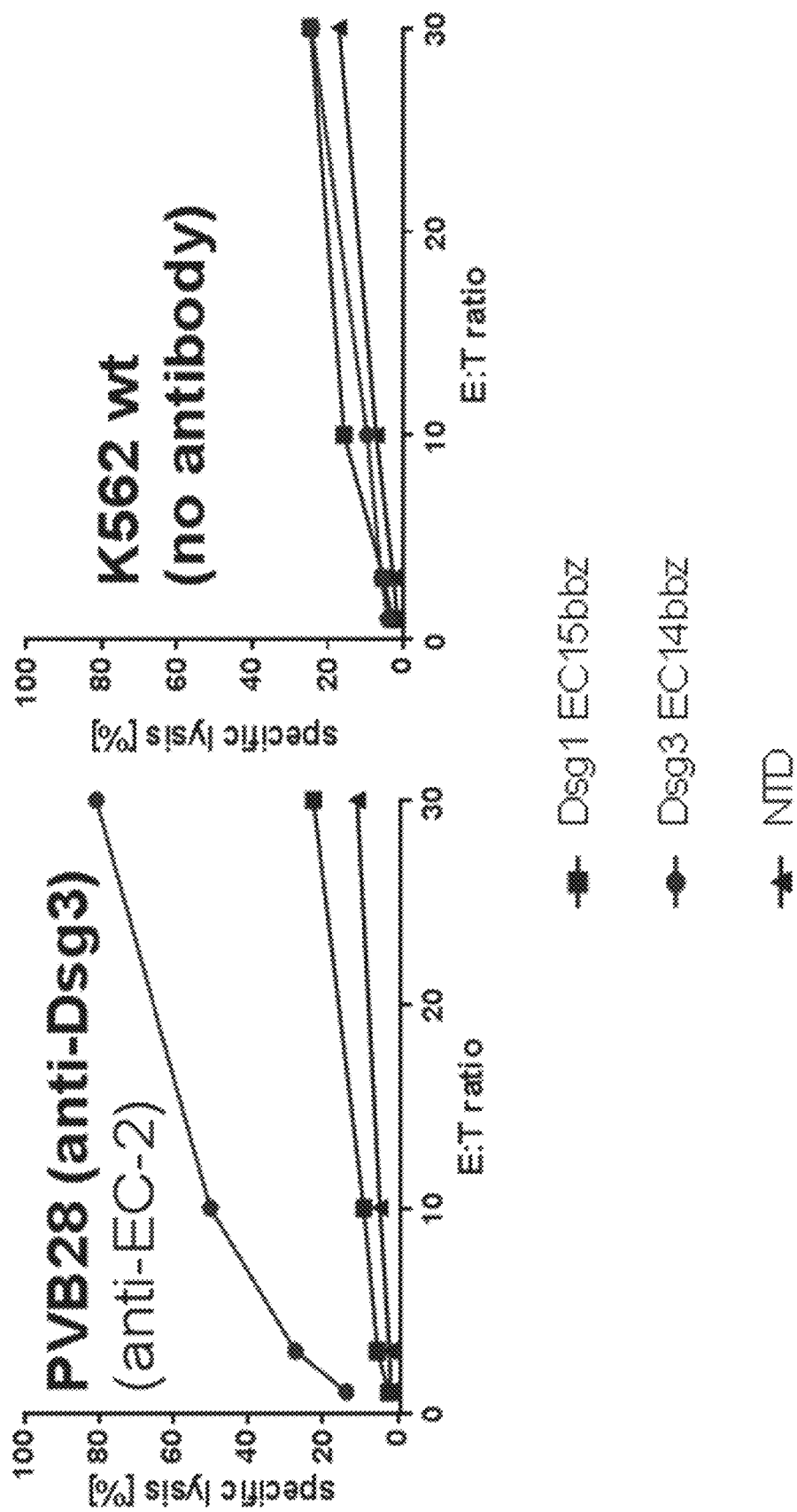
FIG. 37B is a panel of graphs showing that Dsg1 CAART cells do not non-specifically kill wild type K562 cells or K562 cells expressing anti-Dsg3 antibody PVB28.

To test if CAAR cells can be engineered with Dsg1 and be as effective at killing as Dsg3 CAAR cells, a CAAR construct including Dsg1 was generated (FIG. 36). Based on results optimizating the Dsg3 CAAR, a Dsg1 CAAR was constructed consisting of EC1-5 domains of Dsg1 for the CAAR extracellular domain. K562 cells were engineered to express monoclonal surface IgG with Dsg1 EC1 or Dsg1 EC2 specificities. After 16 hrs in a $^{51}$Chromium release assay, Dsg1 CAAR cells effectively killed anti-EC1 and anti-EC2 B cells, see FIG. 37A, but did not kill wild type K562 cells or K562 cells expressing anti-Dsg3 antibodies (FIG. 37B).

Figure 38:
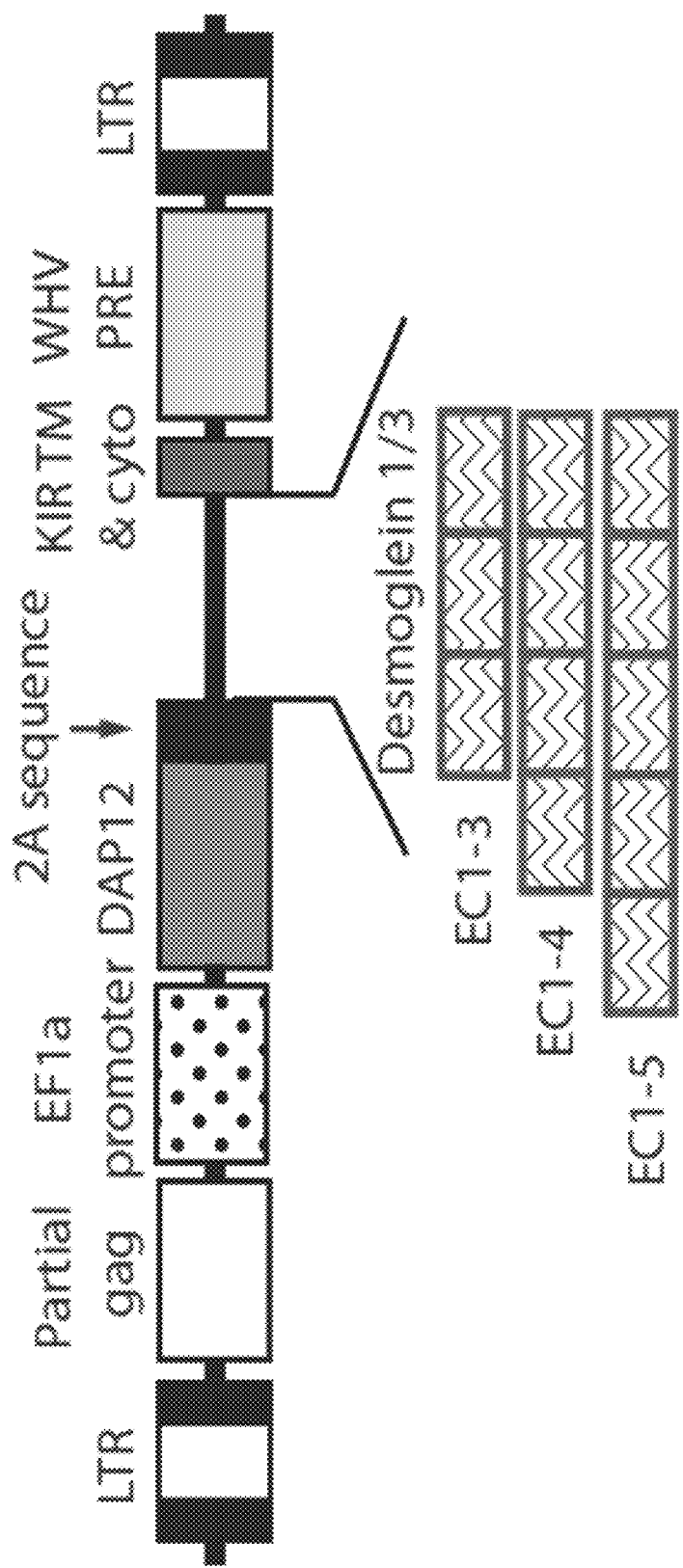
FIG. 38 is a schematic drawing of the KIR domains in a desmoglein 1 or 3 chimeric autoantibody receptor (CAAR).

To test if Dsg1 or Dsg3 CAARs engineered with KIR domains are effective at killing target cells, a CAAR construct including KIR transmembrane and cytoplasmic domains was generated (FIG. 38). Based on results optimizating the Dsg3 CAAR, a Dsg3 KIR CAAR was constructed consisting of EC1-3 or EC1-4 domains of Dsg3 with KIR transmembrane and cytoplasmic domains. PVB28 cells express anti-Dsg3 antibodies. After 16 hrs in a $^{51}$Chromium release assay, Dsg3 KIRCAAR cells effectively killed anti-EC2 B cells (FIG. 39A) and not control cells (not expressing anti-Dsg3 antibodies), (FIG. 39B). The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A chimeric receptor comprising an extracellular domain comprising Dsg1, Dsg3, or a fragment thereof that binds an autoantibody expressed on a B-cell, and a transmembrane domain, wherein the chimeric receptor, when present on the surface of a cell, binds the autoantibody expressed on the B-cell or induces killing of the B-cell expressing the autoantibody.

2. The chimeric receptor of claim 1, wherein the cell is selected from the group consisting of a helper T cell, a cytotoxic T cell, a memory cell, a regulatory T cell, a gamma delta T cell, a natural killer cell, a cytokine induced killer cell, and a cell line thereof.

3. The chimeric receptor of claim 1, wherein the extracellular domain comprises Dsg3 or a fragment thereof.

4. The chimeric receptor of claim 3, wherein the extracellular domain comprises an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, or an amino acid sequence encoded by the nucleotide sequence of SEQ ID NO:36.

5. The chimeric receptor of claim 1, wherein the chimeric receptor further comprises a CD8 alpha chain signal peptide.

6. The chimeric receptor of claim 5, wherein the CD8 alpha chain signal peptide comprises the amino acid sequence of SEQ ID NO:1.

7. The chimeric receptor of claim 1, wherein the extracellular domain comprises Dsg3 or a fragment thereof and the chimeric receptor further comprises a propeptide of Dsg3.

8. The chimeric receptor of claim 1, wherein the transmembrane domain comprises a KIR transmembrane domain.

9. The chimeric receptor of claim 1, wherein the transmembrane domain comprises a CD8 alpha chain hinge and transmembrane domain.

10. The chimeric receptor of claim 9, wherein the CD8 alpha chain hinge and transmembrane domain comprises the amino acid sequence of SEQ ID NO:13.

11. The chimeric receptor of claim 1, wherein the chimeric receptor further comprises a peptide linker.

12. The chimeric receptor of claim 11, wherein the peptide linker comprises the amino acid sequence of SEQ ID NO:14.

13. The chimeric receptor of claim 1, wherein the chimeric receptor further comprises a KIR cytoplasmic domain.

14. The chimeric receptor of claim 1, wherein the chimeric receptor further comprises an intracellular signaling domain.

15. The chimeric receptor of claim 14, wherein the intracellular signaling domain comprises a CD137 intracellular domain.

16. The chimeric receptor of claim 15, wherein the CD137 intracellular domain comprises the amino acid sequence of SEQ ID NO:15.

17. The chimeric receptor of claim 15, wherein the intracellular signaling domain comprises a CD3 zeta signaling domain.

18. The chimeric receptor of claim 17, wherein the CD3 zeta signaling domain comprises the amino acid sequence of SEQ ID NO:16.

19. The chimeric receptor of claim 1, wherein the chimeric receptor, when present on the surface of a cell, has limited toxicity toward a healthy cell.

* * * * *

SEQUENCE LISTING

```
<160> NUMBER OF SEQ ID NOS: 42

<210> SEQ ID NO 1
<211> LENGTH: 21
<212> TYPE: PRT
<213> ORGANISM: Artificial Sequence
<220> FEATURE:
<223> OTHER INFORMATION: Synthetic sequence

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 26
<212> TYPE: PRT
<213> ORGANISM: Homo sapiens

<400> SEQUENCE: 2

Glu Leu Arg Ile Glu Thr Lys Gly Gln Tyr Asp Glu Glu Met Thr
1               5                   10                  15

Met Gln Gln Ala Lys Arg Arg Gln Lys Arg
            20                  25

<210> SEQ ID NO 3
<211> LENGTH: 566
<212> TYPE: PRT
<213> ORGANISM: Homo sapiens

<400> SEQUENCE: 3

Glu Trp Val Lys Phe Ala Lys Pro Cys Arg Glu Gly Glu Asp Asn Ser
1               5                   10                  15
```

```
Lys Arg Asn Pro Ile Ala Lys Ile Thr Ser Asp Tyr Gln Ala Thr Gln
                 20                  25                  30

Lys Ile Thr Tyr Arg Ile Ser Gly Val Gly Ile Asp Gln Pro Pro Phe
             35                  40                  45

Gly Ile Phe Val Val Asp Lys Asn Thr Gly Asp Ile Asn Ile Thr Ala
         50                  55                  60

Ile Val Asp Arg Glu Glu Thr Pro Ser Phe Leu Ile Thr Cys Arg Ala
65                  70                  75                  80

Leu Asn Ala Gln Gly Leu Asp Val Glu Lys Pro Leu Ile Leu Thr Val
                 85                  90                  95

Lys Ile Leu Asp Ile Asn Asp Asn Pro Pro Val Phe Ser Gln Gln Ile
             100                 105                 110

Phe Met Gly Glu Ile Glu Glu Asn Ser Ala Ser Asn Ser Leu Val Met
         115                 120                 125

Ile Leu Asn Ala Thr Asp Ala Asp Glu Pro Asn His Leu Asn Ser Lys
    130                 135                 140

Ile Ala Phe Lys Ile Val Ser Gln Glu Pro Ala Gly Thr Pro Met Phe
145                 150                 155                 160

Leu Leu Ser Arg Asn Thr Gly Glu Val Arg Thr Leu Thr Asn Ser Leu
                 165                 170                 175

Asp Arg Glu Gln Ala Ser Ser Tyr Arg Leu Val Val Ser Gly Ala Asp
             180                 185                 190

Lys Asp Gly Glu Gly Leu Ser Thr Gln Cys Glu Cys Asn Ile Lys Val
         195                 200                 205

Lys Asp Val Asn Asp Asn Phe Pro Met Phe Arg Asp Ser Gln Tyr Ser
210                 215                 220

Ala Arg Ile Glu Glu Asn Ile Leu Ser Ser Glu Leu Leu Arg Phe Gln
225                 230                 235                 240

Val Thr Asp Leu Asp Glu Glu Tyr Thr Asp Asn Trp Leu Ala Val Tyr
                 245                 250                 255

Phe Phe Thr Ser Gly Asn Glu Gly Asn Trp Phe Glu Ile Gln Thr Asp
             260                 265                 270

Pro Arg Thr Asn Glu Gly Ile Leu Lys Val Val Lys Ala Leu Asp Tyr
         275                 280                 285

Glu Gln Leu Gln Ser Val Lys Leu Ser Ile Ala Val Lys Asn Lys Ala
290                 295                 300

Glu Phe His Gln Ser Val Ile Ser Arg Tyr Arg Val Gln Ser Thr Pro
305                 310                 315                 320

Val Thr Ile Gln Val Ile Asn Val Arg Glu Gly Ile Ala Phe Arg Pro
                 325                 330                 335

Ala Ser Lys Thr Phe Thr Val Gln Lys Gly Ile Ser Ser Lys Lys Leu
             340                 345                 350

Val Asp Tyr Ile Leu Gly Thr Tyr Gln Ala Ile Asp Glu Asp Thr Asn
         355                 360                 365

Lys Ala Ala Ser Asn Val Lys Tyr Val Met Gly Arg Asn Asp Gly Gly
370                 375                 380

Tyr Leu Met Ile Asp Ser Lys Thr Ala Glu Ile Lys Phe Val Lys Asn
385                 390                 395                 400

Met Asn Arg Asp Ser Thr Phe Ile Val Asn Lys Thr Ile Thr Ala Glu
                 405                 410                 415

Val Leu Ala Ile Asp Glu Tyr Thr Gly Lys Thr Ser Thr Gly Thr Val
             420                 425                 430

Tyr Val Arg Val Pro Asp Phe Asn Asp Asn Cys Pro Thr Ala Val Leu
```

```
                    435                 440                 445
Glu Lys Asp Ala Val Cys Ser Ser Pro Ser Val Val Ser Ala
450                 455                 460

Arg Thr Leu Asn Asn Arg Tyr Thr Gly Pro Tyr Thr Phe Ala Leu Glu
465                 470                 475                 480

Asp Gln Pro Val Lys Leu Pro Ala Val Trp Ser Ile Thr Thr Leu Asn
                485                 490                 495

Ala Thr Ser Ala Leu Leu Arg Ala Gln Glu Gln Ile Pro Pro Gly Val
            500                 505                 510

Tyr His Ile Ser Leu Val Leu Thr Asp Ser Gln Asn Asn Arg Cys Glu
            515                 520                 525

Met Pro Arg Ser Leu Thr Leu Glu Val Cys Gln Cys Asp Asn Arg Gly
        530                 535                 540

Ile Cys Gly Thr Ser Tyr Pro Thr Thr Ser Pro Gly Thr Arg Tyr Gly
545                 550                 555                 560

Arg Pro His Ser Gly Arg
                565
```

<210> SEQ ID NO 4
<211> LENGTH: 237
<212> TYPE: PRT
<213> ORGANISM: Homo sapiens

<400> SEQUENCE: 4

```
Glu Trp Val Lys Phe Ala Lys Pro Cys Arg Glu Gly Glu Asp Asn Ser
1               5                   10                  15

Lys Arg Asn Pro Ile Ala Lys Ile Thr Ser Asp Tyr Gln Ala Thr Gln
            20                  25                  30

Lys Ile Thr Tyr Arg Ile Ser Gly Val Gly Ile Asp Gln Pro Pro Phe
        35                  40                  45

Gly Ile Phe Val Val Asp Lys Asn Thr Gly Asp Ile Asn Ile Thr Ala
    50                  55                  60

Ile Val Asp Arg Glu Glu Thr Pro Ser Phe Leu Ile Thr Cys Arg Ala
65                  70                  75                  80

Leu Asn Ala Gln Gly Leu Asp Val Glu Lys Pro Leu Ile Leu Thr Val
                85                  90                  95

Lys Ile Leu Asp Ile Asn Asp Asn Pro Pro Val Phe Ser Gln Gln Ile
            100                 105                 110

Phe Met Gly Glu Ile Glu Glu Asn Ser Ala Ser Asn Ser Leu Val Met
        115                 120                 125

Ile Leu Asn Ala Thr Asp Ala Asp Glu Pro Asn His Leu Asn Ser Lys
    130                 135                 140

Ile Ala Phe Lys Ile Val Ser Gln Glu Pro Ala Gly Thr Pro Met Phe
145                 150                 155                 160

Leu Leu Ser Arg Asn Thr Gly Glu Val Arg Thr Leu Thr Asn Ser Leu
                165                 170                 175

Asp Arg Glu Gln Ala Ser Ser Tyr Arg Leu Val Val Ser Gly Ala Asp
            180                 185                 190

Lys Asp Gly Glu Gly Leu Ser Thr Gln Cys Glu Cys Asn Ile Lys Val
        195                 200                 205

Lys Asp Val Asn Asp Asn Phe Pro Met Phe Arg Asp Ser Gln Tyr Ser
    210                 215                 220

Ala Arg Ile Glu Glu Asn Ile Leu Ser Ser Glu Leu Leu
225                 230                 235
```

<210> SEQ ID NO 5
<211> LENGTH: 334
<212> TYPE: PRT
<213> ORGANISM: Homo sapiens

<400> SEQUENCE: 5

Glu Trp Val Lys Phe Ala Lys Pro Cys Arg Glu Gly Glu Asp Asn Ser
1               5                   10                  15

Lys Arg Asn Pro Ile Ala Lys Ile Thr Ser Asp Tyr Gln Ala Thr Gln
            20                  25                  30

Lys Ile Thr Tyr Arg Ile Ser Gly Val Gly Ile Asp Gln Pro Pro Phe
        35                  40                  45

Gly Ile Phe Val Val Asp Lys Asn Thr Gly Asp Ile Asn Ile Thr Ala
    50                  55                  60

Ile Val Asp Arg Glu Glu Thr Pro Ser Phe Leu Ile Thr Cys Arg Ala
65                  70                  75                  80

Leu Asn Ala Gln Gly Leu Asp Val Glu Lys Pro Leu Ile Leu Thr Val
                85                  90                  95

Lys Ile Leu Asp Ile Asn Asp Asn Pro Pro Val Phe Ser Gln Gln Ile
            100                 105                 110

Phe Met Gly Glu Ile Glu Glu Asn Ser Ala Ser Asn Ser Leu Val Met
        115                 120                 125

Ile Leu Asn Ala Thr Asp Ala Asp Glu Pro Asn His Leu Asn Ser Lys
    130                 135                 140

Ile Ala Phe Lys Ile Val Ser Gln Glu Pro Ala Gly Thr Pro Met Phe
145                 150                 155                 160

Leu Leu Ser Arg Asn Thr Gly Glu Val Arg Thr Leu Thr Asn Ser Leu
                165                 170                 175

Asp Arg Glu Gln Ala Ser Ser Tyr Arg Leu Val Val Ser Gly Ala Asp
            180                 185                 190

Lys Asp Gly Glu Gly Leu Ser Thr Gln Cys Glu Cys Asn Ile Lys Val
        195                 200                 205

Lys Asp Val Asn Asp Asn Phe Pro Met Phe Arg Asp Ser Gln Tyr Ser
    210                 215                 220

Ala Arg Ile Glu Glu Asn Ile Leu Ser Ser Glu Leu Leu Arg Phe Gln
225                 230                 235                 240

Val Thr Asp Leu Asp Glu Glu Tyr Thr Asp Asn Trp Leu Ala Val Tyr
                245                 250                 255

Phe Phe Thr Ser Gly Asn Glu Gly Asn Trp Phe Glu Ile Gln Thr Asp
            260                 265                 270

Pro Arg Thr Asn Glu Gly Ile Leu Lys Val Val Lys Ala Leu Asp Tyr
        275                 280                 285

Glu Gln Leu Gln Ser Val Lys Leu Ser Ile Ala Val Lys Asn Lys Ala
    290                 295                 300

Glu Phe His Gln Ser Val Ile Ser Arg Tyr Arg Val Gln Ser Thr Pro
305                 310                 315                 320

Val Thr Ile Gln Val Ile Asn Val Arg Glu Gly Ile Ala Phe
                325                 330

<210> SEQ ID NO 6
<211> LENGTH: 450
<212> TYPE: PRT
<213> ORGANISM: Homo sapiens

<400> SEQUENCE: 6

```
Glu Trp Val Lys Phe Ala Lys Pro Cys Arg Gly Glu Asp Asn Ser
1               5                   10                  15

Lys Arg Asn Pro Ile Ala Lys Ile Thr Ser Asp Tyr Gln Ala Thr Gln
            20                  25                  30

Lys Ile Thr Tyr Arg Ile Ser Gly Val Gly Ile Asp Gln Pro Pro Phe
                35                  40                  45

Gly Ile Phe Val Val Asp Lys Asn Thr Gly Asp Ile Asn Ile Thr Ala
        50                  55                  60

Ile Val Asp Arg Glu Glu Thr Pro Ser Phe Leu Ile Thr Cys Arg Ala
65                  70                  75                  80

Leu Asn Ala Gln Gly Leu Asp Val Glu Lys Pro Leu Ile Leu Thr Val
                85                  90                  95

Lys Ile Leu Asp Ile Asn Asp Asn Pro Pro Val Phe Ser Gln Gln Ile
            100                 105                 110

Phe Met Gly Glu Ile Glu Glu Asn Ser Ala Ser Asn Ser Leu Val Met
            115                 120                 125

Ile Leu Asn Ala Thr Asp Ala Asp Glu Pro Asn His Leu Asn Ser Lys
        130                 135                 140

Ile Ala Phe Lys Ile Val Ser Gln Glu Pro Ala Gly Thr Pro Met Phe
145                 150                 155                 160

Leu Leu Ser Arg Asn Thr Gly Glu Val Arg Thr Leu Thr Asn Ser Leu
                165                 170                 175

Asp Arg Glu Gln Ala Ser Ser Tyr Arg Leu Val Val Ser Gly Ala Asp
            180                 185                 190

Lys Asp Gly Glu Gly Leu Ser Thr Gln Cys Glu Cys Asn Ile Lys Val
            195                 200                 205

Lys Asp Val Asn Asp Asn Phe Pro Met Phe Arg Asp Ser Gln Tyr Ser
210                 215                 220

Ala Arg Ile Glu Glu Asn Ile Leu Ser Ser Glu Leu Leu Arg Phe Gln
225                 230                 235                 240

Val Thr Asp Leu Asp Glu Glu Tyr Thr Asp Asn Trp Leu Ala Val Tyr
            245                 250                 255

Phe Phe Thr Ser Gly Asn Glu Gly Asn Trp Phe Glu Ile Gln Thr Asp
            260                 265                 270

Pro Arg Thr Asn Glu Gly Ile Leu Lys Val Val Lys Ala Leu Asp Tyr
            275                 280                 285

Glu Gln Leu Gln Ser Val Lys Leu Ser Ile Ala Val Lys Asn Lys Ala
290                 295                 300

Glu Phe His Gln Ser Val Ile Ser Arg Tyr Arg Val Gln Ser Thr Pro
305                 310                 315                 320

Val Thr Ile Gln Val Ile Asn Val Arg Glu Gly Ile Ala Phe Arg Pro
            325                 330                 335

Ala Ser Lys Thr Phe Thr Val Gln Lys Gly Ile Ser Ser Lys Lys Leu
            340                 345                 350

Val Asp Tyr Ile Leu Gly Thr Tyr Gln Ala Ile Asp Glu Asp Thr Asn
            355                 360                 365

Lys Ala Ala Ser Asn Val Lys Tyr Val Met Gly Arg Asn Asp Gly Gly
            370                 375                 380

Tyr Leu Met Ile Asp Ser Lys Thr Ala Glu Ile Lys Phe Val Lys Asn
385                 390                 395                 400

Met Asn Arg Asp Ser Thr Phe Ile Val Asn Lys Thr Ile Thr Ala Glu
            405                 410                 415

Val Leu Ala Ile Asp Glu Tyr Thr Gly Lys Thr Ser Thr Gly Thr Val
```

```
                    420                 425                 430
Tyr Val Arg Val Pro Asp Phe Asn Asp Asn Cys Pro Thr Ala Val Leu
                435                 440                 445
Glu Lys
    450

<210> SEQ ID NO 7
<211> LENGTH: 225
<212> TYPE: PRT
<213> ORGANISM: Homo sapiens

<400> SEQUENCE: 7

Gln Gln Ile Phe Met Gly Glu Ile Glu Glu Asn Ser Ala Ser Asn Ser
1               5                   10                  15

Leu Val Met Ile Leu Asn Ala Thr Asp Ala Asp Glu Pro Asn His Leu
            20                  25                  30

Asn Ser Lys Ile Ala Phe Lys Ile Val Ser Gln Glu Pro Ala Gly Thr
        35                  40                  45

Pro Met Phe Leu Leu Ser Arg Asn Thr Gly Glu Val Arg Thr Leu Thr
    50                  55                  60

Asn Ser Leu Asp Arg Glu Gln Ala Ser Ser Tyr Arg Leu Val Val Ser
65                  70                  75                  80

Gly Ala Asp Lys Asp Gly Glu Gly Leu Ser Thr Gln Cys Glu Cys Asn
                85                  90                  95

Ile Lys Val Lys Asp Val Asn Asp Asn Phe Pro Met Phe Arg Asp Ser
            100                 105                 110

Gln Tyr Ser Ala Arg Ile Glu Glu Asn Ile Leu Ser Ser Glu Leu Leu
        115                 120                 125

Arg Phe Gln Val Thr Asp Leu Asp Glu Glu Tyr Thr Asp Asn Trp Leu
    130                 135                 140

Ala Val Tyr Phe Phe Thr Ser Gly Asn Glu Gly Asn Trp Phe Glu Ile
145                 150                 155                 160

Gln Thr Asp Pro Arg Thr Asn Glu Gly Ile Leu Lys Val Val Lys Ala
                165                 170                 175

Leu Asp Tyr Glu Gln Leu Gln Ser Val Lys Leu Ser Ile Ala Val Lys
            180                 185                 190

Asn Lys Ala Glu Phe His Gln Ser Val Ile Ser Arg Tyr Arg Val Gln
        195                 200                 205

Ser Thr Pro Val Thr Ile Gln Val Ile Asn Val Arg Glu Gly Ile Ala
    210                 215                 220

Phe
225

<210> SEQ ID NO 8
<211> LENGTH: 231
<212> TYPE: PRT
<213> ORGANISM: Homo sapiens

<400> SEQUENCE: 8

Asp Ser Gln Tyr Ser Ala Arg Ile Glu Glu Asn Ile Leu Ser Ser Glu
1               5                   10                  15

Leu Leu Arg Phe Gln Val Thr Asp Leu Asp Glu Glu Tyr Thr Asp Asn
            20                  25                  30

Trp Leu Ala Val Tyr Phe Phe Thr Ser Gly Asn Glu Gly Asn Trp Phe
        35                  40                  45

Glu Ile Gln Thr Asp Pro Arg Thr Asn Glu Gly Ile Leu Lys Val Val
```

```
            50                  55                  60
Lys Ala Leu Asp Tyr Glu Gln Leu Gln Ser Val Lys Leu Ser Ile Ala
 65                  70                  75                  80

Val Lys Asn Lys Ala Glu Phe His Gln Ser Val Ile Ser Arg Tyr Arg
                 85                  90                  95

Val Gln Ser Thr Pro Val Thr Ile Gln Val Ile Asn Val Arg Glu Gly
                100                 105                 110

Ile Ala Phe Arg Pro Ala Ser Lys Thr Phe Thr Val Gln Lys Gly Ile
            115                 120                 125

Ser Ser Lys Lys Leu Val Asp Tyr Ile Leu Gly Thr Tyr Gln Ala Ile
        130                 135                 140

Asp Glu Asp Thr Asn Lys Ala Ala Ser Asn Val Lys Tyr Val Met Gly
145                 150                 155                 160

Arg Asn Asp Gly Gly Tyr Leu Met Ile Asp Ser Lys Thr Ala Glu Ile
                165                 170                 175

Lys Phe Val Lys Asn Met Asn Arg Asp Ser Thr Phe Ile Val Asn Lys
            180                 185                 190

Thr Ile Thr Ala Glu Val Leu Ala Ile Asp Glu Tyr Thr Gly Lys Thr
        195                 200                 205

Ser Thr Gly Thr Val Tyr Val Arg Val Pro Asp Phe Asn Asp Asn Cys
    210                 215                 220

Pro Thr Ala Val Leu Glu Lys
225                 230

<210> SEQ ID NO 9
<211> LENGTH: 230
<212> TYPE: PRT
<213> ORGANISM: Homo sapiens

<400> SEQUENCE: 9

Ala Ser Lys Thr Phe Thr Val Gln Lys Gly Ile Ser Ser Lys Lys Leu
 1               5                  10                  15

Val Asp Tyr Ile Leu Gly Thr Tyr Gln Ala Ile Asp Glu Asp Thr Asn
                20                  25                  30

Lys Ala Ala Ser Asn Val Lys Tyr Val Met Gly Arg Asn Asp Gly Gly
            35                  40                  45

Tyr Leu Met Ile Asp Ser Lys Thr Ala Glu Ile Lys Phe Val Lys Asn
        50                  55                  60

Met Asn Arg Asp Ser Thr Phe Ile Val Asn Lys Thr Ile Thr Ala Glu
 65                  70                  75                  80

Val Leu Ala Ile Asp Glu Tyr Thr Gly Lys Thr Ser Thr Gly Thr Val
                85                  90                  95

Tyr Val Arg Val Pro Asp Phe Asn Asp Asn Cys Pro Thr Ala Val Leu
            100                 105                 110

Glu Lys Asp Ala Val Cys Ser Ser Pro Ser Val Val Ser Ala
        115                 120                 125

Arg Thr Leu Asn Asn Arg Tyr Thr Gly Pro Tyr Thr Phe Ala Leu Glu
        130                 135                 140

Asp Gln Pro Val Lys Leu Pro Ala Val Trp Ser Ile Thr Thr Leu Asn
145                 150                 155                 160

Ala Thr Ser Ala Leu Leu Arg Ala Gln Glu Gln Ile Pro Pro Gly Val
                165                 170                 175

Tyr His Ile Ser Leu Val Leu Thr Asp Ser Gln Asn Asn Arg Cys Glu
            180                 185                 190
```

Met Pro Arg Ser Leu Thr Leu Glu Val Cys Gln Cys Asp Asn Arg Gly
            195                 200                 205

Ile Cys Gly Thr Ser Tyr Pro Thr Thr Ser Pro Gly Thr Arg Tyr Gly
    210                 215                 220

Arg Pro His Ser Gly Arg
225                 230

<210> SEQ ID NO 10
<211> LENGTH: 341
<212> TYPE: PRT
<213> ORGANISM: Homo sapiens

<400> SEQUENCE: 10

Gln Gln Ile Phe Met Gly Glu Ile Glu Asn Ser Ala Ser Asn Ser
1               5                   10                  15

Leu Val Met Ile Leu Asn Ala Thr Asp Ala Asp Glu Pro Asn His Leu
                20                  25                  30

Asn Ser Lys Ile Ala Phe Lys Ile Val Ser Gln Glu Pro Ala Gly Thr
            35                  40                  45

Pro Met Phe Leu Leu Ser Arg Asn Thr Gly Glu Val Arg Thr Leu Thr
50                  55                  60

Asn Ser Leu Asp Arg Glu Gln Ala Ser Ser Tyr Arg Leu Val Val Ser
65                  70                  75                  80

Gly Ala Asp Lys Asp Gly Glu Gly Leu Ser Thr Gln Cys Glu Cys Asn
                85                  90                  95

Ile Lys Val Lys Asp Val Asn Asp Asn Phe Pro Met Phe Arg Asp Ser
            100                 105                 110

Gln Tyr Ser Ala Arg Ile Glu Glu Asn Ile Leu Ser Ser Glu Leu Leu
        115                 120                 125

Arg Phe Gln Val Thr Asp Leu Asp Glu Glu Tyr Thr Asp Asn Trp Leu
130                 135                 140

Ala Val Tyr Phe Phe Thr Ser Gly Asn Glu Gly Asn Trp Phe Glu Ile
145                 150                 155                 160

Gln Thr Asp Pro Arg Thr Asn Glu Gly Ile Leu Lys Val Val Lys Ala
                165                 170                 175

Leu Asp Tyr Glu Gln Leu Gln Ser Val Lys Leu Ser Ile Ala Val Lys
            180                 185                 190

Asn Lys Ala Glu Phe His Gln Ser Val Ile Ser Arg Tyr Arg Val Gln
        195                 200                 205

Ser Thr Pro Val Thr Ile Gln Val Ile Asn Val Arg Glu Gly Ile Ala
210                 215                 220

Phe Arg Pro Ala Ser Lys Thr Phe Thr Val Gln Lys Gly Ile Ser Ser
225                 230                 235                 240

Lys Lys Leu Val Asp Tyr Ile Leu Gly Thr Tyr Gln Ala Ile Asp Glu
                245                 250                 255

Asp Thr Asn Lys Ala Ala Ser Asn Val Lys Tyr Val Met Gly Arg Asn
            260                 265                 270

Asp Gly Gly Tyr Leu Met Ile Asp Ser Lys Thr Ala Glu Ile Lys Phe
        275                 280                 285

Val Lys Asn Met Asn Arg Asp Ser Thr Phe Ile Val Asn Lys Thr Ile
290                 295                 300

Thr Ala Glu Val Leu Ala Ile Asp Glu Tyr Thr Gly Lys Thr Ser Thr
305                 310                 315                 320

Gly Thr Val Tyr Val Arg Val Pro Asp Phe Asn Asp Asn Cys Pro Thr
                325                 330                 335

Ala Val Leu Glu Lys
            340

<210> SEQ ID NO 11
<211> LENGTH: 347
<212> TYPE: PRT
<213> ORGANISM: Homo sapiens

<400> SEQUENCE: 11

Asp Ser Gln Tyr Ser Ala Arg Ile Glu Glu Asn Ile Leu Ser Ser Glu
1               5                   10                  15

Leu Leu Arg Phe Gln Val Thr Asp Leu Asp Glu Glu Tyr Thr Asp Asn
            20                  25                  30

Trp Leu Ala Val Tyr Phe Phe Thr Ser Gly Asn Glu Gly Asn Trp Phe
        35                  40                  45

Glu Ile Gln Thr Asp Pro Arg Thr Asn Glu Gly Ile Leu Lys Val Val
    50                  55                  60

Lys Ala Leu Asp Tyr Glu Gln Leu Gln Ser Val Lys Leu Ser Ile Ala
65                  70                  75                  80

Val Lys Asn Lys Ala Glu Phe His Gln Ser Val Ile Ser Arg Tyr Arg
                85                  90                  95

Val Gln Ser Thr Pro Val Thr Ile Gln Val Ile Asn Val Arg Glu Gly
            100                 105                 110

Ile Ala Phe Arg Pro Ala Ser Lys Thr Phe Thr Val Gln Lys Gly Ile
        115                 120                 125

Ser Ser Lys Lys Leu Val Asp Tyr Ile Leu Gly Thr Tyr Gln Ala Ile
    130                 135                 140

Asp Glu Asp Thr Asn Lys Ala Ala Ser Asn Val Lys Tyr Val Met Gly
145                 150                 155                 160

Arg Asn Asp Gly Gly Tyr Leu Met Ile Asp Ser Lys Thr Ala Glu Ile
                165                 170                 175

Lys Phe Val Lys Asn Met Asn Arg Asp Ser Thr Phe Ile Val Asn Lys
            180                 185                 190

Thr Ile Thr Ala Glu Val Leu Ala Ile Asp Glu Tyr Thr Gly Lys Thr
        195                 200                 205

Ser Thr Gly Thr Val Tyr Val Arg Val Pro Asp Phe Asn Asp Asn Cys
    210                 215                 220

Pro Thr Ala Val Leu Glu Lys Asp Ala Val Cys Ser Ser Ser Pro Ser
225                 230                 235                 240

Val Val Val Ser Ala Arg Thr Leu Asn Asn Arg Tyr Thr Gly Pro Tyr
                245                 250                 255

Thr Phe Ala Leu Glu Asp Gln Pro Val Lys Leu Pro Ala Val Trp Ser
            260                 265                 270

Ile Thr Thr Leu Asn Ala Thr Ser Ala Leu Leu Arg Ala Gln Glu Gln
        275                 280                 285

Ile Pro Pro Gly Val Tyr His Ile Ser Leu Val Leu Thr Asp Ser Gln
    290                 295                 300

Asn Asn Arg Cys Glu Met Pro Arg Ser Leu Thr Leu Glu Val Cys Gln
305                 310                 315                 320

Cys Asp Asn Arg Gly Ile Cys Gly Thr Ser Tyr Pro Thr Thr Ser Pro
                325                 330                 335

Gly Thr Arg Tyr Gly Arg Pro His Ser Gly Arg
            340                 345

```
<210> SEQ ID NO 12
<211> LENGTH: 457
<212> TYPE: PRT
<213> ORGANISM: Homo sapiens

<400> SEQUENCE: 12
```

| | | | | | | | | | | | | | | | |
|---|---|---|---|---|---|---|---|---|---|---|---|---|---|---|---|
|Gln|Gln|Ile|Phe|Met|Gly|Glu|Ile|Glu|Asn|Ser|Ala|Ser|Asn|Ser| |
|1| | | |5| | | |10| | | | |15| | |
|Leu|Val|Met|Ile|Leu|Asn|Ala|Thr|Asp|Ala|Asp|Glu|Pro|Asn|His|Leu|
| | | |20| | | | |25| | | | |30| | |
|Asn|Ser|Lys|Ile|Ala|Phe|Lys|Ile|Val|Ser|Gln|Glu|Pro|Ala|Gly|Thr|
| | | | |35| | | | |40| | | | |45| |
|Pro|Met|Phe|Leu|Leu|Ser|Arg|Asn|Thr|Gly|Val|Arg|Thr|Leu|Thr| |
| |50| | | | |55| | | | |60| | | | |
|Asn|Ser|Leu|Asp|Arg|Glu|Gln|Ala|Ser|Ser|Tyr|Arg|Leu|Val|Val|Ser|
|65| | | | |70| | | | |75| | | | |80|
|Gly|Ala|Asp|Lys|Asp|Gly|Glu|Gly|Leu|Ser|Thr|Gln|Cys|Glu|Cys|Asn|
| | | | |85| | | | |90| | | | |95| |
|Ile|Lys|Val|Lys|Asp|Val|Asn|Asp|Asn|Phe|Pro|Met|Phe|Arg|Asp|Ser|
| | | | |100| | | | |105| | | | |110| |
|Gln|Tyr|Ser|Ala|Arg|Ile|Glu|Glu|Asn|Ile|Leu|Ser|Ser|Glu|Leu|Leu|
| | | | |115| | | | |120| | | | |125| |
|Arg|Phe|Gln|Val|Thr|Asp|Leu|Asp|Glu|Glu|Tyr|Thr|Asp|Asn|Trp|Leu|
| |130| | | | |135| | | | |140| | | | |
|Ala|Val|Tyr|Phe|Phe|Thr|Ser|Gly|Asn|Glu|Gly|Asn|Trp|Phe|Glu|Ile|
|145| | | | |150| | | | |155| | | | |160|
|Gln|Thr|Asp|Pro|Arg|Thr|Asn|Glu|Gly|Ile|Leu|Lys|Val|Val|Lys|Ala|
| | | | |165| | | | |170| | | | |175| |
|Leu|Asp|Tyr|Glu|Gln|Leu|Gln|Ser|Val|Lys|Leu|Ser|Ile|Ala|Val|Lys|
| | | | |180| | | | |185| | | | |190| |
|Asn|Lys|Ala|Glu|Phe|His|Gln|Ser|Val|Ile|Ser|Arg|Tyr|Arg|Val|Gln|
| | | | |195| | | | |200| | | | |205| |
|Ser|Thr|Pro|Val|Thr|Ile|Gln|Val|Ile|Asn|Val|Arg|Glu|Gly|Ile|Ala|
| | |210| | | | |215| | | | |220| | | |
|Phe|Arg|Pro|Ala|Ser|Lys|Thr|Phe|Thr|Val|Gln|Lys|Gly|Ile|Ser|Ser|
|225| | | | |230| | | | |235| | | | |240|
|Lys|Lys|Leu|Val|Asp|Tyr|Ile|Leu|Gly|Thr|Tyr|Gln|Ala|Ile|Asp|Glu|
| | | | |245| | | | |250| | | | |255| |
|Asp|Thr|Asn|Lys|Ala|Ala|Ser|Asn|Val|Lys|Tyr|Val|Met|Gly|Arg|Asn|
| | | | |260| | | | |265| | | | |270| |
|Asp|Gly|Gly|Tyr|Leu|Met|Ile|Asp|Ser|Lys|Thr|Ala|Glu|Ile|Lys|Phe|
| | |275| | | | |280| | | | |285| | | |
|Val|Lys|Asn|Met|Asn|Arg|Asp|Ser|Thr|Phe|Ile|Val|Asn|Lys|Thr|Ile|
| |290| | | | |295| | | | |300| | | | |
|Thr|Ala|Glu|Val|Leu|Ala|Ile|Asp|Glu|Tyr|Thr|Gly|Lys|Thr|Ser|Thr|
|305| | | | |310| | | | |315| | | | |320|
|Gly|Thr|Val|Tyr|Val|Arg|Val|Pro|Asp|Phe|Asn|Asp|Asn|Cys|Pro|Thr|
| | | | |325| | | | |330| | | | |335| |
|Ala|Val|Leu|Glu|Lys|Asp|Ala|Val|Cys|Ser|Ser|Ser|Pro|Ser|Val|Val|
| | | | |340| | | | |345| | | | |350| |
|Val|Ser|Ala|Arg|Thr|Leu|Asn|Asn|Arg|Tyr|Thr|Gly|Pro|Tyr|Thr|Phe|
| | |355| | | | |360| | | | |365| | | |
|Ala|Leu|Glu|Asp|Gln|Pro|Val|Lys|Leu|Pro|Ala|Val|Trp|Ser|Ile|Thr|
| |370| | | | |375| | | | |380| | | | |

```
Thr Leu Asn Ala Thr Ser Ala Leu Leu Arg Ala Gln Glu Gln Ile Pro
385                 390                 395                 400

Pro Gly Val Tyr His Ile Ser Leu Val Leu Thr Asp Ser Gln Asn Asn
                405                 410                 415

Arg Cys Glu Met Pro Arg Ser Leu Thr Leu Glu Val Cys Gln Cys Asp
            420                 425                 430

Asn Arg Gly Ile Cys Gly Thr Ser Tyr Pro Thr Thr Ser Pro Gly Thr
        435                 440                 445

Arg Tyr Gly Arg Pro His Ser Gly Arg
    450                 455
```

<210> SEQ ID NO 13
<211> LENGTH: 68
<212> TYPE: PRT
<213> ORGANISM: Homo sapiens

<400> SEQUENCE: 13

```
Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Val Ile Thr
65
```

<210> SEQ ID NO 14
<211> LENGTH: 13
<212> TYPE: PRT
<213> ORGANISM: Artificial Sequence
<220> FEATURE:
<223> OTHER INFORMATION: Synthetic sequence

<400> SEQUENCE: 14

```
Ser Gly Gly Gly Gly Ser Gly Gly Gly Gly Ser Ser Gly
1               5                   10
```

<210> SEQ ID NO 15
<211> LENGTH: 42
<212> TYPE: PRT
<213> ORGANISM: Homo sapiens

<400> SEQUENCE: 15

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 16
<211> LENGTH: 112
<212> TYPE: PRT
<213> ORGANISM: Homo sapiens

<400> SEQUENCE: 16

```
Arg Val Lys Phe Ser Arg Ser Ala Asp Ala Pro Ala Tyr Gln Gln Gly
1               5                   10                  15
```

-continued

```
Gln Asn Gln Leu Tyr Asn Glu Leu Asn Leu Gly Arg Arg Glu Tyr
             20                  25                  30

Asp Val Leu Asp Lys Arg Gly Arg Asp Pro Glu Met Gly Gly Lys
         35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
             100                 105                 110
```

<210> SEQ ID NO 17
<211> LENGTH: 37
<212> TYPE: DNA
<213> ORGANISM: Artificial Sequence
<220> FEATURE:
<223> OTHER INFORMATION: Synthetic construct

<400> SEQUENCE: 17
ctagcaggat ccgccaccat ggccttacca gtgaccg          37

<210> SEQ ID NO 18
<211> LENGTH: 27
<212> TYPE: DNA
<213> ORGANISM: Artificial Sequence
<220> FEATURE:
<223> OTHER INFORMATION: Synthetic construct

<400> SEQUENCE: 18
tctattcgca attccggcct ggcggcg          27

<210> SEQ ID NO 19
<211> LENGTH: 35
<212> TYPE: DNA
<213> ORGANISM: Artificial Sequence
<220> FEATURE:
<223> OTHER INFORMATION: Synthetic construct

<400> SEQUENCE: 19
ctcagggagg aagcccacca cgacgccagc gccgc          35

<210> SEQ ID NO 20
<211> LENGTH: 33
<212> TYPE: DNA
<213> ORGANISM: Artificial Sequence
<220> FEATURE:
<223> OTHER INFORMATION: Synthetic construct

<400> SEQUENCE: 20
ccccgtttgg tgataaccag tgacaggaga agg          33

<210> SEQ ID NO 21
<211> LENGTH: 34
<212> TYPE: DNA
<213> ORGANISM: Artificial Sequence
<220> FEATURE:
<223> OTHER INFORMATION: Synthetic construct

<400> SEQUENCE: 21
ctggttatca ccaaacgggg cagaaagaaa ctcc          34

```
<210> SEQ ID NO 22
<211> LENGTH: 38
<212> TYPE: DNA
<213> ORGANISM: Artificial sequence
<220> FEATURE:
<223> OTHER INFORMATION: Synthetic construct

<400> SEQUENCE: 22
ttcactctca gttcacatcc tccttcttct tcttctgg                              38

<210> SEQ ID NO 23
<211> LENGTH: 34
<212> TYPE: DNA
<213> ORGANISM: Artificial Sequence
<220> FEATURE:
<223> OTHER INFORMATION: Synthetic construct

<400> SEQUENCE: 23
gatgtgaact gagagtgaag ttcagcagga gcgc                                  34

<210> SEQ ID NO 24
<211> LENGTH: 34
<212> TYPE: DNA
<213> ORGANISM: Artificial Sequence
<220> FEATURE:
<223> OTHER INFORMATION: Synthetic construct

<400> SEQUENCE: 24
ggttgattgt cgacgcggat cttagcgagg gggc                                  34

<210> SEQ ID NO 25
<211> LENGTH: 31
<212> TYPE: DNA
<213> ORGANISM: Artificial Sequence
<220> FEATURE:
<223> OTHER INFORMATION: Synthetic construct

<400> SEQUENCE: 25
ccaggccgga attgcgaata gagactaaag g                                     31

<210> SEQ ID NO 26
<211> LENGTH: 29
<212> TYPE: DNA
<213> ORGANISM: Artificial Sequence
<220> FEATURE:
<223> OTHER INFORMATION: Synthetic construct

<400> SEQUENCE: 26
cgtggtgggc ttcctccctg agtgcggcc                                        29

<210> SEQ ID NO 27
<211> LENGTH: 35
<212> TYPE: DNA
<213> ORGANISM: Artificial sequence
<220> FEATURE:
<223> OTHER INFORMATION: Synthetic construct

<400> SEQUENCE: 27
ggatcctgct agactcacga cacctgaaat ggaag                                 35

<210> SEQ ID NO 28
<211> LENGTH: 36
<212> TYPE: DNA
<213> ORGANISM: Artificial Sequence
<220> FEATURE:
<223> OTHER INFORMATION: Synthetic construct
```

<400> SEQUENCE: 28
gaggaggtcg acattcgtga ggctccggtg cccgtc         36

<210> SEQ ID NO 29
<211> LENGTH: 21
<212> TYPE: DNA
<213> ORGANISM: Artificial Sequence
<220> FEATURE:
<223> OTHER INFORMATION: Synthetic construct

<400> SEQUENCE: 29
gaggaggagg gatccgccac c         21

<210> SEQ ID NO 30
<211> LENGTH: 23
<212> TYPE: DNA
<213> ORGANISM: Artificial Sequence
<220> FEATURE:
<223> OTHER INFORMATION: Synthetic construct

<400> SEQUENCE: 30
cctccgccgc cgctagctct gcc         23

<210> SEQ ID NO 31
<211> LENGTH: 34
<212> TYPE: DNA
<213> ORGANISM: Artificial Sequence
<220> FEATURE:
<223> OTHER INFORMATION: Synthetic construct

<400> SEQUENCE: 31
cctccgccgc cgctagcctt ttccagcacg gcgg         34

<210> SEQ ID NO 32
<211> LENGTH: 26
<212> TYPE: DNA
<213> ORGANISM: Artificial Sequence
<220> FEATURE:
<223> OTHER INFORMATION: Synthetic construct

<400> SEQUENCE: 32
tctcctcgct agcgaaggca atgccc         26

<210> SEQ ID NO 33
<211> LENGTH: 37
<212> TYPE: DNA
<213> ORGANISM: Artificial sequence
<220> FEATURE:
<223> OTHER INFORMATION: Synthetic construct

<400> SEQUENCE: 33
tccgccgccg ctagcccgga acatagggaa gttgtcg         37

<210> SEQ ID NO 34
<211> LENGTH: 40
<212> TYPE: DNA
<213> ORGANISM: Artificial Sequence
<220> FEATURE:
<223> OTHER INFORMATION: Synthetic construct

<400> SEQUENCE: 34
aagcggcggc agaaacgcat cctggacatc aacgacaacc         40

<210> SEQ ID NO 35
<211> LENGTH: 37

```
<212> TYPE: DNA
<213> ORGANISM: Artificial Sequence
<220> FEATURE:
<223> OTHER INFORMATION: Synthetic construct

<400> SEQUENCE: 35
gatgcgtttc tgccgccgct tggcctgctg cattgtc                              37

<210> SEQ ID NO 36
<211> LENGTH: 2423
<212> TYPE: DNA
<213> ORGANISM: Artificial Sequence
<220> FEATURE:
<223> OTHER INFORMATION: Synthetic construct

<400> SEQUENCE: 36
atggctctgc ctgtgacagc tctgctgctg cctctggccc tgctgctgca tgtgccagac    60
ctggctccga gctgcggatc gagacaaagg gccagtacga cgaggaagag atgacaatgc   120
agcaggccaa gcggcggcag aaacgcgagt gggtcaagtt cgccaagccc tgcagagagg   180
gcgaggacaa cagcaagcgg aaccctatcg ccaagatcac cagcgactac caggccaccc   240
agaagatcac ctaccggatc agcggcgtgg gcatcgacca gccccctttc ggcatcttcg   300
tggtggacaa gaacaccggc gacatcaaca tcaccgccat cgtggacaga gaggaaaccc   360
ccagcttcct gatcacctgt cgggcccctg aatgcccagg cctggacgtg aaaagcccc   420 tgatcctgac cgtgaagatc ctggacatca cgacaaccc cccgtgttc agccagcaga   480 tcttcatggg cgagatcgag aaaacagccg ccagcaacag cctcgtgatg atcctgaacg   540
ccaccgacgc cgacgagccc aaccacctga atagcaagat cgccttcaag atcgtgtccc   600
aggaacccgc cggaaccccc atgttcctgc tgagcagaaa taccggcgaa gtgcggaccc   660
tgaccaacag cctggataga gagcaggcca gcagctaccg gctggtggtg tctggcgctg   720
acaaggatgg cgagggcctg agcacacagt gcgagtgcaa catcaaagtg aaggacgtga   780
acgacaactt ccctatgttc cgggacagcc agtacagcgc ccggatcgaa gagaacatcc   840
tgagcagcga gctgctgcgg ttccaagtga ccgacctgga cgaagagtac accgacaact   900
ggctagccgt gtacttcttc accagcggca acgagggcaa ttggttcgag atccagaccg   960
accccccgga caatgagggc atcctgaagg tcgtgaaggc cctggactac gagcagctgc  1020
agagcgtgaa gctgtctatc gccgtgaaga caaggccga gttccaccag tccgtgatca  1080
gccggtacag agtgcagagc accccgtga ccatccaagt gatcaacgtg cgcgagggca  1140
ttgccttcag acccgccagc aagaccttca ccgtgcagaa gggcatcagc agcaagaaac  1200
tggtggacta catcctgggc acctatcagg ccatcgacga ggacaccaac aaagccgcct  1260
ccaacgtgaa atacgtgatg ggccggaacg acggcggcta cctgatgatc gattccaaga  1320
ccgccgagat caagttcgtg aagaatatga accgggactc caccttcatc gtgaacaaga  1380
ccatcacagc cgaggtgctg gccatcgatg agtataccgg caagaccagc accggcaccg  1440
tgtacgtgcg ggtgcccgac ttcaacgata actgccctac cgccgtgctg aaaaggacg  1500 ccgtgtgtag cagcagcccc agcgtggtgg tgtccgccag aaccctgaac aaccggtaca  1560
ccggccccta ccttcgcc ctggaagatc agcctgaa gctgcccgcc gtgtggtcca  1620
tcaccacact gaatgccacc agcgccctgc tgagagccca ggaacagatt cccctggcg  1680 tgtaccacat cagcctggtg ctgaccgaca gccagaacaa cagatgcgag atgcccggt  1740 ccctgaccct ggaagtgtgc cagtgcgaca acagaggcat ctgcggcacc agctacccta  1800
```

```
ccacctctcc cggcaccaga tacggcagac ctcacagcgg cagagctagc ggcggcggag    1860
gaagcggagg cggaggatct agcggcatct acatctgggc ccctctggcc ggaacatgcg    1920
gagtgctgct gctgagcctc gtgatcaccc tgtactgcaa gagaggccgg aagaagctgc    1980
tgtacatctt caagcagccc ttcatgcggc ccgtgcagac cacccaggaa gaggacggct    2040
gcagctgtcg gttccccgag aagaagaag gcggctgcga actgagagtg aagttcagca    2100
gaagcgccga cgcccctgcc taccagcagg gacagaacca gctgtacaac gagctgaacc    2160
tgggcagacg ggaagagtac gacgtgctgg acaagcggag aggcagggac cctgagatgg    2220
gcggcaagcc cagaagaaag aaccccccagg aaggcctgta taacgaactg cagaaagaca    2280
agatggccga ggcctacagc gagatcggaa tgaagggcga gcggagaaga ggcaagggcc    2340
acgacggact gtaccaggga ctgagcaccg ccaccaagga cacctacgac gccctgcaca    2400
tgcaggccct gccccctaga taa                                             2423

<210> SEQ ID NO 37
<211> LENGTH: 1164
<212> TYPE: DNA
<213> ORGANISM: Artificial Sequence
<220> FEATURE:
<223> OTHER INFORMATION: Synthetic construct

<400> SEQUENCE: 37
atggcacttc cagtgaccgc tctgctcctg ccactggccc tgctgctcca cgctgcccgc      60
ccgggcagcg agttcaggat ccaagtcagg gattataata ctaaaaacgg taccatcaag    120
tggcattcca tacgcaggca gaaaagggag tggattaagt ttgctgccgc gtgccgggag    180
ggtgaagaca atagcaaacg gaatcccatt gcaaagatac atagcgattg cgctgccaat    240
cagcaggtta catatcgaat ctccggcgtg gggattgacc agcctcctta tggcattttc    300
gtcattaacc aaaagactgg cgagataaat atcacatcaa ttgtggaccg ggaagtgacg    360 ccgttttta tcatctactg tagagctctg aactccatgg ccaggatct ggaaaggcca    420 ctggagctga gggtcagggt ccttgacatc aatgacaatc ccccgtctt ttccatggcc    480 acgttcgccg acagattga ggaaaatagc aatgccaata cactggtgat gatcctgaac    540
gctaccgacg ctgacgagcc gaataatctg aacagtaaaa ttgcttttaa gatcattcgg    600
caggagccat cagacagccc aatgtttatc attaacagaa acaccggaga gatccgcaca    660
atgaacaatt tcctggatag ggaacagtat ggacagtatg cactcgctgt tcggggctcc    720
gaccgggacg tggagctga tgcatgagt gccgagtgcg agtgcaatat caagatactc    780
gacgtaaatg ataatattcc atacatggaa cagagctctt acactatcga gatccaggag    840
aatactctca actctaatct tcttgaaatt agagtgattg atctcgacga ggaattttct    900
gccaattgga tggctgtcat cttctttatt agtggtaacg agggtaactg gttcgagata    960
gaaatgaatg aaaggacaaa tgtgggaatc ttgaaggtgg ttaaaccact ggactacgaa    1020
gcaatgcaat cactccagct gtcaataggc gtcagaaata aggcggagtt ccatcactcc    1080
attatgtccc agtataaatt gaaagccagt gccataagcg taaccgtgtt gaacgtgata    1140
gaagggcctg ttttgcatc cgga                                             1164

<210> SEQ ID NO 38
<211> LENGTH: 388
<212> TYPE: PRT
<213> ORGANISM: Artificial Sequence
<220> FEATURE:
<223> OTHER INFORMATION: Synthetic construct
```

-continued

<400> SEQUENCE: 38

```
Met Ala Leu Pro Val Thr Ala Leu Leu Pro Leu Ala Leu Leu Leu
1               5                   10                  15

His Ala Ala Arg Pro Gly Ser Glu Phe Arg Ile Gln Val Arg Asp Tyr
            20                  25                  30

Asn Thr Lys Asn Gly Thr Ile Lys Trp His Ser Ile Arg Arg Gln Lys
        35                  40                  45

Arg Glu Trp Ile Lys Phe Ala Ala Cys Arg Gly Glu Asp Asn
    50                  55                  60

Ser Lys Arg Asn Pro Ile Ala Lys Ile His Ser Asp Cys Ala Ala Asn
65                  70                  75                  80

Gln Gln Val Thr Tyr Arg Ile Ser Gly Val Gly Ile Asp Gln Pro Pro
                85                  90                  95

Tyr Gly Ile Phe Val Ile Asn Gln Lys Thr Gly Glu Ile Asn Ile Thr
            100                 105                 110

Ser Ile Val Asp Arg Glu Val Thr Pro Phe Phe Ile Ile Tyr Cys Arg
        115                 120                 125

Ala Leu Asn Ser Met Gly Gln Asp Leu Glu Arg Pro Leu Glu Leu Arg
    130                 135                 140

Val Arg Val Leu Asp Ile Asn Asp Asn Pro Pro Val Phe Ser Met Ala
145                 150                 155                 160

Thr Phe Ala Gly Gln Ile Glu Glu Asn Ser Asn Ala Asn Thr Leu Val
                165                 170                 175

Met Ile Leu Asn Ala Thr Asp Ala Asp Glu Pro Asn Asn Leu Asn Ser
            180                 185                 190

Lys Ile Ala Phe Lys Ile Ile Arg Gln Glu Pro Ser Asp Ser Pro Met
        195                 200                 205

Phe Ile Ile Asn Arg Asn Thr Gly Glu Ile Arg Thr Met Asn Asn Phe
210                 215                 220

Leu Asp Arg Glu Gln Tyr Gly Gln Tyr Ala Leu Ala Val Arg Gly Ser
225                 230                 235                 240

Asp Arg Asp Gly Gly Ala Asp Gly Met Ser Ala Glu Cys Glu Cys Asn
                245                 250                 255

Ile Lys Ile Leu Asp Val Asn Asp Asn Ile Pro Tyr Met Glu Gln Ser
            260                 265                 270

Ser Tyr Thr Ile Glu Ile Gln Glu Asn Thr Leu Asn Ser Asn Leu Leu
        275                 280                 285

Glu Ile Arg Val Ile Asp Leu Asp Glu Glu Phe Ser Ala Asn Trp Met
    290                 295                 300

Ala Val Ile Phe Phe Ile Ser Gly Asn Glu Gly Asn Trp Phe Glu Ile
305                 310                 315                 320

Glu Met Asn Glu Arg Thr Asn Val Gly Ile Leu Lys Val Val Lys Pro
                325                 330                 335

Leu Asp Tyr Glu Ala Met Gln Ser Leu Gln Leu Ser Ile Gly Val Arg
            340                 345                 350

Asn Lys Ala Glu Phe His His Ser Ile Met Ser Gln Tyr Lys Leu Lys
        355                 360                 365

Ala Ser Ala Ile Ser Val Thr Val Leu Asn Val Ile Glu Gly Pro Val
    370                 375                 380

Phe Ala Ser Gly
385
```

<210> SEQ ID NO 39
<211> LENGTH: 1500
<212> TYPE: DNA
<213> ORGANISM: Artificial Sequence
<220> FEATURE:
<223> OTHER INFORMATION: Synthetic construct

<400> SEQUENCE: 39

```
atggcacttc cagtgaccgc tctgctcctg ccactggccc tgctgctcca cgctgcccgc      60
ccgggcagcg agttcaggat ccaagtcagg gattataata ctaaaaacgg taccatcaag     120
tggcattcca tacgcaggca gaaaagggag tggattaagt ttgctgccgc gtgccgggag     180
ggtgaagaca atagcaaacg gaatcccatt gcaaagatac atagcgattg cgctgccaat     240
cagcaggtta catatcgaat ctccggcgtg gggattgacc agcctcctta tggcattttc     300
gtcattaacc aaaagactgg cgagataaat atcacatcaa ttgtggaccg ggaagtgacg     360
ccgttttta tcatctactg tagagctctg aactccatgg ccaggatct ggaaaggcca      420
ctggagctga gggtcaggt ccttgacatc aatgacaatc cccccgtctt ttccatggcc      480
acgttcgccg acagattga ggaaaatagc aatgccaata cactggtgat gatcctgaac      540
gctaccgacg ctgacgagcc gaataatctg aacagtaaaa ttgcttttaa gatcattcgg     600
caggagccat cagacagccc aatgtttatc attaacagaa acaccggaga gatccgcaca     660
atgaacaatt tcctggatag ggaacagtat ggacagtatg cactcgctgt tcggggctcc     720
gaccgggacg gtggagctga tggcatgagt gccgagtgcg agtgcaatat caagatactc     780
gacgtaaatg ataatattcc atacatggaa cagagctctt acactatcga gatccaggag     840
aatactctca actctaatct tcttgaaatt agagtgattg atctcgacga ggaattttct     900
gccaattgga tggctgtcat cttctttatt agtggtaacg agggtaactg gttcgagata     960
gaaatgaatg aaaggacaaa tgtgggaatc ttgaaggtgg ttaaaccact ggactacgaa    1020
gcaatgcaat cactccagct gtcaataggc gtcagaaata aggcggagtt ccatcactcc    1080
attatgtccc agtataaatt gaaagccagt gccataagcg taaccgtgtt gaacgtgata    1140
gaagggcctg ttttttcgccc tgggtccaaa acctacgttg tgacaggaaa catgggatcc    1200
aacgacaaag tcggcgactt cgtcgcaaca gacctggaca ccggtcgccc ttccacaact    1260
gtgcggtacg tgatgggaaa caatccagcc gacttgttgg cagtcgatag caggacaggg    1320
aagctgaccc ttaaaaacaa ggttacaaaa gaacaatata acatgctggg cggcaaatat    1380
cagggaacca ttttgtcaat cgacgacaac ctgcagcgca cgtgcacggg gacgatcaac    1440
atcaacatcc agagctttgg gaatgacgat agaaccaaca cagagcccaa cgctagcgga    1500
```

<210> SEQ ID NO 40
<211> LENGTH: 500
<212> TYPE: PRT
<213> ORGANISM: Artificial Sequence
<220> FEATURE:
<223> OTHER INFORMATION: Synthetic construct

<400> SEQUENCE: 40

```
Met Ala Leu Pro Val Thr Ala Leu Leu Leu Pro Leu Ala Leu Leu Leu
1               5                   10                  15

His Ala Ala Arg Pro Gly Ser Glu Phe Arg Ile Gln Val Arg Asp Tyr
                20                  25                  30

Asn Thr Lys Asn Gly Thr Ile Lys Trp His Ser Ile Arg Arg Gln Lys
            35                  40                  45

Arg Glu Trp Ile Lys Phe Ala Ala Ala Cys Arg Glu Gly Glu Asp Asn
```

```
            50                  55                  60
Ser Lys Arg Asn Pro Ile Ala Lys Ile His Ser Asp Cys Ala Ala Asn
 65                  70                  75                  80

Gln Gln Val Thr Tyr Arg Ile Ser Gly Val Gly Ile Asp Gln Pro Pro
                 85                  90                  95

Tyr Gly Ile Phe Val Ile Asn Gln Lys Thr Gly Glu Ile Asn Ile Thr
                100                 105                 110

Ser Ile Val Asp Arg Glu Val Thr Pro Phe Phe Ile Ile Tyr Cys Arg
                115                 120                 125

Ala Leu Asn Ser Met Gly Gln Asp Leu Glu Arg Pro Leu Glu Leu Arg
130                 135                 140

Val Arg Val Leu Asp Ile Asn Asp Asn Pro Pro Val Phe Ser Met Ala
145                 150                 155                 160

Thr Phe Ala Gly Gln Ile Glu Glu Asn Ser Asn Ala Asn Thr Leu Val
                165                 170                 175

Met Ile Leu Asn Ala Thr Asp Ala Asp Glu Pro Asn Asn Leu Asn Ser
                180                 185                 190

Lys Ile Ala Phe Lys Ile Ile Arg Gln Glu Pro Ser Asp Ser Pro Met
                195                 200                 205

Phe Ile Ile Asn Arg Asn Thr Gly Glu Ile Arg Thr Met Asn Asn Phe
                210                 215                 220

Leu Asp Arg Glu Gln Tyr Gly Gln Tyr Ala Leu Ala Val Arg Gly Ser
225                 230                 235                 240

Asp Arg Asp Gly Gly Ala Asp Gly Met Ser Ala Glu Cys Glu Cys Asn
                245                 250                 255

Ile Lys Ile Leu Asp Val Asn Asp Asn Ile Pro Tyr Met Glu Gln Ser
                260                 265                 270

Ser Tyr Thr Ile Glu Ile Gln Glu Asn Thr Leu Asn Ser Asn Leu Leu
                275                 280                 285

Glu Ile Arg Val Ile Asp Leu Asp Glu Glu Phe Ser Ala Asn Trp Met
                290                 295                 300

Ala Val Ile Phe Phe Ile Ser Gly Asn Glu Gly Asn Trp Phe Glu Ile
305                 310                 315                 320

Glu Met Asn Glu Arg Thr Asn Val Gly Ile Leu Lys Val Val Lys Pro
                325                 330                 335

Leu Asp Tyr Glu Ala Met Gln Ser Leu Gln Leu Ser Ile Gly Val Arg
                340                 345                 350

Asn Lys Ala Glu Phe His His Ser Ile Met Ser Gln Tyr Lys Leu Lys
                355                 360                 365

Ala Ser Ala Ile Ser Val Thr Val Leu Asn Val Ile Glu Gly Pro Val
370                 375                 380

Phe Arg Pro Gly Ser Lys Thr Tyr Val Val Thr Gly Asn Met Gly Ser
385                 390                 395                 400

Asn Asp Lys Val Gly Asp Phe Val Ala Thr Asp Leu Asp Thr Gly Arg
                405                 410                 415

Pro Ser Thr Thr Val Arg Tyr Val Met Gly Asn Asn Pro Ala Asp Leu
                420                 425                 430

Leu Ala Val Asp Ser Arg Thr Gly Lys Leu Thr Leu Lys Asn Lys Val
                435                 440                 445

Thr Lys Glu Gln Tyr Asn Met Leu Gly Gly Lys Tyr Gln Gly Thr Ile
                450                 455                 460

Leu Ser Ile Asp Asp Asn Leu Gln Arg Thr Cys Thr Gly Thr Ile Asn
465                 470                 475                 480
```

Ile Asn Ile Gln Ser Phe Gly Asn Asp Asp Arg Thr Asn Thr Glu Pro
            485                 490                 495

Asn Ala Ser Gly
            500

<210> SEQ ID NO 41
<211> LENGTH: 1674
<212> TYPE: DNA
<213> ORGANISM: Artificial Sequence
<220> FEATURE:
<223> OTHER INFORMATION: Synthetic construct

<400> SEQUENCE: 41

```
gaagaagaag ggtcagccac tatggcactt ccagtgaccg ctctgctcct gccactggcc      60
ctgctgctcc acgctgcccg cccgggcagc gagttcagga tccaagtcag ggattataat     120
actaaaaacg gtaccatcaa gtggcattcc atacgcaggc agaaaaggga gtggattaag     180
tttgctgccg cgtgccggga gggtgaagac aatagcaaac ggaatcccat gcaaagata      240
catagcgatt gcgctgccaa tcagcaggtt acatatcgaa tctccggcgt ggggattgac     300
cagcctcctt atggcatttt cgtcattaac caaaagactg gcgagataaa tatcacatca     360
attgtggacc gggaagtgac gccgtttttt atcatctact gtagagctct gaactccatg     420
ggccaggatc tggaaaggcc actggagctg agggtcaggg tccttgacat caatgacaat     480
ccccccgtct tttccatggc cacgttcgcc ggacagattg aggaaaatag caatgccaat     540
acactggtga tgatcctgaa cgctaccgac gctgacgagc cgataatct gaacagtaaa      600
attgcttta agatcattcg gcaggagcca tcagacagcc caatgtttat cattaacaga      660
aacaccggag gatccgcac aatgaacaat ttcctggata gggaacagta tggacagtat      720
gcactcgctg ttcggggctc cgaccgggac ggtggagctg atggcatgag tgccgagtgc     780
gagtgcaata tcaagatact cgacgtaaat gataatattc catacatgga acagagctct     840
tacactatcg agatccagga gaatactctc aactctaatc ttcttgaaat tagagtgatt     900
gatctcgacg aggaattttc tgccaattgg atggctgtca tcttctttat tagtggtaac     960
gagggtaact ggttcgagat agaaatgaat gaaaggacaa atgtgggaat cttgaaggtg    1020
gttaaaccac tggactacga agcaatgcaa tcactccagc tgtcaatagg cgtcagaaat    1080
aaggcggagt ccatcactc cattatgtcc cagtataaat tgaaagccag tgccataagc    1140
gtaaccgtgt tgaacgtgat agaagggcct gtttttcgcc ctgggtccaa aacctacgtt    1200
gtgacaggaa acatgggatc caacgacaaa gtcggcgact cgtcgcaaac agacctggac    1260
accggtcgcc cttccacaac tgtgcggtac gtgatgggaa acaatccagc cgacttgttg    1320
gcagtcgata gcaggacagg gaagctgacc cttaaaaaca aggttacaaa agaacaatat    1380
aacatgctgg gcggcaaata tcagggaacc attttgtcaa tcgacgacaa cctgcagcgc    1440
acgtgcacgg ggacgatcaa catcaacatc cagagctttg gaatgacga tagaaccaac    1500
acagagccca acacaaagat caccaccaat actggccgac aagaatccac ctccagcaca    1560
aactatgata cgtccactac cagtacagac tccagtcagg tttacagcag tgaacccggt    1620
aatggtgcca aggatctcct gagtgataat gttcattttg acccgctag cgga          1674
```

<210> SEQ ID NO 42
<211> LENGTH: 551
<212> TYPE: PRT
<213> ORGANISM: Artificial Sequence
<220> FEATURE:

<223> OTHER INFORMATION: Synthetic sequence

<400> SEQUENCE: 42

Met Ala Leu Pro Val Thr Ala Leu Leu Leu Pro Leu Ala Leu Leu Leu
1               5                   10                  15

His Ala Ala Arg Pro Gly Ser Glu Phe Arg Ile Gln Val Arg Asp Tyr
            20                  25                  30

Asn Thr Lys Asn Gly Thr Ile Lys Trp His Ser Ile Arg Arg Gln Lys
        35                  40                  45

Arg Glu Trp Ile Lys Phe Ala Ala Cys Arg Glu Gly Glu Asp Asn
    50                  55                  60

Ser Lys Arg Asn Pro Ile Ala Lys Ile His Ser Asp Cys Ala Ala Asn
65                  70                  75                  80

Gln Gln Val Thr Tyr Arg Ile Ser Gly Val Gly Ile Asp Gln Pro Pro
                85                  90                  95

Tyr Gly Ile Phe Val Ile Asn Gln Lys Thr Gly Glu Ile Asn Ile Thr
                100                 105                 110

Ser Ile Val Asp Arg Glu Val Thr Pro Phe Phe Ile Ile Tyr Cys Arg
            115                 120                 125

Ala Leu Asn Ser Met Gly Gln Asp Leu Glu Arg Pro Leu Glu Leu Arg
        130                 135                 140

Val Arg Val Leu Asp Ile Asn Asp Asn Pro Pro Val Phe Ser Met Ala
145                 150                 155                 160

Thr Phe Ala Gly Gln Ile Glu Glu Asn Ser Asn Ala Asn Thr Leu Val
                165                 170                 175

Met Ile Leu Asn Ala Thr Asp Ala Asp Glu Pro Asn Asn Leu Asn Ser
            180                 185                 190

Lys Ile Ala Phe Lys Ile Ile Arg Gln Glu Pro Ser Asp Ser Pro Met
        195                 200                 205

Phe Ile Ile Asn Arg Asn Thr Gly Glu Ile Arg Thr Met Asn Asn Phe
210                 215                 220

Leu Asp Arg Glu Gln Tyr Gly Gln Tyr Ala Leu Ala Val Arg Gly Ser
225                 230                 235                 240

Asp Arg Asp Gly Gly Ala Asp Gly Met Ser Ala Glu Cys Glu Cys Asn
                245                 250                 255

Ile Lys Ile Leu Asp Val Asn Asp Asn Ile Pro Tyr Met Glu Gln Ser
            260                 265                 270

Ser Tyr Thr Ile Glu Ile Gln Glu Asn Thr Leu Asn Ser Asn Leu Leu
        275                 280                 285

Glu Ile Arg Val Ile Asp Leu Asp Glu Glu Phe Ser Ala Asn Trp Met
290                 295                 300

Ala Val Ile Phe Phe Ile Ser Gly Asn Glu Gly Asn Trp Phe Glu Ile
305                 310                 315                 320

Glu Met Asn Glu Arg Thr Asn Val Gly Ile Leu Lys Val Val Lys Pro
                325                 330                 335

Leu Asp Tyr Glu Ala Met Gln Ser Leu Gln Leu Ser Ile Gly Val Arg
            340                 345                 350

Asn Lys Ala Glu Phe His His Ser Ile Met Ser Gln Tyr Lys Leu Lys
        355                 360                 365

Ala Ser Ala Ile Ser Val Thr Val Leu Asn Val Ile Glu Gly Pro Val
    370                 375                 380

Phe Arg Pro Gly Ser Lys Thr Tyr Val Val Thr Gly Asn Met Gly Ser
385                 390                 395                 400

-continued

```
Asn Asp Lys Val Gly Asp Phe Val Ala Thr Asp Leu Asp Thr Gly Arg
                405                 410                 415
Pro Ser Thr Thr Val Arg Tyr Val Met Gly Asn Asn Pro Ala Asp Leu
            420                 425                 430
Leu Ala Val Asp Ser Arg Thr Gly Lys Leu Thr Leu Lys Asn Lys Val
            435                 440                 445
Thr Lys Glu Gln Tyr Asn Met Leu Gly Gly Lys Tyr Gln Gly Thr Ile
    450                 455                 460
Leu Ser Ile Asp Asp Asn Leu Gln Arg Thr Cys Thr Gly Thr Ile Asn
465                 470                 475                 480
Ile Asn Ile Gln Ser Phe Gly Asn Asp Asp Arg Thr Asn Thr Glu Pro
                485                 490                 495
Asn Thr Lys Ile Thr Thr Asn Thr Gly Arg Gln Glu Ser Thr Ser Ser
            500                 505                 510
Thr Asn Tyr Asp Thr Ser Thr Thr Ser Thr Asp Ser Ser Gln Val Tyr
            515                 520                 525
Ser Ser Glu Pro Gly Asn Gly Ala Lys Asp Leu Leu Ser Asp Asn Val
    530                 535                 540
His Phe Gly Pro Ala Ser Gly
545                 550
```

UNITED STATES PATENT AND TRADEMARK OFFICE
CERTIFICATE OF CORRECTION

PATENT NO. : 11,407,804 B2
APPLICATION NO. : 16/390685
DATED : August 9, 2022
INVENTOR(S) : Payne et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 679 days.

Signed and Sealed this
Fourteenth Day of January, 2025

Derrick Brent
*Acting Director of the United States Patent and Trademark Office*